United States Patent
Slukvin et al.

(10) Patent No.: US 11,591,571 B2
(45) Date of Patent: Feb. 28, 2023

(54) PLURIPOTENT STEM CELL ASSAY

(71) Applicant: CYNATA THERAPEUTICS LIMITED, Victoria (AU)

(72) Inventors: Igor Slukvin, Verona, WI (US); Derek Hei, Madison, WI (US); Diana Drier, Madison, WI (US)

(73) Assignee: CYNATA THERAPEUTICS LIMITED, Victoria (AU)

(*) Notice: Subject to any disclaimer, the term of this patent is extended or adjusted under 35 U.S.C. 154(b) by 502 days.

(21) Appl. No.: 16/461,248

(22) PCT Filed: Nov. 15, 2017

(86) PCT No.: PCT/AU2017/051254
§ 371 (c)(1),
(2) Date: May 15, 2019

(87) PCT Pub. No.: WO2018/090084
PCT Pub. Date: May 24, 2018

(65) Prior Publication Data
US 2019/0390168 A1 Dec. 26, 2019

(30) Foreign Application Priority Data

Nov. 16, 2016 (AU) ................. 2016904679

(51) Int. Cl.
*C12N 5/0775* (2010.01)
*A61K 35/28* (2015.01)
*C12Q 1/6876* (2018.01)

(52) U.S. Cl.
CPC ............ *C12N 5/0662* (2013.01); *A61K 35/28* (2013.01); *C12Q 1/6876* (2013.01); *C12N 2500/46* (2013.01); *C12N 2501/115* (2013.01); *C12N 2501/155* (2013.01); *C12N 2501/16* (2013.01); *C12N 2506/45* (2013.01); *C12N 2533/50* (2013.01); *C12N 2533/52* (2013.01); *C12N 2533/54* (2013.01); *C12Q 2600/158* (2013.01)

(58) Field of Classification Search
None
See application file for complete search history.

(56) References Cited

U.S. PATENT DOCUMENTS

2012/0156254 A1  6/2012  Tryggvason et al.

FOREIGN PATENT DOCUMENTS

| JP | 2004535199 A | 11/2004 |
| KR | 20140125682 A | 10/2014 |
| RU | 2015100900 A | 8/2016 |
| WO | 2003006950 A2 | 1/2003 |
| WO | 2013041961 A1 | 3/2013 |
| WO | 2013192005 A2 | 12/2013 |
| WO | 2014037807 A2 | 3/2014 |
| WO | 2015065537 A1 | 5/2015 |
| WO | 2016131959 A1 | 8/2016 |

OTHER PUBLICATIONS

Claassen DA, Desler MM, Rizzino A. ROCK inhibition enhances the recovery and growth of cryopreserved human embryonic stem cells and human induced pluripotent stem cells. Mol Reprod Dev. Aug. 2009;76(8):722-32. (Year: 2009).*
Baharvand, H., Salekdeh, G., Taei, A. et al. An efficient and easy-to-use cryopreservation protocol for human ES and iPS cells. Nat Protoc 5, 588-594 (2010). (Year: 2010).*
Maldonado M, Luu RJ, Ramos ME, Nam J. ROCK inhibitor primes human induced pluripotent stem cells to selectively differentiate towards mesendodermal lineage via epithelial-mesenchymal transition-like modulation. Stem Cell Res. Sep. 2016;17(2):222-227. (Year: 2016).*
Simonson OE, Domogatskaya A, Volchkov P, Rodin S. The safety of human pluripotent stem cells in clinical treatment. Ann Med. 2015;47(5):370-80. (Year: 2015).*
Hentze H, Soong PL, Wang ST, Phillips BW, Putti TC, Dunn NR. Teratoma formation by human embryonic stem cells: evaluation of essential parameters for future safety studies. Stem Cell Res. May 2009;2(3):198-210. (Year: 2009).*
Okano H, Nakamura M, Yoshida K, Okada Y, Tsuji O, Nori S, Ikeda E, Yamanaka S, Miura K. Steps toward safe cell therapy using induced pluripotent stem cells. Circ Res. Feb. 1, 2013;112(3):523-33. (Year: 2013).*
Zhao, T., Zhang, ZN., Rong, Z. et al. Immunogenicity of induced pluripotent stem cells. Nature 474, 212-215 (2011). (Year: 2011).*

(Continued)

*Primary Examiner* — Kara D Johnson
(74) *Attorney, Agent, or Firm* — Melissa Hunter-Ensor; Leslie Serunian; Greenberg Traurig, LLP

(57) ABSTRACT

The invention relates to a method for detecting residual, undifferentiated pluripotent stem cells (PSCs) in a culture of cells differentiated from PSCs, the method comprising:
culturing the cells on a substrate coated with laminin-521 and E-cadherin in a medium comprising a ROCK inhibitor;
quantitating in the cultured cells expression of a marker of residual, undifferentiated PSCs; and
comparing the marker expression in the cultured cells with the marker expression in a reference culture of cells comprising a known proportion of PSCs,
wherein lower marker expression in the culture of cells than marker expression in the reference culture of cells indicates absence of residual, undifferentiated PSCs in the cultured cells or presence of residual, undifferentiated PSCs in the cultured cells at a proportion lower than the known proportion of PSCs in the reference culture of cells. The invention also relates to a method for manufacturing a therapeutic composition and a method for treating or preventing a condition in a subject.

14 Claims, 10 Drawing Sheets

Specification includes a Sequence Listing.

(56) References Cited

OTHER PUBLICATIONS

Naujok O, Kaldrack J, Taivankhuu T, Jörns A, Lenzen S. Selective removal of undifferentiated embryonic stem cells from differentiation cultures through HSV1 thymidine kinase and ganciclovir treatment. Stem Cell Rev Rep. Sep. 2010;6(3):450-61. (Year: 2010).*
Ben-David U, Gan QF, Golan-Lev T, Arora P, Yanuka O, Oren YS, Leikin-Frenkel A, Graf M, Garippa R, Boehringer M, Gromo G, Benvenisty N. Selective elimination of human pluripotent stem cells by an oleate synthesis inhibitor discovered in a high-throughput screen. Cell Stem Cell. Feb. 7, 2013;12(2):167-79 (Year: 2013).*
Richards M, Phoon CW, Goh GT, Seng EK, Guo XM, Tan CM, Chan WK, Lee JM. A new class of pluripotent stem cell cytotoxic small molecules. PLoS One. Mar. 19, 2014;9(3):e85039. (Year: 2014).*
Lee MO, Moon SH, Jeong HC, Yi JY, Lee TH, Shim SH, Rhee YH, Lee SH, Oh SJ, Lee MY, Han MJ, Cho YS, Chung HM, Kim KS, Cha HJ. Inhibition of pluripotent stem cell-derived teratoma formation by small molecules. Proc Natl Acad Sci U S A. Aug. 27, 2013; 110(35):E3281-90. (Year: 2013).*
Kuroda T, Yasuda S, Matsuyama S, Tano K, Kusakawa S, Sawa Y, Kawamata S, Sato Y. Highly sensitive droplet digital PCR method for detection of residual undifferentiated cells in cardiomyocytes derived from human pluripotent stem cells. Regen Ther. Oct. 27, 2015;2:17-23. (Year: 2015).*
Kuroda T, Yasuda S, Matsuyama S, Tano K, Kusakawa S, Sawa Y, Kawamata S, Sato Y. Highly sensitive droplet digital PCR method for detection of residual undifferentiated cells in cardiomyocytes derived from human pluripotent stem cells. Regen Ther. Oct. 27, 2015;2:17-23. Supplemental information (Year: 2015).*
Haque et al., "An Engineered N-Cadherin Substrate for Differentiation, Survival, and Selection of Pluripotent Stem Cell-Derived Neural Progenitors," PLoS One, Aug. 5, 2015; vol. 10, No. 8, pp. 1-19; XP055598695, DOI: 10.1371/journal.pone.0135170.
Nagaoka et al., "Culture of human pluripotent stem cells using completely defined conditions on a recombinant E-cadherin substratum," BMC Developmental Biology, Jun. 2, 2010, vol. 10, article 60, pp. 1-12; XP055127261, DOI: 10.1186/1471-213X-10-60.
Rodin et al., "Clonal culturing of human embryonic stem cells on laminin-521/E-cadherin matrix in defined and xeno-free environment," Nature Communications, Jan. 27, 2014; vol. 5, article 3195, pp. 1-13; XP055101581, DOI: 10.1038/ncomms4195.
Extended European Search Report in corresponding European Patent Application No. 17872623.8, dated Nov. 20, 2019 (10 pages).
Dziedzicka, D. et al., "A High Proliferation Rate is Critical for Reproducible and Standardized Embryoid Body Formation from Laminin-521-Based Human Pluripotent Stem Cell Cultures," Stem Cell Rev. and Rep., Aug. 2016, vol. 12, pp. 721-730.
Kuroda, T. et al., "Highly Sensitive In Vitro Methods for Detection of Residual Undifferentiated Cells in Retinal Pigment Epithelial Cells Derived from Human iPS Cells," PLOS One, 2012, vol. 7, e37343.
Tano, K. et al., "A Novel In Vitro Method for Detecting Undifferentiated Human Pluripotent Stem Cells as Impurities in Cell Therapy Products Using a Highly Efficient Culture System," PLOS One, 2014, vol. 9, e110496.

International Search Report and Written Opinion for corresponding PCT/AU2017/051254, dated Dec. 18, 2017 (15 pages).
Fernandez-Francos et al., "Mesenchymal Stem Cells as a Cornerstone in a Galaxy of Intercellular Signals: Basis for a New Era of Medicine," International Journal of Molecular Sciences, 2021, vol. 22, Article No. 3576, pp. 1-34.
Levy et al., "Shattering barriers toward clinically meaningful MSC therapies," Science Advances, Jul. 22, 2020, vol. 6, No. 30, eaba6884, pp. 1-18.
Soontararak et al., "Mesenchymal Stem Cells (MSC) Derived from Induced Pluripotent Stem Cells (iPSC) Equivalent to Adipose-Derived MSC in Promoting Intestinal Healing and Microbiome Normalization in Mouse Inflammatory Bowel Disease Model," Stem Cells Translational Medicine, 2018, vol. 7, pp. 456-467.
Zhou et al., "Reprogrammed mesenchymal stem cells derived from iPSCs promote bone repair in steroid-associated osteonecrosis of the femoral head," Stem Cell Research & Therapy, 2021, vol. 12, Article No. 175, pp. 1-16.
Zhuang et al., "Mesenchymal stem/stromal cell-based therapy: mechanism, systemic safety and biodistribution for precision clinical applications," Journal of Biomedical Science, 2021, vol. 28, Article No. 28, pp. 1-38.
Office Action dated Mar. 5, 2021 in corresponding Russian Patent Application No. 2019116152/10(030890) (8 pages).
English translation of the Office Action dated Mar. 5, 2021 in corresponding Russian Patent Application No. 2019116152/10(030890) (8 pages).
Search Report dated Mar. 5, 2021 in corresponding Russian Patent Application No. 2019116152/10(030890) (2 pages).
English translation of the Search Report dated Mar. 5, 2021 in corresponding Russian Patent Application No. 2019116152/10(030890) (2 pages).
Basma et al., "Differentiation and Transplantation of Human Embryonic Stem Cell-Derived Hepatocytes," Gastroenterology, Mar. 2009, vol. 136, No. 3, pp. 990-999.
El-Akabawy et al., "Implantation of undifferentiated and pre-differentiated human neural stem cells in the R6/2 transgenic mouse model of Huntington's disease," BMC Neuroscience, 2012, vol. 13, Article No. 97, pp. 1-13.
Reboucas et al., "Real Time PCR and Importance of Housekeepings Genes for Normalization and Quantification of mRNA Expression in Different Tissues," Brazilian Archives of Biology and Technology, Jan.-Feb. 2013, vol. 56, No. 1, pp. 143-154.
Office Action dated Sep. 15, 2021 in corresponding Canadian Patent Application No. 3,042,562 (4 pages).
Office Action dated Sep. 28, 2021 in corresponding Japanese Patent Application No. 2019-546949 (3 pages).
English Translation of the Office Action dated Sep. 28, 2021 in corresponding Japanese Patent Application No. 2019-546949 (3 pages).
Office Action dated Jul. 28, 2022 in corresponding Korean Patent Application No. 10-2019-7017135 (6 pages).
English translation of the Office Action dated Jul. 28, 2022 in corresponding Korean Patent Application No. 10-2019-7017135 (5 pages).

* cited by examiner

```
MAKRLCAGSALCVRGPRGPAPLLLVGLALLGAARAREEAGGGFSLHPPYFNLAEGARIAASATCGEEAPARGSPR
PTEDLYCKLVGGPVAGGDPNQTIRGQYCDICTAANSNKAHPASNAIDGTERWWQSPPLSRGLEYNEVNVTLDLGQ
VFHVAYVLIKFANSPRPDLWVLERSMDFGRTYQPWQFFASSKRDCLERFGPQTLERITRDDAAICTTEYSRIVPL
ENGEIVVSLVNGRPGAMNFSYSPLLREFTKATNVRLRFLRTNTLLGHLMGKALRDPTVTRRYYYSIKDISIGGRC
VCHGHADACDAKDPTDPFRLQCTCQHNTCGGTCDRCCPGFNQQPWKPATANSANECQSCNCYGHATDCYYDPEVD
RRRASQSLDGTYQGGGVCIDCQHHTTGVNCERCLPGFYRSPNHPLDSPHVCRRCNCESDFTDGTCEDLTGRCYCR
PNFSGERCDVCAEGFTGFPSCYPTPSSSNDTREQVLPAGQIVNCDCSAAGTQGNACRKDPRVGRCLCKPNFQGTH
CELCAPGFYGPGCQPCQCSSPGVADDRCDPDTGQCRCRVGFEGATCDRCAPGYFHFPLCQLCGCSPAGTLPEGCD
EAGRCLCQPEFAGPHCDRCRPGYHGFPNCQACTCDPRGALDQLCGAGGLCRCRPGYTGTACQECSPGFHGFPSCV
PCHCSAEGSLHAACDPRSGQCSCRPRVTGLRCDTCVPGAYNFPYCEAGSCHPAGLAPVDPALPEAQVPCMCRAHV
EGPSCDRCKPGFWGLSPSNPEGCTRCSCDLRGTLGGVAECQPGTGQCFCKPHVCGQACASCKDGFFGLDQADYFG
CRSCRCDIGGALGQSCEPRTGVCRCRPNTQGPTCSEPARDHYLPDLHHLRLELEEAATPEGHAVRFGFNPLEFEN
FSWRGYAQMAPVQPRIVARLNLTSPDLFWLVFRYVNRGAMSVSGRVSVREEGRSATCANCTAQSQPVAFPPSTEP
AFITVPQRGFGEPFVLNPGTWALRVEAEGVLLDYVVLLPSAYYEAALLQLRVTEACTYRPSAQQSGDNCLLYTHL
PLDGFPSAAGLEALCRQDNSLPRPCPTEQLSPSHPPLITCTGSDVDVQLQVAVPQPGRYALVVEYANEDARQEVG
VAVHTPQRAPQQGLLSLHPCLYSTLCRGTARDTQDHLAVFHLDSEASVRLTAEQARFFLHGVTLVPIEEFSPEFV
EPRVSCISSHGAFGPNSAACLPSRFPKPPQPIILRDCQVIPLPPGLPLTHAQDLTPAMSPAGPRPRPPTAVDPDA
EPTLLREPQATVVFTTHVPTLGRYAFLLHGYQPAHPTFPVEVLINAGRVWQGHANASFCPHGYGCRTLVVCEGQA
LLDVTHSELTVTVRVPKGRWLWLDYVLVVPENVYSFGYLREEPLDKSYDFISHCAAQGYHISPSSSSLFCRNAAA
SLSLFYNNGARPCGCHEVGATGPTCEPFGGQCPCHAHVIGRDCSRCATGYWGFPNCRPCDCGARLCDELTGQCIC
PPRTIPPDCLLCQPQTFGCHPLVGCEECNCSGPGIQELTDPTCDTDSGQCKCRPNVTGRRCDTCSPGFHGYPRCR
PCDCHEAGTAPGVCDPLTGQCYCKENVQGPKCDQCSLGTFSLDAANPKGCTRCFCFGATERCRSSSYTRQEFVDM
EGWVLLSTDRQVVPHERQPGTEMLRADLRHVPEAVPEAFPELYWQAPPSYLGDRVSSYGGTLRYELHSETQRGDV
FVPMESRPDVVLQGNQMSITFLEPAYPTPGHVRGQLQLVEGNFRHTETRNTVSREELMMVLASLEQLQIRALFS
QISSAVFLRRVALEVASPAGQGALASNVELCLCPASYRGDSCQECAPGFYRDVKGLFLGRCVPCQCHGHSDRCLP
GSGVCVDCQHNTEGAHCERCQAGFVSSRDDPSAPCVSCPCPLSVPSNNFAEGCVLRGGRTQCLCKPGYAGASCER
CAPGFFGNPLVLGSSCQPCDCSGNGDPNLLFSDCDPLTGACRGCLRHTTGPRCEICAPGFYGNALLPGNCTRCDC
TPCGTEACDPHSGHCLCKAGVTGRRCDRCQEGHFGFDGCGGCRPCACGPAAEGSECHPQSGQCHCRPGTMGPQCR
ECAPGYWGLPEQGCRRCQCPGGRCDPHTGRCNCPPGLSGERCDTCSQQHQVPVPGGPVGHSIHCEVCDHCVVLLL
DDLERAGALLPAIHEQLRGINASSMAWARLHRLNASIADLQSQLRSPLGPRHETAQQLEVLEQQSTSLGQDARRL
GGQAVGTRDQASQLLAGTEATLGHAKTLLAAIRAVDRTLSELMSQTGHLGLANASAPSGEQLLRTLAEVERLLWE
MRARDLGAPQAAAEAELAAAQRLLARVQEQLSSLWEENQALATQTRDRLAQHEAGLMDLREALNRAVDATREAQE
LNSRNQERLEEALQRKQELSRDNATLQATLHAARDTLASVFRLLHSLDQAKEELERLAASLDGARTPLLQRMQTF
SPAGSKLRLVEAAEAHAQQLGQLALNLSSIILDVNQDRLTQRAIEASNAYSRILQAVQAAEDAAGQALQQADHTW
ATVVRQGLVDRAQQLLANSTALEEAMLQEQQRLGLVWAALQGARTQLRDVRAKKDQLEAHIQAAQAMLAMDTDET
SKKIAHAKAVAAEAQDTATRVQSQLQAMQENVERWQGQYEGLRGQDLGQAVLDAGHSVSTLEKTLPQLLAKLSIL
ENRGVHNASLALSASIGRVRELIAQARGAASKVKVPMKFNGRSGVQLRTPRDLADLAAYTALKFYLQGPEPEPGQ
GTEDRFVMYMGSRQATGDYMGVSLRDKKVHWVYQLGEAGPAVLSIDEDIGEQFAAVSLDRTLQFGHMSVTVERQM
IQETKGDTVAPGAEGLLNLRPDDFVFYVGGYPSTFTPPPLLRFPGYRGCIEMDTLNEEVVSLYNFERTFQLDTAV
DRPCARSKSTGDPWLTDGSYLDGTGFARISFDSQISTTKRFEQELRLVSYSGVLFFLKQQSQFLCLAVQEGSLVL
LYDFGAGLKKAVPLQPPPPLTSASKAIQVFLLGGSRKRVLVRVERATVYSVEQDNDLELADAYYLGGVPPDQLPP
SLRRLFPTGGSVRGCVKGIKALGKYVDLKRLNTTGVSAGCTADLLVGRAMTFHGHGFLRLALSNVAPLTGNVYSG
FGFHSAQDSALLYYRASPDGLCQVSLQQGRVSLQLLRTEVKTQAGFADGAPHYVAFYSNATGVWLYVDDQLQQMK
PHRGPPPELQPQPEGPPRLLLGGLPESGTIYNFSGCISNVFVQRLLGPQRVFDLQQNLGSVNVSTGCAPALQAQT
PGLGPRGLQATARKASRRSRQPARHPACMLPPHLRTTRDSYQFGGSLSSHLEFVGILARHRNWPSLSMHVLPRSS
RGLLLFTARLRPGSPSLALFLSNGHFVAQMEGLGTRLRAQSRQRSRPGRWHKVSVRWEKNRILLVTDGARAWSQE
GPHRQHQGAEHPQPHTLFVGGLPASSHSSKLPVTVGFSGCVKRLRLHGRPLGAPTRMAGVTPCILGPLEAGLFFP
GSGGVITLDLPGATLPDVGLELEVRPLAVTGLIFHLGQARTPPYLQLQVTEKQVLLRADDGAGEFSTSVTRPSVL
CDGQWHRLAVMKSGNVLRLEVDAQSNHTVGPLLAAAAGAPAPLYLGGLPEPMAVQPWPPAYCGCMRRLAVNRSPV
AMTRSVEVHGAVGASGCPAA
```
Figure 1.

MELTSRERGRGQPLPWELRLGLLLSVLAATLAQAPAPDVPGCSRGSCYPATGDLLVGRADRLTASSTCGLNGPQP
YCIVSHLQDEKKCFLCDSRRPFSARDNPHSHRIQNVVTSFAPQRRAAWWQSENGIPAVTIQLDLEAEFHFTHLIM
TFKTFRPAAMLVERSADFGRTWHVYRYFSYDCGADFPGVPLAPPRHWDDVVCESRYSEIEPSTEGEVIYRVLDPA
IPIPDPYSSRIQNLLKITNLRVNLTRLHTLGDNLLDPRREIREKYYYALYELVVRGNCFCYGHASECAPAPGAPA
HAEGMVHGACICKHNTRGLNCEQCQDFYRDLPWRPAEDGHSHACRKCECHGHTHSCHFDMAVYLASGNVSGGVCD
GCQHNTAGRHCELCRPFFYRDPTKDLRDPAVCRSCDCDPMGSQDGGRCDSHDDPALGLVSGQCRCKEHVVGTRCQ
QCRDGFFGLSISDRLGCRRCQCNARGTVPGSTPCDPNSGSCYCKRLVTGRGCDRCLPGHWGLSHDLLGCRPCDCD
VGGALDPQCDEGTGQCHCRQHMVGRRCEQVQPGYFRPFLDHLIWEAEDTRGQVLDVVERLVTPGETPSWTGSGFV
RLQEGQTLEFLVASVPKAMDYDLLLRLEPQVPEQWAELELIVQRPGPVPAHSLCGHLVPKDDRIQGTLQPHARYL
IFPNPVCLEPGISYKLHLKLVRTGGSAQPETPYSGPGLLIDSLVLLPRVLVLEMFSGGDAAALERQATFERYQCH
EEGLVPSKTSPSEACAPLLISLSTLIYNGALPCQCNPQGSLSSECNPHGGQCLCKPGVVGRRCDLCAPGYYGFGP
TGCQACQCSHEGALSSLCEKTSGQCLCRTGAFGLRCDRCQRGQWGFPSCRPCVCNGHADECNTHTGACLGCRDHT
GGEHCERCIAGFHGDPRLPYGGQCRPCPCPEGPGSQRHFATSCHQDEYSQQIVCHCRAGYTGLRCEACAPGHFGD
PSRPGGRCQLCECSGNIDPMDPDACDPHTGQCLRCLHHTEGPHCAHCKPGFHGQAARQSCHRCTCNLLGTNPQQC
PSPDQCHCDPSSGQCPCLPNVQGPSCDRCAPNFWNLTSGHGCQPCACHPSRARGPTCNEFTGQCHCRAGFGGRTC
SECQELHWGDPGLQCHACDCDSRGIDTPQCHRFTGHCSCRPGVSGVRCDQCARGFSGIFPACHPCHACFGDWDRV
VQDLAARTQRLEQRAQELQQTGVLGAFESSFWHMQEKLGIVQGIVGARNTSAASTAQLVEATEELRREIGEATEH
LTQLEADLTDVQDENFNANHALSGLERDRLALNLTLRQLDQHLDLLKHSNFLGAYDSIRHAHSQSAEAERRANTS
ALAVPSPVSNSASARHRTEALMDAQKEDFNSKHMANQRALGKLSAHTHTLSLTDINELVCGAPGDAPCATSPCGG
AGCRDEDGQPRCGGLSCNGAAATADLALGRARHTQAELQRALAEGGSILSRVAETRRQASEAQQRAQAALDKANA
SRGQVEQANQELQELIQSVKDFLNQEGADPDSIEMVATRVLELSIPASAEQIQHLAGAIAERVRSLADVDAILAR
TVGDVRRAEQLLQDARRARSWAEDEKQKAETVQAALEEAQRAQGIAQGAIRGAVADTRDTEQTLYQVQERMAGAE
RALSSAGERARQLDALLEALKLKRAGNSLAASTAEETAGSAQGRAQEAEQLLRGPLGDQYQTVKALAERKAQGVL
AAQARAEQLRDEARDLLQAAQDKLQRLQELEGTYEENERALESKAAQLDGLEARMRSVLQAINLQVQIYNTCQKS
SWPGRAPNKPV
Figure 2.

MRGSHRAAPALRPRGRLWPVLAVLAAAAAAGCAQAAMDECTDEGGRPQRCMPEFVNAAFNVTVVATNTCGTPPEE
YCVQTGVTGVTKSCHLCDAGQPHLQHGAAFLTDYNNQADTTWWQSQTMLAGVQYPSSINLTLHLGKAFDITYVRL
KFHTSRPESFAIYKRTREDGPWIPYQYYSGSCENTYSKANRGFIRTGGDEQQALCTDEFSDISPLTGGNVAFSTL
EGRPSAYNFDNSPVLQEWVTATDIRVTLNRLNTFGDEVFNDPKVLKSYYYAISDFAVGGRCKCNGHASECMKNEF
DKLVCNCKHNTYGVDCEKCLPFFNDRPWRRATAESASECLPCDCNGRSQECYFDPELYRSTGHGGHCTNCQDNTD
GAHCERCRENFFRLGNNEACSSCHCSPVGSLSTQCDSYGRCSCKPGVMGDKCDRCQPGFHSLTEAGCRPCSCDPS
GSIDECNIETGRCVCKDNVEGFNCERCKPGFFNLESSNPRGCTPCFCFGHSSVCTNAVGYSVYSISSTFQIDEDG
WRAEQRDGSEASLEWSSERQDIAVISDSYFPRYFIAPAKFLGKQVLSYGQNLSFSFRVDRRDTRLSAEDLVLEGA
GLRVSVPLIAQGNSYPSETTVKYVFRLHEATDYPWRPALTPFEFQKLLNNLTSIKIRGTYSERSAGYLDDVTLAS
ARPGPGVPATWVESCTCPVGYGGQFCEMCLSGYRRETPNLGPYSPCVLACNGHSETCDPETGVCNCRDNTAGPH
CEKCSDGYYGDSTAGTSSDCQPCPCPGGSSCAVVPKTKEVVCTNCPTGTTGKRCELCDDGYFGDPLGRNGPVRLC
RLCQCSDNIDPNAVGNCNRLTGECLKCIYNTAGFYCDRCKDGFFGNPLAPNPADKCKACNCNLYGTMKQQSSCNP
VTGQCECLPHVTGQDCGACDPGFYNLQSGQGCERCDCHALGSTNGQCDIRTGQCECQPGITGQHCERCEVNHFGF
GPEGCKPCDCHPEGSLSLQCKDDGRCECREGFVGNRCDQCEENYFYNRSWPGCQECPACYRLVKDKVADHRVKLQ
ELESLIANLGTGDEMVTDQAFEDRLKEAEREVMDLLREAQDVKDVDQNLMDRLQRVNNTLSSQISRLQNIRNTIE
ETGNLAEQARAHVENTERLIEIASRELEKAKVAAANVSVTQPESTGDPNNMTLLAEEARKLAERHKQEADDIVRV
AKTANDTSTEAYNLLLRTLAGENQTAFEIEELNRKYEQAKNISQDLEKQAARVHEEAKRAGDKAVEIYASVAQLS
PLDSETLENEANNIKMEAENLEQLIDQKLKDYEDLREDMRGKELEVKNLLEKGKTEQQTADQLLARADAAKALAE
EAAKKGRDTLQEANDILNNLKDFDRRVNDNKTAAEEALRKIPAINQTITEANEKTREAQQALGSAAADATEAKNK
AHEAERIASAVQKNATSTKAEAERTFAEVTDLDNEVNNMLKQLQEAEKELKRKQDDADQDMMMAGMASQAAQEAE
INARKAKNSVTSLLSIINDLLEQLGQLDTVDLNKLNEIEGTLNKAKDEMKVSDLDRKVSDLENEAKKQEAAIMDY
NRDIEEIMKDIRNLEDIRKTLPSGCFNTPSIEKP
Figure 3.

MDWVIPPISCPENEKGPFPKNLVQIKSNKDKEGKVFYSITGQGADTPPVGVFIIERETGWLKVTEPLDRERIATY
TLFSHAVSSNGNAVEDPMEILITVTDQNDNKPEFTQEVFKGSVMEGALPGTSVMEVTATDADDDVNTYNAAIAYT
ILSQDPELPDKNMFTINRNTGVISVVTTGLDRESFPTYTLVVQAADLQGEGLSTTATAVITVTDTNDNPPIFNPT
TYKGQVPENEANVVITTLKVTDADAPNTPAWEAVYTILNDDGGQFVVTTNPVNNDGILKTAKGLDFEAKQQYILH
VAVTNVVPFEVSLTTSTATVTVDVLDVNEAPIFVPPEKRVEVSEDFGVGQEITSYTAQEPDTFMEQKITYRIWRD
TANWLEINPDTGAISTRAELDREDFEHVKNSTYTALIIATDNGSPVATGTGTLLLILSDVNDNAPIPEPRTIFFC
ERNPKPQVINIIDADLPPNTSPFTAELTHGASANWTIQYNDPTQESIILKPKMALEVGDYKINLKLMDNQNKDQV
TTLEVSVCDCEGAAGVCRKAQPVEAGLQIP
Figure 4.

```
CACCGCTATTGTGCGGGGGAAGATGTAGCAGCTTCTTCTCCGAACCAACCCTTTGCCTTCGGACTTCTCC
GGGGCCAGCAGCCGCCCGACCAGGGGCCCGGGGCCACGGGCTCAGCCGACGACCATGGGCTCCGTGTCCA
ACCAGCAGTTTGCAGGTGGCTGCGCCAAGGCGGCAGAAGAGGCGCCCGAGGAGGCGCCGGAGGACGCGGC
CCGGGCGGCGGACGAGCCTCAGCTGCTGCACGGTGCGGGCATCTGTAAGTGGTTCAACGTGCGCATGGGG
TTCGGCTTCCTGTCCATGACCGCCCGCGCCGGGGTCGCGCTCGACCCCCCAGTGGATGTCTTTGTGCACC
AGAGTAAGCTGCACATGGAAGGGTTCCGGAGCTTGAAGGAGGGTGAGGCAGTGGAGTTCACCTTTAAGAA
GTCAGCCAAGGGTCTGGAATCCATCCGTGTCACCGGACCTGGTGGAGTATTCTGTATTGGGAGTGAGAGG
CGGCCAAAAGGAAAGAGCATGCAGAAGCGCAGATCAAAAGGAGACAGGTGCTACAACTGTGGAGGTCTAG
ATCATCATGCCAAGGAATGCAAGCTGCCACCCCAGCCCAAGAAGTGCCACTTCTGCCAGAGCATCAGCCA
TATGGTAGCCTCATGTCCGCTGAAGGCCCAGCAGGGCCCTAGTGCACAGGGAAAGCCAACCTACTTTCGA
GAGGAAGAAGAAGAAATCCACAGCCCTACCCTGCTCCCGGAGGCACAGAATTGAGCCACAATGGGTGGGG
GCTATTCTTTTGCTATCAGGAAGTTTTGAGGAGCAGGCAGAGTGGAGAAAGTGGGAATAGGGTGCATTGG
GGCTAGTTGGCACTGCCATGTATCTCAGGCTTGGGTTCACACCATCACCCTTTCTTCCCTCTAGGTGGGG
GGAAAGGGTGAGTCAAAGGAACTCCAACCATGCTCTGTCCAAATGCAAGTGAGGGTTCTGGGGGCAACCA
GGAGGGGGGAATCACCCTACAACCTGCATACTTTGAGTCTCCATCCCCAGAATTTCCAGCTTTTGAAAGT
GGCCTGGATAGGGAAGTTGTTTTCCTTTTAAAGAAGGATATATAATAATTCCCATGCCAGAGTGAAATGA
TTAAGTATAAGACCAGATTCATGGAGCCAAGCCACTACATTCTGTGGAAGGAGATCTCTCAGGAGTAAGC
ATTGTTTTTTTTCACATCTTGTATCCTCATACCCACTTTTGGGATAGGGTGCTGGCAGCTGTCCCAAGC
AATGGGTAATGATGATGGCAAAAAGGGTGTTTGGGGGAACAGCTGCAGACCTGCTGCTCTATGCTCACCC
CCGCCCCATTCTGGGCCAATGTGATTTTATTTATTTGCTCCCTTGGATACTGCACCTTGGGTCCCACTTT
CTCCAGGATGCCAACTGCACTAGCTGTGTGCGAATGACGTATCTTGTGCATTTTAACTTTTTTTCCTTAA
TATAAATATTCTGGTTTTGTATTTTTGTATATTTTAATCTAAGGCCCTCATTTCCTGCACTGTGTTCTCA
GGTACATGAGCAATCTCAGGGATAGCCAGCAGCAGCTCCAGGTCTGCGCAGCAGGAATTACTTTTTGTTG
TTTTTGCCACCGTGGAGAGCAACTATTTGGAGTGCACAGCCTATTGAACTACCTCATTTTTGCCAATAAG
AGCTGGCTTTTCTGCCATAGTGTCCTCTTGAAACCCCCTCTGCCTTGAAAATGTTTTATGGGAGACTAGG
TTTTAACTGGGTGGCCCCATGACTTGATTGCCTTCTACTGGAAGATTGGGAATTAGTCTAAACAGGAAAT
GGTGGTACACAGAGGCTAGGAGAGGCTGGGCCCGGTGAAAAGGCCAGAGAGCAAGCCAAGATTAGGTGAG
GGTTGTCTAATCCTATGGCACAGGACGTGCTTTACATCTCCAGATCTGTTCTTCACCAGATTAGGTTAGG
CCTACCATGTGCCACAGGGTGTGTGTGTGTTTGTAAAACTAGAGTTGCTAAGGATAAGTTTAAAGACCAA
TACCCCTGTACTTAATCCTGTGCTGTCGAGGGATGGATATATGAAGTAAGGTGAGATCCTTAACCTTTCA
AAATTTTCGGGTTCCAGGGAGACACACAAGCGAGGGTTTTGTGGTGCCTGGAGCCTGTGTCCTGCCCTGC
TACAGTAGTGATTAATAGTGTCATGGTAGCTAAAGGAGAAAAAGGGGGTTTCGTTTACACGCTGTGAGAT
CACCGCAAACCTACCTTACTGTGTTGAAACGGGACAAATGCAATAGAACGCATTGGGTGGTGTGTCTG
ATCCTGGGTTCTTGTCTCCCCTAAATGCTGCCCCCAAGTTACTGTATTTGTCTGGGCTTTGTAGGACTT
CACTACGTTGATTGCTAGGTGGCCTAGTTTGTGTAAATATAATGTATTGGTCTTTCTCCGTGTTCTTTGG
GGGTTTTGTTTACAAACTTCTTTTTGTATTGAGAGAAAAATAGCCAAAGCATCTTTGACAGAAGGTTCTG
CACCAGGCAAAAAGATCTGAAACATTAGTTTGGGGGGCCCTCTTCTTAAAGTGGGGATCTTGAACCATCC
TTTCTTTTGTATTCCCCTTCCCCTATTACCTATTAGACCAGATCTTCTGTCCTAAAAACTTGTCTTCTAC
CCTGCCCTCTTTTCTGTTCACCCCCAAAAGAAAACTTACACACCCACACACATACACATTTCATGCTTGG
AGTGTCTCCACAACTCTTAAATGATGTATGCAAAAATACTGAAGCTAGGAAAACCCTCCATCCCTTGTTC
CCAACCTCCTAAGTCAAGACCATTACCATTTCTTTCTTTCTTTTTTTTTTTTTTTTAAAATGGAGTCTCA
CTGTGTCACCCAGGCTGGAGTGCAGTGGCATGATCGGCTCACTGCAGCCTCTGCCTCTTGGGTTCAAGTG
ATTCTCCTGCCTCAGCCTCCTGAGTAGCTGGGATTTCAGGCACCCGCCACACTCAGCTAATTTTTGTATT
TTTAGTAGAGACGGGGTTTCACCATGTTGTCCAGGCTGGTCTGGAACTCCTGACCTCAGGTGATCTGCCC
ACCTTGGCTTCCCAAAGTGCTGGGATTACAGGCATGAGCCACCATGCTGGGCCAACCATTTCTTGGTGTA
TTCATGCCAAACACTTAAGACACTGCTGTAGCCCAGGCGCGGTGGCTCACACCTGTAATCCCAGCACTTT
GGAAGGCTGAGGCGGGCGGATCACAAGGTCACGAGTTCAAAACTATCCTGGCCAACACAGTGAAACCCCG
TCTCTACTAAAATACAAAAAATTAGCCGGGTGTGGTGGTGCATGCCTTTAGTCCTAGCTATTCAGGAGG
CTGAGGCAGGGGAATCGCTTGAACCCGAGAGGCAGAGGTTGCAGTGAGCTGAGATCGCACCACTGCACTC
CAGCCTGGTTACAGAGCAAGACTCTGTCTCAAACAAAACAAAACAAAACAAAAACACACTACTGTATTTT
GGATGGATCAAACCTCCTTAATTTTAATTTCTAATCCTAAAGTAAAGAGATGCAATTGGGGGCCTTCCAT
GTAGAAAGTGGGGTCAGGAGGCCAAGAAAGGGAATATGAATGTATATCCAAGTCACTCAGGAACTTTTAT
GCAGGTGCTAGAAACTTTATGTCAAAGTGGCCACAAGATTGTTTAATAGGAGACGAACGAATGTAACTCC
ATGTTTACTGCTAAAAACCAAAGCTTTGTGTAAAATCTTGAATTTATGGGCGGGAGGGTAGGAAAGCCT
GTACCTGTCTGTTTTTTTCCTGATCCTTTTCCCTCATTCCTGAACTGCAGGAGACTGAGCCCCTTTGGGC
TTTGGTGACCCCATCACTGGGGTGTGTTTATTTGATGGTTGATTTTGCTGTACTGGGTACTTCCTTTCCC
ATTTTCTAATCATTTTTTAACACAAGCTGACTCTTCCCTTCCCTTCTCCTTTCCCTGGGAAAATACAATG
AATAAATAAAGACTTATTGGTACGCAAACTGTCA
```

Figure 5.

```
AGAGAGGGGTTGAGTAGTCCCTTCGCAAGCCCTCATTTCACCAGGCCCCCGGCTTGGGGCGCCTTCCTTC
CCCATGGCGGGACACCTGGCTTCGGATTTCGCCTTCTCGCCCCCTCCAGGTGGTGGAGGTGATGGGCCAG
GGGGGCCGGAGCCGGGCTGGGTTGATCCTCGGACCTGGCTAAGCTTCCAAGGCCCTCCTGGAGGGCCAGG
AATCGGGCCGGGGGTTGGGCCAGGCTCTGAGGTGTGGGGGATTCCCCCATGCCCCCCGCCGTATGAGTTC
TGTGGGGGGATGGCGTACTGTGGGCCCCAGGTTGGAGTGGGGCTAGTGCCCCAAGGCGGCTTGGAGACCT
CTCAGCCTGAGGGCGAAGCAGGAGTCGGGGTGGAGAGCAACTCCGATGGGGCCTCCCCGGAGCCCTGCAC
CGTCACCCCTGGTGCCGTGAAGCTGGAGAAGGAGAAGCTGGAGCAAAACCCGGAGGAGTCCCAGGACATC
AAAGCTCTGCAGAAAGAACTCGAGCAATTTGCCAAGCTCCTGAAGCAGAAGAGGATCACCCTGGGATATA
CACAGGCCGATGTGGGGCTCACCCTGGGGGTTCTATTTGGGAAGGTATTCAGCCAAACGACCATCTGCCG
CTTTGAGGCTCTGCAGCTTAGCTTCAAGAACATGTGTAAGCTGCGGCCCTTGCTGCAGAAGTGGGTGGAG
GAAGCTGACAACAATGAAAATCTTCAGGAGATATGCAAAGCAGAAACCCTCGTGCAGGCCCGAAAGAGAA
AGCGAACCAGTATCGAGAACCGAGTGAGAGGCAACCTGGAGAATTTGTTCCTGCAGTGCCCGAAACCCAC
ACTGCAGCAGATCAGCCACATCGCCCAGCAGCTTGGGCTCGAGAAGGATGTGGTCCGAGTGTGGTTCTGT
AACCGGCGCCAGAAGGGCAAGCGATCAAGCAGCGACTATGCACAACGAGAGGATTTTGAGGCTGCTGGGT
CTCCTTTCTCAGGGGGACCAGTGTCCTTTCCTCTGGCCCCAGGGCCCCATTTTGGTACCCCAGGCTATGG
GAGCCCTCACTTCACTGCACTGTACTCCTCGGTCCCTTTCCCTGAGGGGGAAGCCTTTCCCCCTGTCTCC
GTCACCACTCTGGGCTCTCCCATGCATTCAAACTGAGGTGCCTGCCCTTCTAGGAATGGGGGACAGGGGG
AGGGGAGGAGCTAGGGAAAGAAAACCTGGAGTTTGTGCCAGGGTTTTTGGGATTAAGTTCTTCATTCACT
AAGGAAGGAATTGGGAACACAAAGGGTGGGGGCAGGGGAGTTTGGGGCAACTGGTTGGAGGGAAGGTGAA
GTTCAATGATGCTCTTGATTTTAATCCCACATCATGTATCACTTTTTTCTTAAATAAAGAAGCCTGGGAC
ACAGTAGATAGACACACTTAAAAAAAAAAA
```
Figure 6.

```
GGATGGTTGTCTATTAACTTGTTCAAAAAAGTATCAGGAGTTGTCAAGGCAGAGAAGAGAGTGTTTGCAA
AAGGGGGAAAGTAGTTTGCTGCCTCTTTAAGACTAGGACTGAGAGAAAGAAGAGGAGAGAGAAAGAAAGG
GAGAGAAGTTTGAGCCCCAGGCTTAAGCCTTTCCAAAAAATAATAATAACAATCATCGGCGGCGGCAGGA
TCGGCCAGAGGAGGAGGGAAGCGCTTTTTTTGATCCTGATTCCAGTTTGCCTCTCTCTTTTTTTCCCCCA
AATTATTCTTCGCCTGATTTTCCTCGCGGAGCCCTGCGCTCCCGACACCCCCGCCCGCCTCCCCTCCTCC
TCTCCCCCCGCCCGCGGGCCCCCCAAAGTCCCGGCCGGGCCGAGGGTCGGCGGCCGCCGGCGGGCCGGGC
CCGCGCACAGCGCCCGCATGTACAACATGATGGAGACGGAGCTGAAGCCGCCGGGCCCGCAGCAAACTTC
GGGGGGCGGCGGCGGCAACTCCACCGCGGCGGCGGCCGGCGGCAACCAGAAAAACAGCCCGGACCGCGTC
AAGCGGCCCATGAATGCCTTCATGGTGTGGTCCCGCGGGCAGCGGCGCAAGATGGCCCAGGAGAACCCCA
AGATGCACAACTCGGAGATCAGCAAGCGCCTGGGCGCCGAGTGGAAACTTTTGTCGGAGACGGAGAAGCG
GCCGTTCATCGACGAGGCTAAGCGGCTGCGAGCGCTGCACATGAAGGAGCACCCGGATTATAAATACCGG
CCCCGGCGGAAAACCAAGACGCTCATGAAGAAGGATAAGTACACGCTGCCCGGCGGGCTGCTGGCCCCCG
GCGGCAATAGCATGGCGAGCGGGGTCGGGGTGGGCGCCGGCCTGGGCGCGGGCGTGAACCAGCGCATGGA
CAGTTACGCGCACATGAACGGCTGGAGCAACGGCAGCTACAGCATGATGCAGGACCAGCTGGGCTACCCG
CAGCACCCGGGCCTCAATGCGCACGGCGCAGCGCAGATGCAGCCCATGCACCGCTACGACGTGAGCGCCC
TGCAGTACAACTCCATGACCAGCTCGCAGACCTACATGAACGGCTCGCCCACCTACAGCATGTCCTACTC
GCAGCAGGGCACCCCTGGCATGGCTCTTGGCTCCATGGGTTCGGTGGTCAAGTCCGAGGCCAGCTCCAGC
CCCCCTGTGGTTACCTCTTCCTCCCACTCCAGGGCGCCCTGCCAGGCCGGGGACCTCCGGGACATGATCA
GCATGTATCTCCCCGGCGCCGAGGTGCCGGAACCCGCCGCCCCAGCAGACTTCACATGTCCCAGCACTA
CCAGAGCGGCCCGGTGCCCGGCACGGCCATTAACGGCACACTGCCCCTCTCACACATGTGAGGGCCGGAC
AGCGAACTGGAGGGGGAGAAATTTTCAAAGAAAAACGAGGGAAATGGGAGGGGTGCAAAAGAGGAGAGT
AAGAAACAGCATGGAGAAAACCCGGTACGCTCAAAAAGAAAAAGGAAAAAAAAAAATCCCATCACCCACA
GCAAATGACAGCTGCAAAAGAGAACACCAATCCCATCCACACTCACGCAAAAACCGCGATGCCGACAAGA
AAACTTTTATGAGAGAGATCCTGGACTTCTTTTTGGGGGACTATTTTTGTACAGAGAAAACCTGGGGAGG
GTGGGGAGGGCGGGGGAATGGACCTTGTATAGATCTGGAGGAAAGAAAGCTACGAAAAACTTTTTAAAAG
TTCTAGTGGTACGGTAGGAGCTTTGCAGGAAGTTTGCAAAAGTCTTTACCAATAATATTTAGAGCTAGTC
TCCAAGCGACGAAAAAAATGTTTTAATATTTGCAAGCAACTTTTGTACAGTATTTATCGAGATAAACATG
GCAATCAAAATGTCCATTGTTTATAAGCTGAGAATTTGCCAATATTTTTCAAGGAGAGGCTTCTTGCTGA
ATTTTGATTCTGCAGCTGAAATTTAGGACAGTTGCAAACGTGAAAAGAAGAAAATTATTCAAATTTGGAC
ATTTTAATTGTTTAAAAATTGTACAAAAGGAAAAAATTAGAATAAGTACTGGCGAACCATCTCTGTGGTC
TTGTTTAAAAAGGGCAAAAGTTTTAGACTGTACTAAATTTTATAACTTACTGTTAAAAGCAAAAATGGCC
ATGCAGGTTGACACCGTTGGTAATTTATAATAGCTTTTGTTCGATCCCAACTTTCCATTTTGTTCAGATA
AAAAAAACCATGAAATTACTGTGTTTGAAATATTTTCTTATGGTTTGTAATATTTCTGTAAATTTATTGT
GATATTTTAAGGTTTTCCCCCCTTTATTTTCCGTAGTTGTATTTTAAAAGATTCGGCTCTGTATTATTTG
AATCAGTCTGCCGAGAATCCATGTATATATTTGAACTAATATCATCCTTATAACAGGTACATTTTCAACT
TAAGTTTTTACTCCATTATGCACAGTTTGAGATAAATAAATTTTTGAAATATGGACACTGAAAAAAAAAA
```
Figure 7.

```
ATGACCCTCTCCGGCGGCGGCAGCGCCAGCGACATGTCCGGCCAGACGGTGCTGACGGCCGAGGACGTGG
ACATCGATGTGGTGGGCGAGGGCGACGACGGGCTGGAAGAGAAGGACAGCGACGCAGGTTGCGATAGCCC
CGCGGGGCCGCCGGAGCTGCGCCTGGACGAGGCGGACGAGGTGCCCCCGGCGGCACCCCATCACGGACAG
CCTCAGCCGCCCCACCAGCAGCCCCTGACATTGCCCAAGGAGGCGGCCGGAGCCGGGGCCGGACCGGGGG
GCGACGTGGGCGCGCCGGAGGCGGACGGCTGCAAGGGCGGTGTTGGCGGCGAGGAGGCGGCGCGAGCGG
CGGCGGGCCTGGCGCGGGCAGCGGTTCGGCGGGAGGCCTGGCCCCGAGCAAGCCCAAGAACAGCCTAGTG
AAGCCGCCTTACTCGTACATCGCGCTCATCACCATGGCCATCCTGCAGAGCCCGCAGAAGAAGCTGACCC
TGAGCGGCATCTGCGAGTTCATCAGCAACCGCTTCCCCTACTACAGGGAGAAGTTCCCCGCCTGGCAGAA
CAGCATCCGCCACAACCTCTCACTCAACGACTGCTTCGTCAAGATCCCCCGCGAGCCGGGCAACCCGGGC
AAGGGCAACTACTGGACCCTGGACCCGCAGTCCGAGGACATGTTCGACAACGGCAGCTTCCTGCGGCGCC
GGAAACGCTTCAAGCGCCACCAGCAGGAGCACCTGCGCGAGCAGACGGCGCTCATGATGCAGAGCTTCGG
CGCTTACAGCCTGGCGGCGGCGGCCGGCGCCGCGGGACCCTACGGCCGCCCCTACGGCCTGCACCCTGCG
GCGGCGGCCGGTGCCTATTCGCACCCGGCAGCGGCGGCGGCCGCGGCTGCTGCGGCGGCGCTCCAGTACC
CGTACGCGCTGCCGCCGGTGGCACCGGTGCTGCCTCCCGCTGTGCCGCTGCTGCCCTCGGGCGAGCTGGG
CCGCAAAGCGGCCGCCTTCGGCTCACAGCTCGGCCCGGGCCTGCAGCTGCAGCTCAATAGCCTGGGCGCC
GCCGCGGCCGCTGCGGGCACAGCGGGCGCCGCGGGCACCACCGCGTCGCTCATCAAGTCCGAGCCAAGCG
CGCGGCCGTCGTTCAGCATCGAGAACATCATAGGTGGGGGCCCCGCGGCTCCTGGGGGCTCGGCGGTGGG
CGCTGGGGTCGCCGGCGGCACTGGGGGTTCAGGGGGCGGCAGCACGGCGCAGTCGTTTCTGCGGCCACCC
GGGACCGTGCAGTCGGCAGCGCTCATGGCCACCCACCAACCGCTGTCGCTGAGCCGGACGACTGCCACCA
TCGCGCCCATTCTTAGCGTGCCACTCTCCGGACAGTTTCTGCAGCCCGCAGCCTCGGCCGCCGCCGCTGC
TGCGGCCGCCGCTCAAGCCAAATGGCCGGCGCAATAGGGACGCGCCAATGGCCGGGACCCAGGGTCCGGC
GGCGGCCTCGAGCAACAAATGCACCTCCAGGCTGCGCGCCCTGTCCCAAGCCCGGTCCCGGTCCCGCTGC
CCAATCCTGGACTCTGCCTCTCCCCAATTTCCTTTCCCCTGAGCCCCCAACGCCTACCTTCCGCGGCCTC
CATCCCCTCGCGCACACCTAAGCTGGTCGAGCAAACTCACCGCGCGCCCGCCGGGGATAGCTTTCCATAC
AGGTAAAACCGAAAACCGAATTTTCCAAAAATGCACCCCGACGGCGCCTGCTCTTAGTACCGTGGGGATG
GGAGGGAAATTCTTTGTATATATTTGTAAAAAAATTATTGACTTTCCTTTTGGGGTTTTTATTTTTTTAA
GAAAAAACAAATTCCGTAGATTTAGAGCTCTGAACTTTCATTTTTTTTGAAGGTTCACTCTCCGAAGTTT
TATCTGAGAAAAGAATGTATAGAGACGTTGGGAGATTTTAAATATAAAAAATTTTCAAAAAGGCAAAAAG
TGTCATTCTATTATAAAAGTCTGTTTATATATGAATGAATATATATGGTATTCTAAATGTTATTCCATCG
TGTTGTACACAACTTTGTAAATAAATTTTTAAAATGCCAAAAAAAAAA
```
Figure 8.

```
TTCATTATAAATCTAGAGACTCCAGGATTTTAACGTTCTGCTGGACTGAGCTGGTTGCCTCATGTTATTA
TGCAGGCAACTCACTTTATCCCAATTTCTTGATACTTTTCCTTCTGGAGGTCCTATTTCTCTAACATCTT
CCAGAAAAGTCTTAAAGCTGCCTTAACCTTTTTTCCAGTCCACCTCTTAAATTTTTTCCTCCTCTTCCTC
TATACTAACATGAGTGTGGATCCAGCTTGTCCCCAAAGCTTGCCTTGCTTTGAAGCATCCGACTGTAAAG
AATCTTCACCTATGCCTGTGATTTGTGGCCTGAAGAAAACTATCCATCCTTGCAAATGTCTTCTGCTGA
GATGCCTCACACGGAGACTGTCTCTCCTCTTCCTTCCTCCATGGATCTGCTTATTCAGGACAGCCCTGAT
TCTTCCACCAGTCCCAAAGGCAAACAACCCACTTCTGCAGAGAAGAGTGTCGCAAAAAAGGAAGACAAGG
TCCCGGTCAAGAAACAGAAGACCAGAACTGTGTTCTCTTCCACCCAGCTGTGTGTACTCAATGATAGATT
TCAGAGACAGAAATACCTCAGCCTCCAGCAGATGCAAGAACTCTCCAACATCCTGAACCTCAGCTACAAA
CAGGTGAAGACCTGGTTCCAGAACCAGAGAATGAAATCTAAGAGGTGGCAGAAAAACAACTGGCCGAAGA
ATAGCAATGGTGTGACGCAGAAGGCCTCAGCACCTACCTACCCCAGCCTTTACTCTTCCTACCACCAGGG
ATGCCTGGTGAACCCGACTGGGAACCTTCCAATGTGGAGCAACCAGACCTGGAACAATTCAACCTGGAGC
AACCAGACCCAGAACATCCAGTCCTGGAGCAACCACTCCTGGAACACTCAGACCTGGTGCACCCAATCCT
GGAACAATCAGGCCTGGAACAGTCCCTTCTATAACTGTGGAGAGGAATCTCTGCAGTCCTGCATGCAGTT
CCAGCCAAATTCTCCTGCCAGTGACTTGGAGGCTGCCTTGGAAGCTGCTGGGGAAGGCCTTAATGTAATA
```
Figure 9.

```
CAGCAGACCACTAGGTATTTTAGTACTCCACAAACCATGGATTTATTCCTAAACTACTCCATGAACATGC
AACCTGAAGACGTGTGAAGATGAGTGAAACTGATATTACTCAATTTCAGTCTGGACACTGGCTGAATCCT
TCCTCTCCCCTCCTCCCATCCCTCATAGGATTTTTCTTGTTTGGAAACCACGTGTTCTGGTTTCCATGAT
GCCCATCCAGTCAATCTCATGGAGGGTGGAGTATGGTTGGAGCCTAATCAGCGAGGTTTCTTTTTTTTTT
TTTTTCCTATTGGATCTTCCTGGAGAAAATACTTTTTTTTTTTTTTTTTTGAAACGGAGTCTTGCTCTG
TCGCCCAGGCTGGAGTGCAGTGGCGCGGTCTTGGCTCACTGCAAGCTCCGTCTCCCGGGTTCACGCCATT
CTCCTGCCTCAGCCTCCCGAGCAGCTGGGACTACAGGCGCCCGCCACCTCGCCCGGCTAATATTTTGTAT
TTTTAGTAGAGACGGGGTTTCACTGTGTTAGCCAGGATGGTCTCGATCTCCTGACCTTGTGATCCACCCG
CCTCGGCCTCCCTAACAGCTGGGATTTACAGGCGTGAGCCACCGCGCCCTGCCTAGAAAAGACATTTTAA
TAACCTTGGCTGCCGTCTCTGGCTATAGATAAGTAGATCTAATACTAGTTTGGATATCTTTAGGGTTTAG
AATCTAACCTCAAGAATAAGAAATACAAGTACAAATTGGTGATGAAGATGTATTCGTATTGTTTGGGATT
GGGAGGCTTTGCTTATTTTTAAAAACTATTGAGGTAAAGGGTTAAGCTGTAACATACTTAATTGATTTC
TTACCGTTTTTGGCTCTGTTTTGCTATATCCCCTAATTTGTTGGTTGTGCTAATCTTTGTAGAAAGAGGT
CTCGTATTTGCTGCATCGTAATGACATGAGTACTGCTTTAGTTGGTTTAAGTTCAAATGAATGAAACAAC
TATTTTTCCTTTAGTTGATTTTACCCTGATTTCACCGAGTGTTTCAATGAGTAAATATACAGCTTAAACA
TAA
```
Figure 9 (continued).

```
AGCCGCGCAGACGCCGCCCAGGACGCAGCCGCCGCCGCCGCCGCTCCTCTGCCACTGGCTCTGCGCCCCA
GCCCGGCTCTGCTGCAGCGGCAGGGAGGAAGAGCCGCCGCAGCGCGACTCGGGAGCCCCGGGCCACAGCC
TGGCCTCCGGAGCCACCCACAGGCCTCCCCGGGCGGCGCCCACGCTCCTACCGCCCGGACGCGCGGATCC
TCCGCCGGCACCGCAGCCACCTGCTCCCGGCCCAGAGGCGACGACACGATGCGCTGCGCGCTGGCGCTCT
CGGCGCTGCTGCTACTGTTGTCAACGCCGCCGCTGCTGCCGTCGTCGCCGTCGCCGTCGCCGTCGCCCTC
CCAGAATGCAACCCAGACTACTACGGACTCATCTAACAAAACAGCACCGACTCCAGCATCCAGTGTCACC
ATCATGGCTACAGATACAGCCCAGCAGAGCACAGTCCCCACTTCCAAGGCCAACGAAATCTTGGCCTCGG
TCAAGGCGACCACCCTTGGTGTATCCAGTGACTCACCGGGGACTACAACCCTGGCTCAGCAAGTCTCAGG
CCCAGTCAACACTACCGTGGCTAGAGGAGGCGGCTCAGGCAACCCTACTACCACCATCGAGAGCCCCAAG
AGCACAAAAAGTGCAGACACCACTACAGTTGCAACCTCCACAGCCACAGCTAAACCTAACACCACAAGCA
GCCAGAATGGAGCAGAAGATACAACAAACTCTGGGGGGAAAAGCAGCCACAGTGTGACCACAGACCTCAC
ATCCACTAAGGCAGAACATCTGACGACCCCTCACCCTACAAGTCCACTTAGCCCCCGACAACCCACTTCG
ACGCATCCTGTGGCCACCCCAACAAGCTCGGGACATGACCATCTTATGAAAATTTCAAGCAGTTCAAGCA
CTGTGGCTATCCCTGGCTACACCTTCACAAGCCCGGGGATGACCACCACCCTACTAGAGACAGTGTTTCA
CCATGTCAGCCAGGCTGGTCTTGAACTCCTGACCTCGGGTGATCTGCCCACCTTGGCCTCCCAAAGTGCT
GGGATTACAGCGTCATCGGTTATCTCGCAAAGAACTCAACAGACCTCCAGTCAGATGCCAGCCAGCTCTA
CGGCCCCTTCCTCCCAGGAGACAGTGCAGCCCACGAGCCCGGCAACGGCATTGAGAACACCTACCCTGCC
AGAGACCATGAGCTCCAGCCCCACAGCAGCATCAACTACCCACCGATACCCCAAAACACCTTCTCCCACT
GTGGCTCATGAGAGTAACTGGGCAAAGTGTGAGGATCTTGAGACACAGACACAGAGTGAGAAGCAGCTCG
TCCTGAACCTCACAGGAAACACCCTCTGTGCAGGGGGCGCTTCGGATGAGAAATTGATCTCACTGATATG
CCGAGCAGTCAAAGCCACCTTCAACCCGGCCCAAGATAAGTGCGGCATACGGCTGGCATCTGTTCCAGGA
AGTCAGACCGTGGTCGTCAAAGAAATCACTATTCACACTAAGCTCCCTGCCAAGGATGTGTACGAGCGGC
TGAAGGACAAATGGGATGAACTAAAGGAGGCAGGGGTCAGTGACATGAAGCTAGGGGACCAGGGGCCACC
GGAGGAGGCCGAGGACCGCTTCAGCATGCCCCTCATCATCACCATCGTCTGCATGGCATCATTCCTGCTC
CTCGTGGCGGCCCTCTATGGCTGCTGCCACCAGCGCCTCTCCCAGAGGAAGGACCAGCAGCGGCTAACAG
AGGAGCTGCAGACAGTGGAGAATGGTTACCATGACAACCCAACACTGGAAGTGATGGAGACCTCTTCTGA
GATGCAGGAGAAGAAGGTGGTCAGCCTCAACGGGGAGCTGGGGGACAGCTGGATCGTCCCTCTGGACAAC
CTGACCAAGGACGACCTGGATGAGGAGGAAGACACACACCTCTAGTCCGGTCTGCCGGTGGCCTCCAGCA
GCACCACAGAGCTCCAGACCAACCACCCCAAGTGCCGTTTGGATGGGGAAGGGAAAGACTGGGGAGGGAG
AGTGAACTCCGAGGGGTGTCCCCTCCCAATCCCCCCAGGGCCTTAATTTTTCCCTTTTCAACCTGAACAA
ATCACATTCTGTCCAGATTCCTCTTGTAAAATAACCCACTAGTGCCTGAGCTCAGTGCTGCTGGATGATG
AGGGAGATCAAGAAAAAGCCACGTAAGGGACTTTATAGATGAACTAGTGGAATCCCTTCATTCTGCAGTG
AGATTGCCGAGACCTGAAGAGGGTAAGTGACTTGCCCAAGGTCAGAGCCACTTGGTGACAGAGCCAGGAT
GAGAACAAAGATTCCATTTGCACCATGCCACACTGCTGTGTTCACATGTGCCTTCCGTCCAGAGCAGTCC
CGGGCAGGGGTGAAACTCCAGCAGGTGGCTGGGCTGGAAAGGAGGGCAGGGCTACATCCTGGCTCGGTGG
GATCTGACGACCTGAAAGTCCAGCTCCCAAGTTTTCCTTCTCCTACCCCAGCCTCGTGTACCCATCTTCC
CACCCTCTATGTTCTTACCCCTCCCTACACTCAGTGTTTGTTCCCACTTACTCTGTCCTGGGGCCTCTGG
GATTAGCACAGGTTATTCATAACCTTGAACCCCTTGTTCTGGATTCGGATTTTCTCACATTTGCTTCGTG
AGATGGGGCTTAACCCACACAGGTCTCCGTGCGTGAACCAGGTCTGCTTAGGGGACCTGCGTGCAGGTG
AGGAGAGAAGGGGACACTCGAGTCCAGGCTGGTATCTCAGGGCAGCTGATGAGGGGTCAGCAGGAACACT
GGCCCATTGCCCCTGGCACTCCTTGCAGAGGCCACCCACGATCTTCTTTGGGCTTCCATTTCCACCAGGG
```
Figure 10.

```
ACTAAAATCTGCTGTAGCTAGTGAGAGCAGCGTGTTCCTTTTGTTGTTCACTGCTCAGCTGATGGGAGTG
ATTCCCTGAGACCCAGTATGAAAGAGCAGTGGCTGCAGGAGAGGCCTTCCCGGGGCCCCCCATCAGCGAT
GTGTCTTCAGAGACAATCCATTAAAGCAGCCAGGAAGGACAGGCTTTCCCCTGTATATCATAGGAAACTC
AGGGACATTTCAAGTTGCTGAGAGTTTTGTTATAGTTGTTTTCTAACCCAGCCCTCCACTGCCAAAGGCC
AAAAGCTCAGACAGTTGGCAGACGTCCAGTTAGCTCATCTCACTCACTCTGATTCTCCTGTGCCACAGGA
AAAGAGGGCCTGGAAAGCGCAGTGCATGCTGGGTGCATGAAGGGCAGCCTGGGGGACAGACTGTTGTGGG
AACGTCCCACTGTCCTGGCCTGGAGCTAGGCCTTGCTGTTCCTCTTCTCTGTGAGCCTAGTGGGGCTGCT
GCGGTTCTCTTGCAGTTTCTGGTGGCATCTCAGGGGAACACAAAGCTATGTCTATTCCCCAATATAGGAC
TTTTATGGGCTCGGCAGTTAGCTGCCATGTAGAAGGCTCCTAAGCAGTGGGCATGGTGAGGTTTCATCTG
ATTGAGAAGGGGGAATCCTGTGTGGAATGTTGAACTTTCGCCATGGTCTCCATCGTTCTGGGCGTAAATT
CCCTGGGATCAAGTAGGAAAATGGGCAGAACTGCTTAGGGGAATGAAATTGCCATTTTTCGGGTGAAACG
CCACACCTCCAGGGTCTTAAGAGTCAGGCTCCGGCTGTAGTAGCTCTGATGAAATAGGCTATCCACTCGG
GATGGCTTACTTTTTAAAAGGGTAGGGGAGGGGCTGGGGAAGATCTGTCCTGCACCATCTGCCTAATTC
CTTCCTCACAGTCTGTAGCCATCTGATATCCTAGGGGAAAAGGAAGGCCAGGGGTTCACATAGGGCCCCA
GCGAGTTTCCCAGGAGTTAGAGGGATGCGAGGCTAACAAGTTCCAAAAACATCTGCCCCGATGCTCTAGT
GTTTGGAGGTGGGCAGGATGGAGAACAGTGCCTGTTTGGGGGAAAACAGGAAATCTTGTTAGGCTTGAGT
GAGGTGTTTGCTTCCTTCTTGCCCAGCGCTGGGTTCTCTCCACCCAGTAGGTTTTCTGTTGTGGTCCCGT
GGGAGAGGCCAGACTGGATTATTCCTCCTTTGCTGATCCTGGGTCACACTTCACCAGCCAGGGCTTTTGA
CGGAGACAGCAAATAGGCCTCTGCAAATCAATCAAAGGCTGCAACCCTATGGCCTCTTGGAGACAGATGA
TGACTGGCAAGGACTAGAGAGCAGGAGTGCCTGGCCAGGTCGGTCCTGACTCTCCTGACTCTCCATCGCT
CTGTCCAAGGAGAACCCGGAGAGGCTCTGGGCTGATTCAGAGGTTACTGCTTTATATTCGTCCAAACTGT
GTTAGTCTAGGCTTAGGACAGCTTCAGAATCTGACACCTTGCCTTGCTCTTGCCACCAGGACACCTATGT
CAACAGGCCAAACAGCCATGCATCTATAAAGGTCATCATCTTCTGCCACCTTTACTGGGTTCTAAATGCT
CTCTGATAATTCAGAGAGCATTGGGTCTGGGAAGAGGTAAGAGGAACACTAGAAGCTCAGCATGACTTAA
ACAGGTTGTAGCAAAGACAGTTTATCATCAGCTCTTTCAGTGGTAAACTGTGGTTTCCCCAAGCTGCACA
GGAGGCCAGAAACCACAAGTATGATGACTAGGAAGCCTACTGTCATGAGAGTGGGGAGACAGGCAGCAAA
GCTTATGAAGGAGGTACAGAATATTCTTTGCGTTGTAAGACAGAATACGGGTTTAATCTAGTCTAGGCAC
CAGATTTTTTTCCCGCTTGATAAGGAAAGCTAGCAGAAAGTTTATTTAAACCACTTCTTGAGCTTTATCT
TTTTTGACAATATACTGGAGAAACTTTGAAGAACAAGTTCAAACTGATACATATACACATATTTTTTGA
TAATGTAAATACAGTGACCATGTTAACCTACCCTGCACTGCTTTAAGTGAACATACTTTGAAAAAGCATT
ATGTTAGCTGAGTGATGGCCAAGTTTTTTCTCTGGACAGGAATGTAAATGTCTTACTGGAAATGACAAGT
TTTTGCTTGATTTTTTTTTTAAACAAAAAATGAAATATAACAAGACAAACTTATGATAAAGTATTTGTC
TTGTAGATCAGGTGTTTTGTTTTGTTTTTTAATTTTAAAATGCAACCCTGCCCCCTCCCCAGCAAAGTC
ACAGCTCCATTTCAGTAAAGGTTGGAGTCAATATGCTCTGGTTGGCAGGCAACCCTGTAGTCATGGAGAA
AGGTATTTCAAGATCTAGTCCAATCTTTTTCTAGAGAAAAGATAATCTGAAGCTCACAAAGATGAAGTG
ACTTCCTCAAAATCACATGGTTCAGGACAGAAACAAGATTAAAACCTGGATCCACAGACTGTGCGCCTCA
GAAGGAATAATCGGTAAATTAAGAATTGCTACTCGAAGGTGCCAGAATGACACAAAGGACAGAATTCCTT
TCCCAGTTGTTACCCTAGCAAGGCTAGGGAGGGCATGAACACAAACATAAGAACTGGTCTTCTACACTTT
CTCTGAATCATTTAGGTTTAAGATGTAAGTGAACAATTCTTTCTTTCTGCCAAGAAACAAAGTTTTGGAT
GAGCTTTTATATATGGAACTTACTCCAACAGGACTGAGGGACCAAGGAAACATGATGGGGGAGGCAGAGA
GGGCAAGAGTAAAACTGTAGCATAGCTTTTGTCACGGTCACTAGCTGATCCCTCAGGTCTGCTGCAAACA
CAGCATGGAGGACACAGATGACTCTTTGGTGTTGGTCTTTTGTCTGCAGTGAATGTTCAACAGTTTGCC
CAGGAACTGGGGGATCATATATGTCTTAGTGGACAGGGGTCTGAAGTACACTGGAATTTACTGAGAAACT
TGTTTGTAAAAACTATAGTTAATAATTATTGCATTTTCTTACAAAAATATATTTTGGAAAATTGTATACT
GTCAATTAAAGTGTTTTTGTGTAAACTGGTTCAAAAAAAAAAAAAAAAAAAAAAAA
```

Figure 10 (continued).

```
AGTTTCTCCTTTGTTTTACGTTTGGGAGGAGGTGGCATTGGAAATAGCAGAGTGCTTCGCGGTAACAGGG
GTTGGAGTGCAATGGTGTGATCTCAGCTCACTGCAACCCCTGCCTCCCAGGCTCCAGCGATCCTCCCACC
TCAGCCTCCTGAATAGCTGACCACCAGCACACTAGGCAAACCCACCCCACTCACGGCCTCCCTTGGGAAT
TCAGACCTAACCATCGCTGAGCTGAAACAAATGTACTGAGGCTGGAGCCTGTGTGAACAGAACAGAAGAG
GCCTTCACTCTAGTAGTGCTCACAGTCCAGCAGGTGTTTGCTGAAGACAGCTTACTCAGATCACTACTGC
CTGGAGGTGGTTGATATATCCTGGTGTAAACCTTCAAGAAGGGCACAGGCAGGAAAACATGAGCCAGCAA
CTGAAGAAACGGGCAAAGACAAGACACCAGAAAGGCCTGGGTGGAAGAGCCCCAGTGGGGCTAAGCCCA
GGCAAGGCAAGTCAAGCCAAGACCTGCAGGCGGAAATAGAACCTGTCAGCGCGGTGTGGGCCTTATGTGA
TGGCTATGTGTGCTATGAGCCTGGCCCTCAGGCTCTCGGAGGGATGATTTCTCAGACTGTTACATAGAA
TGCGTCATAAGGGGTGAGTTTTCTCAACCCATCCTGGAAGAGGACTCACTTTTTGAGTCCTTGGAATACC
TAAAGAAAGGATCAGAACAACAGCTTTCTCAAAAGGTTTTCGAAGCAAGCTCCCTTGAATGTTCTTTGGA
ATACATGAAAAAGGGGTAAAGAAAGAGCTTCCACAAAAGATAGTTGGAGAGAATTCGCTTGAGTATTCT
GAGTACATGACAGGCAAGAAGCTTCCGCCTGGAGGAATACCTGGCATTGACCTATCAGATCCTAAACAGC
TCGCAGAATTTGCTAGAAAGAAGCCCCCATAAATAAAGAATATGACAGTCTGAGCGCAATCGCTTGTCC
TCAGAGTGGATGCACTAGGAAGTTGAGGAATAGAGCTGCCCTGAGAAAGCATCTCCTCATTCATGGTCCC
CGAGACCACGTCTGTGCGGAATGTGGGAAAGCGTTCGTTGAGAGCTCAAAACTAAAGAGACATTTCCTGG
TTCATACTGGAGAGAAGCCGTTTCGGTGCACTTTTGAAGGGTGCGGAAAGCGCTTCTCTCTGGACTTTAA
TTTGCGTACGCACGTGCGCATCCACACGGGGAGAAACGTTTCGTGTGTCCCTTTCAAGGCTGCAACAGG
AGGTTTATTCAGTCAAATAACCTGAAAGCCCACATCCTAACGCATGCAAATACGAACAAGAATGAACAAG
AGGGAAAGTAGTCCTCCAACAGGATGAAGCAGATTAACAGAAGAGTGATCAGTGACAAACATGCCTCATT
GATTATTGTTTCTAGGAAGGAATTTCTAAATCAATATTGCAACCCCAAAAGCGGTTATAATTTGGTGTTA
CTAAGATGCTCCTACACTTTGTGATACCGTTTTAAGGACATGGTGCATTTTTTTTTCTTTTATTTGTTTT
ATTTAGAACTTTTTTTATTTGTTTTATTTAGAACTTTGTGTGTTCTTAAAGTGTGCTTCCAACAGGAAGG
TCAGTGATAAATTTTCAAAAGCATAACCTTCAATATATTATCTGTTGGATTATTGGATATAAGACTTATT
TTCATGTACTATAAATATGAAAATAACTTTGATTTTTAATTGTGTAGTTTCCATTTCTTAGCTTTTGCCT
TTTAAATTTATACTTCAGCCAGGCATAGTGACTGATGCCTGTAATCCCAACACTTTGTTGGGAGGCCAAA
GCAGGAGGATAGCTTGAGGCCAGGAGTTCCAGACCAGCCTGGGCAACATAGTGAGATCCTGTCTCTACAA
AAAAATTTGTTTTTATTTGTATTTATATATTTTTATTTTTGTTTTTGTTGGTAGGCGTCTCGCTCTGTCA
CCCAGGCTGGAGTCTAGTGTCGTGATCTTGGCTCACTGCAACCTCCACCTCCCGGGTTCAAGTGATTCTC
TGGCCTCAGCCTCCCAAGTAGCTGGGACTACAGGTGTGTGTCACCACGCCCGGCTAATTTTTGTATTTTT
AGTAGAGATGGGGTTTCACCATGTTGGCCAGGCTAGTCTCAAACTCCTGACCTCCAGTGATCTGCCCACC
TCGGCCTCCCAAAGTGCTGGGATTACAGGTGTGAGCCACTGTGCCTGGCCCCCACAACATGTTTAAACT
TAGCTAGGCCTGGTTGCATACGCCTGTGTTCCCAGCTACTCAGGAGGCTGAAGCAGGAGGATAGCTTGAG
CCCAGGAGTTTGAGGCTACAGTGAGCTGTGATTGCACCACTGTACTCCAGACTGGATAACAGCAAGAGCC
CATCTTTTAAAAAAGTAAAAATTAAAAATATACTTCATGGTTCATGTCATAGCCCTAGAGAATGAAAAA
TTTGCAGTAGATAGTCAATAAATGAATCAGTAGTTAAATATTCCTTAAAGTCAACTGTATTTCATTGTGA
TTTTTGTTTTCTTTTTATCATTGTATCAAACTATATGGAAATCATATGGTTAGATGTGATTATTTGATAA
TGTTAGTCCATTTGAATCCATTTTAGATATTTCACAATTAAAGAATATGAAACTTCAGAAAAAAAAAAA
```
Figure 11.

```
AATCCCTCCCTCCGGCGGGCGTCGCTGGCGGGTGGCTAGGCCCAACGGCAGGAAGCCGACGCTATCCTCC
GTTCCGCGGCGCCGGGTCCGCCTTCCGTCTGTTCTAGGGCCTGCTCCTGCGCGGCAGCTGCTTTAGAAGG
TCTCGAGCCTCCTGTACCTTCCCAGGGATGAACCGGGCCTTCCCTCTGGAAGGCGAGGGTTCGGGCCACA
GTGAGCGAGGGCCAGGGCGGTGGGCGCGCGCAGAGGGAAACCGGATCAGTTGAGAGAGAATCAAGAGTAG
CGGATGAGGCGCTTGTGGGCGCGGCCCGGAAGCCCTCGGGCGCGGGCTGGGAGAAGGAGTGGGCGGAGG
CGCCGCAGGAGGCTCCCGGGGCCTGGTCGGGCCGGCTGGGCCCGGGCGCAGTGGAAGAAAGGGACGGGC
GGTGCCCGGTTGGGCGTCCTGGCCAGCTCACCTTGCCCTGGCGGCTCGCCCCGCCCGGCACTTGGGAGGA
GCAGGGCAGGGCCCGCGGCCTTTGCATTCTGGGACCGCCCCCTTCCATTCCCGGGCCAGCGGCGAGCGGC
AGCGACGGCTGGAGCCGCAGCTACAGCATGAGAGCCGGTGCCGCTCCTCCACGCCTGCGGACGCGTGGCG
AGCGGAGGCAGCGCTGCCTGTTCGCGCCATGGGGGCACCGTGGGGCTCGCCGACGGCGGCGGCGGGCGGG
CGGCGCGGGTGGCGCCGAGGCCGGGGCTGCCATGGACCGTCTGTGTGCTGGCGGCCGCCGGCTTGACGT
GTACGGCGCTGATCACCTACGCTTGCTGGGGGCAGCTGCCGCCGCTGCCCTGGGCGTCGCCAACCCCGTC
GCGACCGGTGGGCGTGCTGCTGTGGTGGGAGCCCTTCGGGGGGCGCGATAGCGCCCCGAGGCCGCCCCCT
GACTGCCGGCTGCGCTTCAACATCAGCGGCTGCCGCCTGCTCACCGACCGCGCGTCCTACGGAGAGGCTC
AGGCCGTGCTTTTCCACCACCGCGACCTCGTGAAGGGGCCCCCGACTGGCCCCCGCCCTGGGGCATCCA
GGCGCACACTGCCGAGGAGGTGGATCTGCGCGTGTTGGACTACGAGGAGGCAGCGGCGGCGGCAGAAGCC
CTGGCGACCTCCAGCCCCAGGCCCCGGGCCAGCGCTGGGTTTGGATGAACTTCGAGTCGCCCTCGCACT
CCCCGGGGCTGCGAAGCCTGGCAAGTAACCTCTTCAACTGGACGCTCTCCTACCGGGCGGACTCGGACGT
CTTTGTGCCTTATGGCTACCTCTACCCCAGAAGCCACCCCGGCGACCCGCCCTCAGGCCTGGCCCCGCCA
```
Figure 12.

```
CTGTCCAGGAAACAGGGGCTGGTGGCATGGGTGGTGAGCCACTGGGACGAGCGCCAGGCCCGGGTCCGCT
ACTACCACCAACTGAGCCAACATGTGACCGTGGACGTGTTCGGCCGGGGCGGGCCGGGGCAGCCGGTGCC
CGAAATTGGGCTCCTGCACACAGTGGCCCGCTACAAGTTCTACCTGGCTTTCGAGAACTCGCAGCACCTG
GATTATATCACCGAGAAGCTCTGGCGCAACGCGTTGCTCGCTGGGGCGGTGCCGGTGGTGCTGGGCCCAG
ACCGTGCCAACTACGAGCGCTTTGTGCCCCGCGGCGCCTTCATCCACGTGGACGACTTCCCAAGTGCCTC
CTCCCTGGCCTCGTACCTGCTTTTCCTCGACCGCAACCCCGCGGTCTATCGCCGCTACTTCCACTGGCGC
CGGAGCTACGCTGTCCACATCACCTCCTTCTGGGACGAGCCTTGGTGCCGGGTGTGCCAGGCTGTACAGA
GGGCTGGGGACCGGCCCAAGAGCATACGGAACTTGGCCAGCTGGTTCGAGCGGTGAAGCCGCGCTCCCCT
GGAAGCGACCCAGGGGAGGCCAAGTTGTCAGCTTTTTGATCCTCTACTGTGCATCTCCTTGACTGCCGCA
TCATGGGAGTAAGTTCTTCAAACACCCATTTTTGCTCTATGGGAAAAAAACGATTTACCAATTAATATTA
CTCAGCACAGAGATGGGGGCCCGGTTTCCATATTTTTTGCACAGCTAGCAATTGGGCTCCCTTTGCTGCT
GATGGGCATCATTGTTTAGGGGTGAAGGAGGGGGTTCTTCCTCACCTTGTAACCAGTGCAGAAATGAAAT
AGCTTAGCGGCAAGAAGCCGTTGAGGCGGTTTCCTGAATTTCCCCATCTGCCACAGGCCATATTTGTGGC
CCGTGCAGCTTCCAAATCTCATACACAACTGTTCCCGATTCACGTTTTTCTGGACCAAGGTGAAGCAAAT
TTGTGGTTGTAGAAGGAGCCTTGTTGGTGGAGAGTGGAAGGACTGTGGCTGCAGGTGGGACTTTGTTGTT
TGGATTCCTCACAGCCTTGGCTCCTGAGAAAGGTGAGGAGGGCAGTCCAAGAGGGGCCGCTGACTTCTTT
CACAAGTACTATCTGTTCCCCTGTCCTGTGAATGGAAGCAAAGTGCTGGATTGTCCTTGGAGGAAACTTA
AGATGAATACATGCGTGTACCTCACTTTACATAAGAAATGTATTCCTGAAAAGCTGCATTTAAATCAAGT
CCCAAATTCATTGACTTAGGGGAGTTCAGTATTTAATGAAACCCTATGGAGAATTTATCCCTTTACAATG
TGAATAGTCATCTCCTAATTTGTTTCTTCTGTCTTTATGTTTTTCTATAACCTGGATTTTTTAAATCATA
TTAAAATTACAGATGTGAAAATAAAGCAGAAGCAACCTTTTTCCCTCTTCCCAGAAAACCAGTCTGTGTT
TACAGACAGAAGAGAAGGAAGCCATAGTGTCACTTCCACACAATTATTTATTTCATGTCTTTACTGGACC
TGAAATTTAAACTGCAATGCCAGTCCTGCAGGAGTGCTGGCATTACCCTCTGCAGAACAGTGAAAGGTAT
TGCACTACATTATGGAATCATGCAAAAGGAAAAAAAGTTTCATGATATCTGTTGTTGGCAGTTTTTGTTT
ATCTCTGACAGTTTTTAGTTAAATGTTTAGATCCTCAGAACTACATTAGTGCCTACTATTAACTTACTCT
GTCTCTTGTTAAAGGCTAAATCTGCGCTTCTCCCTGGTGCCAGCAGGTTCCCCTCACAGTCAATGCAGTG
GTATAGCATATCCTCACATTTCTAGTGCCCTTGAGACTGTGCTATGGAACCAATCTTGAACATACATGCA
TTGACTTGACAAGTTACTGAGTAAGCAGCATATTCAGCAGGTGCCACTACATGCCTACTCTGCCAGACAC
TGAGCTTGGGCCCTAGGGAAGATAGAGAATTATACAAGGCAAAGTCCTTCTCTTTAGGGCTCTTACAAT
CTATCACTTCCAAAAAGTAAATGGTGACTGATAAAACAATTGGCAGAACCTGTTTGATTACTGTGACAGT
CTTAATGATACCATAAATCAATATTAGAAAGCTAGTTGACTTAAAGCCTGAAATAATGGGAGTTTTCTCC
TCCACTTATTAGAATAAGGACCCTCAGTGACTAATTATTGTGGGTAGGGTCAAGATTAACTAGTTTTATA
CAGAGTTCTGCTGTAAATAGTCATTTTGCATTTGATTAGTGCAGTTCTCTGAATCATAAAGCAAGTTTTA
CCTCTCTGTACATGTTTTGCAGACATACTTGAAAAGCTCACTTAAATCTAGGTGCTTCAATTCACTTTC
TTGAGAGGACAAATGAAAAGCTGTGGAGAAAATGTCCTCATTAAAGTATTAAAGTGTGGGCAGAATTACA
ATTACAAAGTGCCAGCCACCGAATAAAGATAAAAGTTCAGTTCTTAAAATGAGTTTTTATGAGATAACAG
TCAGTGATCTTGGTGTTACCGGGATTCCACATGGGGCAGTGGGAAAGAGTTCAGGTTTTGAAGGTAACCT
AGTTTAGATTTGAATTCCAGCTATGTGACATTGGGTAAATTAGTAGTAGTCCTGAGCCTCAGCGTCCTCA
TCTATAAAATGACTGGCGAAAATACTTCACAAGCTCATTTTGAGCACTTTAGGAAGTAAGTGAAAGTACC
TAAAATAGCAGGCACCCAATTGATGATTTTATATCTTCCTTCTTTGCTTGCAGTGATTTCAGGATGTCCT
CATATCTATTTATAGGTCTAAAATTATATCTTAAGGTATGTTGTAGAATAAATTAAAAGGATAATCTAAA
TCACCATTTAGATTAAGCTTGACTTGCAAACTAGGAAGAAGCACCTAGGCTTTCTTTGAAAATATTTTTT
TGGTTCGTTTTGGTAAAGCTCTATAAATTGGTATCTATTATTTTACCAATTTTTTTTTAGTATTAAGTCC
ATTTAGAACTAACCATATTATTTATGGAATAATTAGCATGAGGAAGGTATAATTGCATTTTTTTTTTTT
GAGACGGAGTCTTGCACTGTAGCCCCAGCTGGACTGCAGTGGCGTGATCTTGGCTCACTGCAACCTCCGC
CTCCCAGGTTCAAGCGATTCTCCTGCCTCAGCCTCCCGAGCAGCTGAGACTACAGGCGCCTGCCACCACG
CCTGGCCAATTTTTTGTATTTTTAGTAGAGACTGCGTTTCACCATGTTGGGCAGGCTGGTCTTGAACTCC
TGACCTTGTGATCCACCTGCCTCGGCCTCTCAGAGAGCTGGGATTACAGGTGTGAGCCGCCGTGCCCAGC
CATTGCATTTTTATTCACATACACATTGTTAATGTGGAACAATTTAACACTAATCTCATCAGAGAGCGAG
ATGAATGTGGCAATTGCTCATTTTATTTTGCATATATTAAATTGAGTAGGTTCAGCTCTAACATACCTTA
AGAAAAATGCATATCGGTGCACTGTATGTATTTCAAAATGCCTTTCCTATGATTGTCATGTCCTCCTTTA
AGGCTTTTCCCTCAAATTTATTACAAATTTAGTATTTTTAGTACTTGATGACTCTAATTACATGAATGCA
CCTGGAATGACATTTGTAACAGAAGACGGTCTGACTTGCTTTCAGTATTCACAAGTTCTTTCCAGTTTCC
AAGTCTTTTCCTAGCAGTAATTTAGGGGAGACAGAGGAGTTTCATGTAAAGAGCATGCAGTTTGGAGTCA
GAACCTGGGTATGACTCTGTGGCCTTGATGAAGCAAGTTACTTAAACTCTTGAGTTTTAGCTTTCTCCTT
TACAATGCATGAATGCCTATCCCCCTACAAAACAAAGATTAAATGTGATGATGTATGCCAAGGTGCTTTG
TATATTGTAAAGTGCTATATAATTATAAGATGTTCTAAATTTTCAAGGATCTAAACCAGGGATTGGCAAA
CGTTTTTCCAGGGAGTAAATATTTTACGCTTTGCATATATAATTTATGGAGGTGTTGAGAGGATAGATTA
GACACTTGAAGTACTCAGGATAGTGCCTGGCATGTAGGAAGCACCTGGAAAATATTCGCTGTGATTACCA
TCAGTCCATTTTACCGAGGAAGGAGCCAAGGTCCAGGCCCACTGAAGGACTTGCATAACATTACAATAGC
```

Figure 12 (continued).

```
AGTGGCAGAACCAGCCATGCTTCTGCAAATCACAACCTCTTTGAGCCTCTGTCACCTGAACTGCAAAATG
AGTGGGTTAGACAAAATCATCTGTTGGGACCTCCTAGTTCCACGTGCTATCATTCTACTAACTGGCACCC
TAAGGTTGAAAGTGCTTATCTGCTTTCCAATGTGGCTTCCTTACAGTCTGGAACTGACAATATGCAGGAG
CAGTAAACTGGCAGAAAACCAGGAATCAGAGAAAGAAAATATAATTTAACTTTAAAGATGTAAATTATAT
ATATAGTATATTTATATATATTTTTAAAGCTTTATATGCCTCAAATATCAGGGAAAGGAGCCAAGTCCTTG
GTATTTAGTTTGGTGAATACTTGCATTGAATACATGTCAAGATGTCAAGTCATTTTTGAATGTGTCTCAG
GGATTTCTATGCTACACATTCTTTTAACAAATCAAGTATTTATGTACACATGTTCAGATTTTTTGACAAA
ATGATTAAAATAATGAGATGGAAAATGAAAAAAAAAAAAAAAAA
```
Figure 12 (continued).

```
AGCCCTTTGTTTATGGCCTGATCTAGCTAAGGCTTCTAGACTTCAGGAGCTTAAGAATCGTCCGGAGGGC
TGGGCGTGGCGGTGCAGGCCTGTAGTCCCACCCACTCCGAAGGCTGCGGAGGGAGGATCAACTTGAGTCT
GGGAACTCAGCCAGGAATTCAAGACCAGCCTGGGCAACACAGTGAGGCCCCCTACCCACATCCTCTCCGT
CCCCGCAATCTCCTTCCATCCCAGGGTGTTGCTGAAAATGTCAGATGCAAATTTGGATAGCAGCAAGAAG
AATTTCTTGGAGGGGGAAGTAGATGATGAGGAAAGTGTGATTTTGACACTGGTGCCAGTTAAAGATGACG
CAAATATGGAACAAATGGAACCAAGCGTTTCTTCAACTTCTGATGTCAAACTGGAGAAGCCTAAGAAATA
CAATCCAGGTCATCTACTTCAAACAAATGAGCAATTTACAGCTCCACAAAAAGCTAGATGCAAAATACCA
GCCCTTCCCTTGCCGACCATTTTGCCTCCCATTAATAAGGTGTGTCGGGACACTTTGCGGGACTGGTGTC
AACAACTCGGTTTGAGTACTAATGGCAAGAAAATCGAAGTTTATCTGAGGCTTCATAGGCATGCTTACCC
TGAACAACGGCAAGATATGCCTGAAATGTCACAAGAGACCAGATTACAGCGATGTTCGAGGAAACGCAAG
GCAGTGACCAAGAGAGCAAGGCTTCAGAGAAGTTATGAGATGAATGAGAGAGCAGAAGAGACCAATACAG
TTGAAGTGATAACTTCAGCACCGGGAGCCATGTTGGCATCATGGGCAAGAATTGCTGCAAGAGCTGTTCA
GCCTAAGGCTTTGAATTCATGTTCCATTCCTGTTTCTGTTGAGGCCTTTTTGATGCAAGCCTCTGGCGTC
AGGTGGTGTGTGGTCCATGGCAGACTTCTCTCGGCAGACACAAAGGGTTGGGTACGCCTGCAGTTTCATG
CAGGTCAGGCCTGGGTGCCTACCACTCACAGGAGGATGATTTCTCTCTTCTTGTTACCTGCCTGCATTTT
CCCATCCCCAGGCATAGAAGATAATATGTTATGCCCCGACTGTGCTAAGAGGAATAAGAAGATGATGAAA
AGATTAATGACAGTAGAGAAGTAGCAGCAACCTGTTTGAATACAATGTACTAAAGGAGGGATGTACTTTC
AGATCATGTAACCTATTACGAAGGAGTGGAAGAGGAGACAATTTGAATGAATCCTCATGATCTACAAAAC
AAAATCATAGTGACTAGGACTCCACAGTGAAGATGGTTGACTAGTGACACAGCCCCATCTAAAGAATCCC
TTTCTGTATGTCTGAAAACCCATTAAAATAAAGTCACTGCAATTGGCCTTGTAAAAAAAAAAA
```
Figure 13.

```
TGGAGCTCCGGTTTTCAGCCTCTTTCCGGGCTACCTGGTAGCAATTTGAGGCTCTGTCATCAGTTTCTGC
TACGTTTCAAAGATCCTGGAGAAGCCTAGTGTTGTGTCAAGACGCCGATGGACCCATCACAGTTTAATCC
AACCTACATCCCAGGGTCTCCACAAATGCTCACCGAAGAAAATTCCCGGGACGATTCAGGGGCCTCTCAA
ATCTCCTCCGAGACGTTGATAAAGAACCTTAGTAACTTGACTATCAACGCTAGTAGCGAATCGTTTCCC
CTCTATCGGAAGCTTTACTCCGTCGAGAGTCTGTAGGAGCAGCAGTCCTCAGGGAAATCGAAGATGAGTG
GCTTTACAGCAGGAGAGGAGTAAGAACATTGCTGTCTGTGCAGAGAGAAAAGATGGCAAGATTGAGATAC
ATGTTACTCGGCGGAGTTCGTACGCATGAAAGAAGACCAACAAACAAGGAGCCTAAGGGAGTTAAGAAGG
AATCAAGACCATTCAAATGTCCTGCAGTTTCTGCGTGTCTAATGGATGGGATCCTTCTGAGAATGCTAG
AATAGGGAATCAAGACACCAAGCCACTTCAGCCATAAATCTTATTCTTGCACCTTTTTTTCTTGGTAGTA
ATTTTATATAGCAGGTTGAGAAAGCTACTCTATGCTAGTATAGACTATACACCAATAATTTTGATAATGA
GTTCTAGGATGTATTTTCTTGTATCTTTTTCTTCCTACTATGATACTAGTAATTCATAAGGGATCTGTG
TAATCTGAATGTATTTGAATAACTTTAGCTCTACTGTTTGATTTGACCCAAAGAAGCCAAGATGATATAA
GTATTCCCATGTGTCTTAGAAGCCCAAAGTCAGTGAGATGAAACCCAACATCAAGAAATTGAAGCAAAGT
TACTTATGGATAAAGAAAGCATTAGGTAGTTGGGCTATAGCATAATTAGATTTCTGGCTTTCAAAAATT
TGGATTGCAATCACAGCAAACTTTGTTATTTTTACAGTTTTCAGTACAAAAGTGTTTATATAGAAACAAT
AAAGTTGACATTTGAGTACCTTTTAAAAA
```
Figure 14.

SEQUENCE LISTING

```
<160> NUMBER OF SEQ ID NOS: 17

<210> SEQ ID NO 1
<211> LENGTH: 3695
<212> TYPE: PRT
<213> ORGANISM: Homo sapiens

<400> SEQUENCE: 1

Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
            20                  25                  30

Ala Arg Ala Arg Glu Glu Ala Gly Gly Phe Ser Leu His Pro Pro
        35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Asp Pro Asn Gln
                85                  90                  95

Thr Ile Arg Gly Gln Tyr Cys Asp Ile Cys Thr Ala Ala Asn Ser Asn
            100                 105                 110
```

-continued

```
Lys Ala His Pro Ala Ser Asn Ala Ile Asp Gly Thr Glu Arg Trp Trp
            115                 120                 125

Gln Ser Pro Pro Leu Ser Arg Gly Leu Glu Tyr Asn Glu Val Asn Val
        130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Ala Ser Ser Lys
            180                 185                 190

Arg Asp Cys Leu Glu Arg Phe Gly Pro Gln Thr Leu Glu Arg Ile Thr
        195                 200                 205

Arg Asp Asp Ala Ala Ile Cys Thr Thr Glu Tyr Ser Arg Ile Val Pro
210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
        290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Pro Trp Lys Pro Ala Thr Ala Asn Ser
            340                 345                 350

Ala Asn Glu Cys Gln Ser Cys Asn Cys Tyr Gly His Ala Thr Asp Cys
        355                 360                 365

Tyr Tyr Asp Pro Glu Val Asp Arg Arg Arg Ala Ser Gln Ser Leu Asp
370                 375                 380

Gly Thr Tyr Gln Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
        435                 440                 445

Cys Arg Pro Asn Phe Ser Gly Glu Arg Cys Asp Val Cys Ala Glu Gly
        450                 455                 460

Phe Thr Gly Phe Pro Ser Cys Tyr Pro Thr Pro Ser Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
        515                 520                 525

Cys Ala Pro Gly Phe Tyr Gly Pro Gly Cys Gln Pro Cys Gln Cys Ser
```

-continued

```
              530                 535                 540
Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                    565                 570                 575

Gly Tyr Phe His Phe Pro Leu Cys Gln Leu Cys Gly Cys Ser Pro Ala
                580                 585                 590

Gly Thr Leu Pro Glu Gly Cys Asp Glu Ala Gly Arg Cys Leu Cys Gln
                595                 600                 605

Pro Glu Phe Ala Gly Pro His Cys Asp Arg Cys Arg Pro Gly Tyr His
            610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Leu Cys Arg Cys Arg Pro Gly Tyr
                    645                 650                 655

Thr Gly Thr Ala Cys Gln Glu Cys Ser Pro Gly Phe His Gly Phe Pro
                660                 665                 670

Ser Cys Val Pro Cys His Cys Ser Ala Glu Gly Ser Leu His Ala Ala
                675                 680                 685

Cys Asp Pro Arg Ser Gly Gln Cys Ser Cys Arg Pro Arg Val Thr Gly
    690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
                740                 745                 750

Pro Ser Cys Asp Arg Cys Lys Pro Gly Phe Trp Gly Leu Ser Pro Ser
            755                 760                 765

Asn Pro Glu Gly Cys Thr Arg Cys Ser Cys Asp Leu Arg Gly Thr Leu
            770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
            820                 825                 830

Ile Gly Gly Ala Leu Gly Gln Ser Cys Glu Pro Arg Thr Gly Val Cys
    835                 840                 845

Arg Cys Arg Pro Asn Thr Gln Gly Pro Thr Cys Ser Glu Pro Ala Arg
850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
                900                 905                 910

Gln Pro Arg Ile Val Ala Arg Leu Asn Leu Thr Ser Pro Asp Leu Phe
            915                 920                 925

Trp Leu Val Phe Arg Tyr Val Asn Arg Gly Ala Met Ser Val Ser Gly
            930                 935                 940

Arg Val Ser Val Arg Glu Glu Gly Arg Ser Ala Thr Cys Ala Asn Cys
945                 950                 955                 960
```

```
Thr Ala Gln Ser Gln Pro Val Ala Phe Pro Pro Ser Thr Glu Pro Ala
                965                 970                 975

Phe Ile Thr Val Pro Gln Arg Gly Phe Gly Glu Pro Phe Val Leu Asn
                980                 985                 990

Pro Gly Thr Trp Ala Leu Arg Val Glu Ala Glu Gly Val Leu Leu Asp
            995                 1000                1005

Tyr Val Val Leu Leu Pro Ser Ala Tyr Tyr Glu Ala Ala Leu Leu
        1010                1015                1020

Gln Leu Arg Val Thr Glu Ala Cys Thr Tyr Arg Pro Ser Ala Gln
        1025                1030                1035

Gln Ser Gly Asp Asn Cys Leu Leu Tyr Thr His Leu Pro Leu Asp
        1040                1045                1050

Gly Phe Pro Ser Ala Ala Gly Leu Glu Ala Leu Cys Arg Gln Asp
        1055                1060                1065

Asn Ser Leu Pro Arg Pro Cys Pro Thr Glu Gln Leu Ser Pro Ser
        1070                1075                1080

His Pro Pro Leu Ile Thr Cys Thr Gly Ser Asp Val Asp Val Gln
        1085                1090                1095

Leu Gln Val Ala Val Pro Gln Pro Gly Arg Tyr Ala Leu Val Val
        1100                1105                1110

Glu Tyr Ala Asn Glu Asp Ala Arg Gln Glu Val Gly Val Ala Val
        1115                1120                1125

His Thr Pro Gln Arg Ala Pro Gln Gln Gly Leu Leu Ser Leu His
        1130                1135                1140

Pro Cys Leu Tyr Ser Thr Leu Cys Arg Gly Thr Ala Arg Asp Thr
        1145                1150                1155

Gln Asp His Leu Ala Val Phe His Leu Asp Ser Glu Ala Ser Val
        1160                1165                1170

Arg Leu Thr Ala Glu Gln Ala Arg Phe Phe Leu His Gly Val Thr
        1175                1180                1185

Leu Val Pro Ile Glu Glu Phe Ser Pro Glu Phe Val Glu Pro Arg
        1190                1195                1200

Val Ser Cys Ile Ser Ser His Gly Ala Phe Gly Pro Asn Ser Ala
        1205                1210                1215

Ala Cys Leu Pro Ser Arg Phe Pro Lys Pro Pro Gln Pro Ile Ile
        1220                1225                1230

Leu Arg Asp Cys Gln Val Ile Pro Leu Pro Pro Gly Leu Pro Leu
        1235                1240                1245

Thr His Ala Gln Asp Leu Thr Pro Ala Met Ser Pro Ala Gly Pro
        1250                1255                1260

Arg Pro Arg Pro Pro Thr Ala Val Asp Pro Asp Ala Glu Pro Thr
        1265                1270                1275

Leu Leu Arg Glu Pro Gln Ala Thr Val Val Phe Thr Thr His Val
        1280                1285                1290

Pro Thr Leu Gly Arg Tyr Ala Phe Leu Leu His Gly Tyr Gln Pro
        1295                1300                1305

Ala His Pro Thr Phe Pro Val Glu Val Leu Ile Asn Ala Gly Arg
        1310                1315                1320

Val Trp Gln Gly His Ala Asn Ala Ser Phe Cys Pro His Gly Tyr
        1325                1330                1335

Gly Cys Arg Thr Leu Val Val Cys Glu Gly Gln Ala Leu Leu Asp
        1340                1345                1350
```

```
Val Thr His Ser Glu Leu Thr Val Thr Val Arg Val Pro Lys Gly
1355                1360                1365

Arg Trp Leu Trp Leu Asp Tyr Val Leu Val Val Pro Glu Asn Val
1370                1375                1380

Tyr Ser Phe Gly Tyr Leu Arg Glu Glu Pro Leu Asp Lys Ser Tyr
1385                1390                1395

Asp Phe Ile Ser His Cys Ala Ala Gln Gly Tyr His Ile Ser Pro
1400                1405                1410

Ser Ser Ser Ser Leu Phe Cys Arg Asn Ala Ala Ala Ser Leu Ser
1415                1420                1425

Leu Phe Tyr Asn Asn Gly Ala Arg Pro Cys Gly Cys His Glu Val
1430                1435                1440

Gly Ala Thr Gly Pro Thr Cys Glu Pro Phe Gly Gln Cys Pro
1445                1450                1455

Cys His Ala His Val Ile Gly Arg Asp Cys Ser Arg Cys Ala Thr
1460                1465                1470

Gly Tyr Trp Gly Phe Pro Asn Cys Arg Pro Cys Asp Cys Gly Ala
1475                1480                1485

Arg Leu Cys Asp Glu Leu Thr Gly Gln Cys Ile Cys Pro Pro Arg
1490                1495                1500

Thr Ile Pro Pro Asp Cys Leu Leu Cys Gln Pro Gln Thr Phe Gly
1505                1510                1515

Cys His Pro Leu Val Gly Cys Glu Glu Cys Asn Cys Ser Gly Pro
1520                1525                1530

Gly Ile Gln Glu Leu Thr Asp Pro Thr Cys Asp Thr Asp Ser Gly
1535                1540                1545

Gln Cys Lys Cys Arg Pro Asn Val Thr Gly Arg Arg Cys Asp Thr
1550                1555                1560

Cys Ser Pro Gly Phe His Gly Tyr Pro Arg Cys Arg Pro Cys Asp
1565                1570                1575

Cys His Glu Ala Gly Thr Ala Pro Gly Val Cys Asp Pro Leu Thr
1580                1585                1590

Gly Gln Cys Tyr Cys Lys Glu Asn Val Gln Gly Pro Lys Cys Asp
1595                1600                1605

Gln Cys Ser Leu Gly Thr Phe Ser Leu Asp Ala Ala Asn Pro Lys
1610                1615                1620

Gly Cys Thr Arg Cys Phe Cys Phe Gly Ala Thr Glu Arg Cys Arg
1625                1630                1635

Ser Ser Ser Tyr Thr Arg Gln Glu Phe Val Asp Met Glu Gly Trp
1640                1645                1650

Val Leu Leu Ser Thr Asp Arg Gln Val Val Pro His Glu Arg Gln
1655                1660                1665

Pro Gly Thr Glu Met Leu Arg Ala Asp Leu Arg His Val Pro Glu
1670                1675                1680

Ala Val Pro Glu Ala Phe Pro Glu Leu Tyr Trp Gln Ala Pro Pro
1685                1690                1695

Ser Tyr Leu Gly Asp Arg Val Ser Ser Tyr Gly Gly Thr Leu Arg
1700                1705                1710

Tyr Glu Leu His Ser Glu Thr Gln Arg Gly Asp Val Phe Val Pro
1715                1720                1725

Met Glu Ser Arg Pro Asp Val Val Leu Gln Gly Asn Gln Met Ser
1730                1735                1740

Ile Thr Phe Leu Glu Pro Ala Tyr Pro Thr Pro Gly His Val His
```

```
               1745                1750                1755
Arg Gly Gln Leu Gln Leu Val Glu Gly Asn Phe Arg His Thr Glu
        1760                1765                1770
Thr Arg Asn Thr Val Ser Arg Glu Glu Leu Met Met Val Leu Ala
        1775                1780                1785
Ser Leu Glu Gln Leu Gln Ile Arg Ala Leu Phe Ser Gln Ile Ser
        1790                1795                1800
Ser Ala Val Phe Leu Arg Arg Val Ala Leu Glu Val Ala Ser Pro
        1805                1810                1815
Ala Gly Gln Gly Ala Leu Ala Ser Asn Val Glu Leu Cys Leu Cys
        1820                1825                1830
Pro Ala Ser Tyr Arg Gly Asp Ser Cys Gln Glu Cys Ala Pro Gly
        1835                1840                1845
Phe Tyr Arg Asp Val Lys Gly Leu Phe Leu Gly Arg Cys Val Pro
        1850                1855                1860
Cys Gln Cys His Gly His Ser Asp Arg Cys Leu Pro Gly Ser Gly
        1865                1870                1875
Val Cys Val Asp Cys Gln His Asn Thr Glu Gly Ala His Cys Glu
        1880                1885                1890
Arg Cys Gln Ala Gly Phe Val Ser Ser Arg Asp Asp Pro Ser Ala
        1895                1900                1905
Pro Cys Val Ser Cys Pro Cys Pro Leu Ser Val Pro Ser Asn Asn
        1910                1915                1920
Phe Ala Glu Gly Cys Val Leu Arg Gly Gly Arg Thr Gln Cys Leu
        1925                1930                1935
Cys Lys Pro Gly Tyr Ala Gly Ala Ser Cys Glu Arg Cys Ala Pro
        1940                1945                1950
Gly Phe Phe Gly Asn Pro Leu Val Leu Gly Ser Ser Cys Gln Pro
        1955                1960                1965
Cys Asp Cys Ser Gly Asn Gly Asp Pro Asn Leu Leu Phe Ser Asp
        1970                1975                1980
Cys Asp Pro Leu Thr Gly Ala Cys Arg Gly Cys Leu Arg His Thr
        1985                1990                1995
Thr Gly Pro Arg Cys Glu Ile Cys Ala Pro Gly Phe Tyr Gly Asn
        2000                2005                2010
Ala Leu Leu Pro Gly Asn Cys Thr Arg Cys Asp Cys Thr Pro Cys
        2015                2020                2025
Gly Thr Glu Ala Cys Asp Pro His Ser Gly His Cys Leu Cys Lys
        2030                2035                2040
Ala Gly Val Thr Gly Arg Arg Cys Asp Arg Cys Gln Glu Gly His
        2045                2050                2055
Phe Gly Phe Asp Gly Cys Gly Gly Cys Arg Pro Cys Ala Cys Gly
        2060                2065                2070
Pro Ala Ala Glu Gly Ser Glu Cys His Pro Gln Ser Gly Gln Cys
        2075                2080                2085
His Cys Arg Pro Gly Thr Met Gly Pro Gln Cys Arg Glu Cys Ala
        2090                2095                2100
Pro Gly Tyr Trp Gly Leu Pro Glu Gln Gly Cys Arg Arg Cys Gln
        2105                2110                2115
Cys Pro Gly Gly Arg Cys Asp Pro His Thr Gly Arg Cys Asn Cys
        2120                2125                2130
Pro Pro Gly Leu Ser Gly Glu Arg Cys Asp Thr Cys Ser Gln Gln
        2135                2140                2145
```

His Gln Val Pro Val Pro Gly Gly Pro Val Gly His Ser Ile His
2150            2155                2160

Cys Glu Val Cys Asp His Cys Val Val Leu Leu Leu Asp Asp Leu
2165            2170                2175

Glu Arg Ala Gly Ala Leu Leu Pro Ala Ile His Glu Gln Leu Arg
2180            2185                2190

Gly Ile Asn Ala Ser Ser Met Ala Trp Ala Arg Leu His Arg Leu
2195            2200                2205

Asn Ala Ser Ile Ala Asp Leu Gln Ser Gln Leu Arg Ser Pro Leu
2210            2215                2220

Gly Pro Arg His Glu Thr Ala Gln Gln Leu Glu Val Leu Glu Gln
2225            2230                2235

Gln Ser Thr Ser Leu Gly Gln Asp Ala Arg Arg Leu Gly Gly Gln
2240            2245                2250

Ala Val Gly Thr Arg Asp Gln Ala Ser Gln Leu Leu Ala Gly Thr
2255            2260                2265

Glu Ala Thr Leu Gly His Ala Lys Thr Leu Leu Ala Ala Ile Arg
2270            2275                2280

Ala Val Asp Arg Thr Leu Ser Glu Leu Met Ser Gln Thr Gly His
2285            2290                2295

Leu Gly Leu Ala Asn Ala Ser Ala Pro Ser Gly Glu Gln Leu Leu
2300            2305                2310

Arg Thr Leu Ala Glu Val Glu Arg Leu Leu Trp Glu Met Arg Ala
2315            2320                2325

Arg Asp Leu Gly Ala Pro Gln Ala Ala Ala Glu Ala Glu Leu Ala
2330            2335                2340

Ala Ala Gln Arg Leu Leu Ala Arg Val Gln Glu Gln Leu Ser Ser
2345            2350                2355

Leu Trp Glu Glu Asn Gln Ala Leu Ala Thr Gln Thr Arg Asp Arg
2360            2365                2370

Leu Ala Gln His Glu Ala Gly Leu Met Asp Leu Arg Glu Ala Leu
2375            2380                2385

Asn Arg Ala Val Asp Ala Thr Arg Glu Ala Gln Glu Leu Asn Ser
2390            2395                2400

Arg Asn Gln Glu Arg Leu Glu Glu Ala Leu Gln Arg Lys Gln Glu
2405            2410                2415

Leu Ser Arg Asp Asn Ala Thr Leu Gln Ala Thr Leu His Ala Ala
2420            2425                2430

Arg Asp Thr Leu Ala Ser Val Phe Arg Leu Leu His Ser Leu Asp
2435            2440                2445

Gln Ala Lys Glu Glu Leu Glu Arg Leu Ala Ala Ser Leu Asp Gly
2450            2455                2460

Ala Arg Thr Pro Leu Leu Gln Arg Met Gln Thr Phe Ser Pro Ala
2465            2470                2475

Gly Ser Lys Leu Arg Leu Val Glu Ala Ala Glu Ala His Ala Gln
2480            2485                2490

Gln Leu Gly Gln Leu Ala Leu Asn Leu Ser Ser Ile Ile Leu Asp
2495            2500                2505

Val Asn Gln Asp Arg Leu Thr Gln Arg Ala Ile Glu Ala Ser Asn
2510            2515                2520

Ala Tyr Ser Arg Ile Leu Gln Ala Val Gln Ala Ala Glu Asp Ala
2525            2530                2535

```
Ala Gly Gln Ala Leu Gln Gln Ala Asp His Thr Trp Ala Thr Val
    2540                2545                2550

Val Arg Gln Gly Leu Val Asp Arg Ala Gln Gln Leu Leu Ala Asn
    2555                2560                2565

Ser Thr Ala Leu Glu Glu Ala Met Leu Gln Glu Gln Gln Arg Leu
    2570                2575                2580

Gly Leu Val Trp Ala Ala Leu Gln Gly Ala Arg Thr Gln Leu Arg
    2585                2590                2595

Asp Val Arg Ala Lys Lys Asp Gln Leu Glu Ala His Ile Gln Ala
    2600                2605                2610

Ala Gln Ala Met Leu Ala Met Asp Thr Asp Glu Thr Ser Lys Lys
    2615                2620                2625

Ile Ala His Ala Lys Ala Val Ala Ala Glu Ala Gln Asp Thr Ala
    2630                2635                2640

Thr Arg Val Gln Ser Gln Leu Gln Ala Met Gln Glu Asn Val Glu
    2645                2650                2655

Arg Trp Gln Gly Gln Tyr Glu Gly Leu Arg Gly Gln Asp Leu Gly
    2660                2665                2670

Gln Ala Val Leu Asp Ala Gly His Ser Val Ser Thr Leu Glu Lys
    2675                2680                2685

Thr Leu Pro Gln Leu Leu Ala Lys Leu Ser Ile Leu Glu Asn Arg
    2690                2695                2700

Gly Val His Asn Ala Ser Leu Ala Leu Ser Ala Ser Ile Gly Arg
    2705                2710                2715

Val Arg Glu Leu Ile Ala Gln Ala Arg Gly Ala Ala Ser Lys Val
    2720                2725                2730

Lys Val Pro Met Lys Phe Asn Gly Arg Ser Gly Val Gln Leu Arg
    2735                2740                2745

Thr Pro Arg Asp Leu Ala Asp Leu Ala Ala Tyr Thr Ala Leu Lys
    2750                2755                2760

Phe Tyr Leu Gln Gly Pro Glu Pro Glu Pro Gly Gln Gly Thr Glu
    2765                2770                2775

Asp Arg Phe Val Met Tyr Met Gly Ser Arg Gln Ala Thr Gly Asp
    2780                2785                2790

Tyr Met Gly Val Ser Leu Arg Asp Lys Lys Val His Trp Val Tyr
    2795                2800                2805

Gln Leu Gly Glu Ala Gly Pro Ala Val Leu Ser Ile Asp Glu Asp
    2810                2815                2820

Ile Gly Glu Gln Phe Ala Ala Val Ser Leu Asp Arg Thr Leu Gln
    2825                2830                2835

Phe Gly His Met Ser Val Thr Val Glu Arg Gln Met Ile Gln Glu
    2840                2845                2850

Thr Lys Gly Asp Thr Val Ala Pro Gly Ala Glu Gly Leu Leu Asn
    2855                2860                2865

Leu Arg Pro Asp Asp Phe Val Phe Tyr Val Gly Gly Tyr Pro Ser
    2870                2875                2880

Thr Phe Thr Pro Pro Pro Leu Leu Arg Phe Pro Gly Tyr Arg Gly
    2885                2890                2895

Cys Ile Glu Met Asp Thr Leu Asn Glu Glu Val Val Ser Leu Tyr
    2900                2905                2910

Asn Phe Glu Arg Thr Phe Gln Leu Asp Thr Ala Val Asp Arg Pro
    2915                2920                2925

Cys Ala Arg Ser Lys Ser Thr Gly Asp Pro Trp Leu Thr Asp Gly
```

```
            2930                2935                2940

Ser Tyr Leu Asp Gly Thr Gly Phe Ala Arg Ile Ser Phe Asp Ser
    2945                2950                2955

Gln Ile Ser Thr Thr Lys Arg Phe Glu Gln Glu Leu Arg Leu Val
    2960                2965                2970

Ser Tyr Ser Gly Val Leu Phe Phe Leu Lys Gln Gln Ser Gln Phe
    2975                2980                2985

Leu Cys Leu Ala Val Gln Glu Gly Ser Leu Val Leu Leu Tyr Asp
    2990                2995                3000

Phe Gly Ala Gly Leu Lys Lys Ala Val Pro Leu Gln Pro Pro Pro
    3005                3010                3015

Pro Leu Thr Ser Ala Ser Lys Ala Ile Gln Val Phe Leu Leu Gly
    3020                3025                3030

Gly Ser Arg Lys Arg Val Leu Val Arg Val Glu Arg Ala Thr Val
    3035                3040                3045

Tyr Ser Val Glu Gln Asp Asn Asp Leu Glu Leu Ala Asp Ala Tyr
    3050                3055                3060

Tyr Leu Gly Gly Val Pro Pro Asp Gln Leu Pro Pro Ser Leu Arg
    3065                3070                3075

Arg Leu Phe Pro Thr Gly Gly Ser Val Arg Gly Cys Val Lys Gly
    3080                3085                3090

Ile Lys Ala Leu Gly Lys Tyr Val Asp Leu Lys Arg Leu Asn Thr
    3095                3100                3105

Thr Gly Val Ser Ala Gly Cys Thr Ala Asp Leu Leu Val Gly Arg
    3110                3115                3120

Ala Met Thr Phe His Gly His Gly Phe Leu Arg Leu Ala Leu Ser
    3125                3130                3135

Asn Val Ala Pro Leu Thr Gly Asn Val Tyr Ser Gly Phe Gly Phe
    3140                3145                3150

His Ser Ala Gln Asp Ser Ala Leu Leu Tyr Tyr Arg Ala Ser Pro
    3155                3160                3165

Asp Gly Leu Cys Gln Val Ser Leu Gln Gln Gly Arg Val Ser Leu
    3170                3175                3180

Gln Leu Leu Arg Thr Glu Val Lys Thr Gln Ala Gly Phe Ala Asp
    3185                3190                3195

Gly Ala Pro His Tyr Val Ala Phe Tyr Ser Asn Ala Thr Gly Val
    3200                3205                3210

Trp Leu Tyr Val Asp Asp Gln Leu Gln Gln Met Lys Pro His Arg
    3215                3220                3225

Gly Pro Pro Pro Glu Leu Gln Pro Gln Pro Glu Gly Pro Pro Arg
    3230                3235                3240

Leu Leu Leu Gly Gly Leu Pro Glu Ser Gly Thr Ile Tyr Asn Phe
    3245                3250                3255

Ser Gly Cys Ile Ser Asn Val Phe Val Gln Arg Leu Leu Gly Pro
    3260                3265                3270

Gln Arg Val Phe Asp Leu Gln Gln Asn Leu Gly Ser Val Asn Val
    3275                3280                3285

Ser Thr Gly Cys Ala Pro Ala Leu Gln Ala Gln Thr Pro Gly Leu
    3290                3295                3300

Gly Pro Arg Gly Leu Gln Ala Thr Ala Arg Lys Ala Ser Arg Arg
    3305                3310                3315

Ser Arg Gln Pro Ala Arg His Pro Ala Cys Met Leu Pro Pro His
    3320                3325                3330
```

Leu Arg Thr Thr Arg Asp Ser Tyr Gln Phe Gly Gly Ser Leu Ser
3335               3340                3345

Ser His Leu Glu Phe Val Gly Ile Leu Ala Arg His Arg Asn Trp
3350               3355                3360

Pro Ser Leu Ser Met His Val Leu Pro Arg Ser Ser Arg Gly Leu
3365               3370                3375

Leu Leu Phe Thr Ala Arg Leu Arg Pro Gly Ser Pro Ser Leu Ala
3380               3385                3390

Leu Phe Leu Ser Asn Gly His Phe Val Ala Gln Met Glu Gly Leu
3395               3400                3405

Gly Thr Arg Leu Arg Ala Gln Ser Arg Gln Arg Ser Arg Pro Gly
3410               3415                3420

Arg Trp His Lys Val Ser Val Arg Trp Glu Lys Asn Arg Ile Leu
3425               3430                3435

Leu Val Thr Asp Gly Ala Arg Ala Trp Ser Gln Glu Gly Pro His
3440               3445                3450

Arg Gln His Gln Gly Ala Glu His Pro Gln Pro His Thr Leu Phe
3455               3460                3465

Val Gly Gly Leu Pro Ala Ser Ser His Ser Ser Lys Leu Pro Val
3470               3475                3480

Thr Val Gly Phe Ser Gly Cys Val Lys Arg Leu Arg Leu His Gly
3485               3490                3495

Arg Pro Leu Gly Ala Pro Thr Arg Met Ala Gly Val Thr Pro Cys
3500               3505                3510

Ile Leu Gly Pro Leu Glu Ala Gly Leu Phe Phe Pro Gly Ser Gly
3515               3520                3525

Gly Val Ile Thr Leu Asp Leu Pro Gly Ala Thr Leu Pro Asp Val
3530               3535                3540

Gly Leu Glu Leu Glu Val Arg Pro Leu Ala Val Thr Gly Leu Ile
3545               3550                3555

Phe His Leu Gly Gln Ala Arg Thr Pro Pro Tyr Leu Gln Leu Gln
3560               3565                3570

Val Thr Glu Lys Gln Val Leu Leu Arg Ala Asp Asp Gly Ala Gly
3575               3580                3585

Glu Phe Ser Thr Ser Val Thr Arg Pro Ser Val Leu Cys Asp Gly
3590               3595                3600

Gln Trp His Arg Leu Ala Val Met Lys Ser Gly Asn Val Leu Arg
3605               3610                3615

Leu Glu Val Asp Ala Gln Ser Asn His Thr Val Gly Pro Leu Leu
3620               3625                3630

Ala Ala Ala Ala Gly Ala Pro Ala Pro Leu Tyr Leu Gly Gly Leu
3635               3640                3645

Pro Glu Pro Met Ala Val Gln Pro Trp Pro Ala Tyr Cys Gly
3650               3655                3660

Cys Met Arg Arg Leu Ala Val Asn Arg Ser Pro Val Ala Met Thr
3665               3670                3675

Arg Ser Val Glu Val His Gly Ala Val Gly Ala Ser Gly Cys Pro
3680               3685                3690

Ala Ala
3695

<210> SEQ ID NO 2
<211> LENGTH: 1811

<212> TYPE: PRT
<213> ORGANISM: Homo sapiens

<400> SEQUENCE: 2

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Gly Asp Leu Leu Val Gly Arg Ala Asp Arg Leu Thr Ala
    50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Ala Ala Trp Trp Gln Ser Glu Asn
        115                 120                 125

Gly Ile Pro Ala Val Thr Ile Gln Leu Asp Leu Glu Ala Glu Phe His
    130                 135                 140

Phe Thr His His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
            165                 170                 175

Tyr Phe Ser Tyr Asp Cys Gly Ala Asp Phe Pro Gly Val Pro Leu Ala
        180                 185                 190

Pro Pro Arg His Trp Asp Asp Val Val Cys Glu Ser Arg Tyr Ser Glu
    195                 200                 205

Ile Glu Pro Ser Thr Glu Gly Glu Val Ile Tyr Arg Val Leu Asp Pro
210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
            245                 250                 255

Asp Asn Leu Leu Asp Pro Arg Arg Glu Ile Arg Glu Lys Tyr Tyr Tyr
        260                 265                 270

Ala Leu Tyr Glu Leu Val Val Arg Gly Asn Cys Phe Cys Tyr Gly His
    275                 280                 285

Ala Ser Glu Cys Ala Pro Ala Pro Gly Ala Pro Ala His Ala Glu Gly
290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
            325                 330                 335

Glu Asp Gly His Ser His Ala Cys Arg Lys Cys Glu Cys His Gly His
        340                 345                 350

Thr His Ser Cys His Phe Asp Met Ala Val Tyr Leu Ala Ser Gly Asn
    355                 360                 365

Val Ser Gly Gly Val Cys Asp Gly Cys Gln His Asn Thr Ala Gly Arg
370                 375                 380

His Cys Glu Leu Cys Arg Pro Phe Phe Tyr Arg Asp Pro Thr Lys Asp
385                 390                 395                 400

```
Leu Arg Asp Pro Ala Val Cys Arg Ser Cys Asp Cys Asp Pro Met Gly
            405                 410                 415

Ser Gln Asp Gly Gly Arg Cys Asp Ser His Asp Asp Pro Ala Leu Gly
        420                 425                 430

Leu Val Ser Gly Gln Cys Arg Cys Lys Glu His Val Val Gly Thr Arg
            435                 440                 445

Cys Gln Gln Cys Arg Asp Gly Phe Phe Gly Leu Ser Ile Ser Asp Arg
    450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
            485                 490                 495

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
        530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
    610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
            645                 650                 655

Leu Val Pro Lys Asp Asp Arg Ile Gln Gly Thr Leu Gln Pro His Ala
            660                 665                 670

Arg Tyr Leu Ile Phe Pro Asn Pro Val Cys Leu Glu Pro Gly Ile Ser
        675                 680                 685

Tyr Lys Leu His Leu Lys Leu Val Arg Thr Gly Gly Ser Ala Gln Pro
        690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
            725                 730                 735

Ala Leu Glu Arg Gln Ala Thr Phe Glu Arg Tyr Gln Cys His Glu Glu
        740                 745                 750

Gly Leu Val Pro Ser Lys Thr Ser Pro Ser Glu Ala Cys Ala Pro Leu
        755                 760                 765

Leu Ile Ser Leu Ser Thr Leu Ile Tyr Asn Gly Ala Leu Pro Cys Gln
        770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
            805                 810                 815
```

```
Ala Pro Gly Tyr Tyr Gly Phe Gly Pro Thr Gly Cys Gln Ala Cys Gln
            820                 825                 830

Cys Ser His Glu Gly Ala Leu Ser Ser Leu Cys Glu Lys Thr Ser Gly
            835                 840                 845

Gln Cys Leu Cys Arg Thr Gly Ala Phe Gly Leu Arg Cys Asp Arg Cys
            850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
            900                 905                 910

His Gly Asp Pro Arg Leu Pro Tyr Gly Gly Gln Cys Arg Pro Cys Pro
            915                 920                 925

Cys Pro Glu Gly Pro Gly Ser Gln Arg His Phe Ala Thr Ser Cys His
            930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
            965                 970                 975

Ser Arg Pro Gly Gly Arg Cys Gln Leu Cys Glu Cys Ser Gly Asn Ile
            980                 985                 990

Asp Pro Met Asp Pro Asp Ala Cys  Asp Pro His Thr Gly  Gln Cys Leu
            995                 1000                1005

Arg Cys Leu His His Thr Glu  Gly Pro His Cys Ala  His Cys Lys
    1010                1015                1020

Pro Gly Phe His Gly Gln Ala  Ala Arg Gln Ser Cys  His Arg Cys
    1025                1030                1035

Thr Cys Asn Leu Leu Gly Thr  Asn Pro Gln Gln Cys  Pro Ser Pro
    1040                1045                1050

Asp Gln Cys His Cys Asp Pro  Ser Ser Gly Gln Cys  Pro Cys Leu
    1055                1060                1065

Pro Asn Val Gln Gly Pro Ser  Cys Asp Arg Cys Ala  Pro Asn Phe
    1070                1075                1080

Trp Asn Leu Thr Ser Gly His  Gly Cys Gln Pro Cys  Ala Cys His
    1085                1090                1095

Pro Ser Arg Ala Arg Gly Pro  Thr Cys Asn Glu Phe  Thr Gly Gln
    1100                1105                1110

Cys His Cys Arg Ala Gly Phe  Gly Gly Arg Thr Cys  Ser Glu Cys
    1115                1120                1125

Gln Glu Leu His Trp Gly Asp  Pro Gly Leu Gln Cys  His Ala Cys
    1130                1135                1140

Asp Cys Asp Ser Arg Gly Ile  Asp Thr Pro Gln Cys  His Arg Phe
    1145                1150                1155

Thr Gly His Cys Ser Cys Arg  Pro Gly Val Ser Gly  Val Arg Cys
    1160                1165                1170

Asp Gln Cys Ala Arg Gly Phe  Ser Gly Ile Phe Pro  Ala Cys His
    1175                1180                1185

Pro Cys His Ala Cys Phe Gly  Asp Trp Asp Arg Val  Val Gln Asp
    1190                1195                1200

Leu Ala Ala Arg Thr Gln Arg  Leu Glu Gln Arg Ala  Gln Glu Leu
    1205                1210                1215

Gln Gln Thr Gly Val Leu Gly  Ala Phe Glu Ser Ser  Phe Trp His
```

```
                  1220                1225                1230
Met Gln Glu Lys Leu Gly Ile Val Gln Gly Ile Val Gly Ala Arg
    1235                1240                1245

Asn Thr Ser Ala Ala Ser Thr Ala Gln Leu Val Glu Ala Thr Glu
    1250                1255                1260

Glu Leu Arg Arg Glu Ile Gly Glu Ala Thr Glu His Leu Thr Gln
    1265                1270                1275

Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Asp Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
    1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470

Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530

Glu Met Val Ala Thr Arg Val Leu Glu Leu Ser Ile Pro Ala Ser
    1535                1540                1545

Ala Glu Gln Ile Gln His Leu Ala Gly Ala Ile Ala Glu Arg Val
    1550                1555                1560

Arg Ser Leu Ala Asp Val Asp Ala Ile Leu Ala Arg Thr Val Gly
    1565                1570                1575

Asp Val Arg Arg Ala Glu Gln Leu Leu Gln Asp Ala Arg Arg Ala
    1580                1585                1590

Arg Ser Trp Ala Glu Asp Glu Lys Gln Lys Ala Glu Thr Val Gln
    1595                1600                1605

Ala Ala Leu Glu Glu Ala Gln Arg Ala Gln Gly Ile Ala Gln Gly
    1610                1615                1620
```

```
Ala Ile Arg Gly Ala Val Ala Asp Thr Arg Asp Thr Glu Gln Thr
    1625                1630                1635

Leu Tyr Gln Val Gln Glu Arg Met Ala Gly Ala Glu Arg Ala Leu
    1640                1645                1650

Ser Ser Ala Gly Glu Arg Ala Arg Gln Leu Asp Ala Leu Leu Glu
    1655                1660                1665

Ala Leu Lys Leu Lys Arg Ala Gly Asn Ser Leu Ala Ala Ser Thr
    1670                1675                1680

Ala Glu Glu Thr Ala Gly Ser Ala Gln Gly Arg Ala Gln Glu Ala
    1685                1690                1695

Glu Gln Leu Leu Arg Gly Pro Leu Gly Asp Gln Tyr Gln Thr Val
    1700                1705                1710

Lys Ala Leu Ala Glu Arg Lys Ala Gln Gly Val Leu Ala Ala Gln
    1715                1720                1725

Ala Arg Ala Glu Gln Leu Arg Asp Glu Ala Arg Asp Leu Leu Gln
    1730                1735                1740

Ala Ala Gln Asp Lys Leu Gln Arg Leu Gln Glu Leu Glu Gly Thr
    1745                1750                1755

Tyr Glu Glu Asn Glu Arg Ala Leu Glu Ser Lys Ala Ala Gln Leu
    1760                1765                1770

Asp Gly Leu Glu Ala Arg Met Arg Ser Val Leu Gln Ala Ile Asn
    1775                1780                1785

Leu Gln Val Gln Ile Tyr Asn Thr Cys Gln Lys Ser Ser Trp Pro
    1790                1795                1800

Gly Arg Ala Pro Asn Lys Pro Val
    1805                1810

<210> SEQ ID NO 3
<211> LENGTH: 1609
<212> TYPE: PRT
<213> ORGANISM: Homo sapiens

<400> SEQUENCE: 3

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
                20                  25                  30

Ala Gln Ala Ala Met Asp Glu Cys Thr Asp Glu Gly Gly Arg Pro Gln
            35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
        130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
```

-continued

```
            165                 170                 175
Tyr Tyr Ser Gly Ser Cys Glu Asn Thr Tyr Ser Lys Ala Asn Arg Gly
            180                 185                 190
Phe Ile Arg Thr Gly Gly Asp Glu Gln Gln Ala Leu Cys Thr Asp Glu
            195                 200                 205
Phe Ser Asp Ile Ser Pro Leu Thr Gly Gly Asn Val Ala Phe Ser Thr
            210                 215                 220
Leu Glu Gly Arg Pro Ser Ala Tyr Asn Phe Asp Asn Ser Pro Val Leu
225                 230                 235                 240
Gln Glu Trp Val Thr Ala Thr Asp Ile Arg Val Thr Leu Asn Arg Leu
                    245                 250                 255
Asn Thr Phe Gly Asp Glu Val Phe Asn Asp Pro Lys Val Leu Lys Ser
                    260                 265                 270
Tyr Tyr Tyr Ala Ile Ser Asp Phe Ala Val Gly Gly Arg Cys Lys Cys
                    275                 280                 285
Asn Gly His Ala Ser Glu Cys Met Lys Asn Glu Phe Asp Lys Leu Val
            290                 295                 300
Cys Asn Cys Lys His Asn Thr Tyr Gly Val Asp Cys Glu Lys Cys Leu
305                 310                 315                 320
Pro Phe Phe Asn Asp Arg Pro Trp Arg Arg Ala Thr Ala Glu Ser Ala
                    325                 330                 335
Ser Glu Cys Leu Pro Cys Asp Cys Asn Gly Arg Ser Gln Glu Cys Tyr
                    340                 345                 350
Phe Asp Pro Glu Leu Tyr Arg Ser Thr Gly His Gly Gly His Cys Thr
                    355                 360                 365
Asn Cys Gln Asp Asn Thr Asp Gly Ala His Cys Glu Arg Cys Arg Glu
                    370                 375                 380
Asn Phe Phe Arg Leu Gly Asn Asn Glu Ala Cys Ser Ser Cys His Cys
385                 390                 395                 400
Ser Pro Val Gly Ser Leu Ser Thr Gln Cys Asp Ser Tyr Gly Arg Cys
                    405                 410                 415
Ser Cys Lys Pro Gly Val Met Gly Asp Lys Cys Asp Arg Cys Gln Pro
                    420                 425                 430
Gly Phe His Ser Leu Thr Glu Ala Gly Cys Arg Pro Cys Ser Cys Asp
                    435                 440                 445
Pro Ser Gly Ser Ile Asp Glu Cys Asn Ile Glu Thr Gly Arg Cys Val
            450                 455                 460
Cys Lys Asp Asn Val Glu Gly Phe Asn Cys Glu Arg Cys Lys Pro Gly
465                 470                 475                 480
Phe Phe Asn Leu Glu Ser Ser Asn Pro Arg Gly Cys Thr Pro Cys Phe
                    485                 490                 495
Cys Phe Gly His Ser Ser Val Cys Thr Asn Ala Val Gly Tyr Ser Val
            500                 505                 510
Tyr Ser Ile Ser Ser Thr Phe Gln Ile Asp Glu Asp Gly Trp Arg Ala
            515                 520                 525
Glu Gln Arg Asp Gly Ser Glu Ala Ser Leu Glu Trp Ser Ser Glu Arg
            530                 535                 540
Gln Asp Ile Ala Val Ile Ser Asp Ser Tyr Phe Pro Arg Tyr Phe Ile
545                 550                 555                 560
Ala Pro Ala Lys Phe Leu Gly Lys Gln Val Leu Ser Tyr Gly Gln Asn
                    565                 570                 575
Leu Ser Phe Ser Phe Arg Val Asp Arg Arg Asp Thr Arg Leu Ser Ala
                    580                 585                 590
```

```
Glu Asp Leu Val Leu Glu Gly Ala Gly Leu Arg Val Ser Val Pro Leu
            595                 600                 605
Ile Ala Gln Gly Asn Ser Tyr Pro Ser Glu Thr Thr Val Lys Tyr Val
    610                 615                 620
Phe Arg Leu His Glu Ala Thr Asp Tyr Pro Trp Arg Pro Ala Leu Thr
625                 630                 635                 640
Pro Phe Glu Phe Gln Lys Leu Leu Asn Asn Leu Thr Ser Ile Lys Ile
                645                 650                 655
Arg Gly Thr Tyr Ser Glu Arg Ser Ala Gly Tyr Leu Asp Asp Val Thr
            660                 665                 670
Leu Ala Ser Ala Arg Pro Gly Pro Gly Val Pro Ala Thr Trp Val Glu
                675                 680                 685
Ser Cys Thr Cys Pro Val Gly Tyr Gly Gly Gln Phe Cys Glu Met Cys
            690                 695                 700
Leu Ser Gly Tyr Arg Arg Glu Thr Pro Asn Leu Gly Pro Tyr Ser Pro
705                 710                 715                 720
Cys Val Leu Cys Ala Cys Asn Gly His Ser Glu Thr Cys Asp Pro Glu
                        725                 730                 735
Thr Gly Val Cys Asn Cys Arg Asp Asn Thr Ala Gly Pro His Cys Glu
                740                 745                 750
Lys Cys Ser Asp Gly Tyr Tyr Gly Asp Ser Thr Ala Gly Thr Ser Ser
            755                 760                 765
Asp Cys Gln Pro Cys Pro Cys Pro Gly Gly Ser Ser Cys Ala Val Val
            770                 775                 780
Pro Lys Thr Lys Glu Val Val Cys Thr Asn Cys Pro Thr Gly Thr Thr
785                 790                 795                 800
Gly Lys Arg Cys Glu Leu Cys Asp Asp Gly Tyr Phe Gly Asp Pro Leu
                        805                 810                 815
Gly Arg Asn Gly Pro Val Arg Leu Cys Arg Leu Cys Gln Cys Ser Asp
                820                 825                 830
Asn Ile Asp Pro Asn Ala Val Gly Asn Cys Asn Arg Leu Thr Gly Glu
            835                 840                 845
Cys Leu Lys Cys Ile Tyr Asn Thr Ala Gly Phe Tyr Cys Asp Arg Cys
            850                 855                 860
Lys Asp Gly Phe Phe Gly Asn Pro Leu Ala Pro Asn Pro Ala Asp Lys
865                 870                 875                 880
Cys Lys Ala Cys Asn Cys Asn Leu Tyr Gly Thr Met Lys Gln Gln Ser
                885                 890                 895
Ser Cys Asn Pro Val Thr Gly Gln Cys Glu Cys Leu Pro His Val Thr
            900                 905                 910
Gly Gln Asp Cys Gly Ala Cys Asp Pro Gly Phe Tyr Asn Leu Gln Ser
                915                 920                 925
Gly Gln Gly Cys Glu Arg Cys Asp Cys His Ala Leu Gly Ser Thr Asn
            930                 935                 940
Gly Gln Cys Asp Ile Arg Thr Gly Gln Cys Glu Cys Gln Pro Gly Ile
945                 950                 955                 960
Thr Gly Gln His Cys Glu Arg Cys Glu Val Asn His Phe Gly Phe Gly
                        965                 970                 975
Pro Glu Gly Cys Lys Pro Cys Asp Cys His Pro Glu Gly Ser Leu Ser
                980                 985                 990
Leu Gln Cys Lys Asp Asp Gly Arg  Cys Glu Cys Arg Glu  Gly Phe Val
            995                 1000                1005
```

```
Gly Asn Arg Cys Asp Gln Cys Glu Glu Asn Tyr Phe Tyr Asn Arg
1010                1015                1020

Ser Trp Pro Gly Cys Gln Glu Cys Pro Ala Cys Tyr Arg Leu Val
1025                1030                1035

Lys Asp Lys Val Ala Asp His Arg Val Lys Leu Gln Glu Leu Glu
1040                1045                1050

Ser Leu Ile Ala Asn Leu Gly Thr Gly Asp Glu Met Val Thr Asp
1055                1060                1065

Gln Ala Phe Glu Asp Arg Leu Lys Glu Ala Glu Arg Glu Val Met
1070                1075                1080

Asp Leu Leu Arg Glu Ala Gln Asp Val Lys Asp Val Asp Gln Asn
1085                1090                1095

Leu Met Asp Arg Leu Gln Arg Val Asn Asn Thr Leu Ser Ser Gln
1100                1105                1110

Ile Ser Arg Leu Gln Asn Ile Arg Asn Thr Ile Glu Glu Thr Gly
1115                1120                1125

Asn Leu Ala Glu Gln Ala Arg Ala His Val Glu Asn Thr Glu Arg
1130                1135                1140

Leu Ile Glu Ile Ala Ser Arg Glu Leu Glu Lys Ala Lys Val Ala
1145                1150                1155

Ala Ala Asn Val Ser Val Thr Gln Pro Glu Ser Thr Gly Asp Pro
1160                1165                1170

Asn Asn Met Thr Leu Leu Ala Glu Glu Ala Arg Lys Leu Ala Glu
1175                1180                1185

Arg His Lys Gln Glu Ala Asp Asp Ile Val Arg Val Ala Lys Thr
1190                1195                1200

Ala Asn Asp Thr Ser Thr Glu Ala Tyr Asn Leu Leu Leu Arg Thr
1205                1210                1215

Leu Ala Gly Glu Asn Gln Thr Ala Phe Glu Ile Glu Glu Leu Asn
1220                1225                1230

Arg Lys Tyr Glu Gln Ala Lys Asn Ile Ser Gln Asp Leu Glu Lys
1235                1240                1245

Gln Ala Ala Arg Val His Glu Glu Ala Lys Arg Ala Gly Asp Lys
1250                1255                1260

Ala Val Glu Ile Tyr Ala Ser Val Ala Gln Leu Ser Pro Leu Asp
1265                1270                1275

Ser Glu Thr Leu Glu Asn Glu Ala Asn Asn Ile Lys Met Glu Ala
1280                1285                1290

Glu Asn Leu Glu Gln Leu Ile Asp Gln Lys Leu Lys Asp Tyr Glu
1295                1300                1305

Asp Leu Arg Glu Asp Met Arg Gly Lys Glu Leu Glu Val Lys Asn
1310                1315                1320

Leu Leu Glu Lys Gly Lys Thr Glu Gln Gln Thr Ala Asp Gln Leu
1325                1330                1335

Leu Ala Arg Ala Asp Ala Ala Lys Ala Leu Ala Glu Glu Ala Ala
1340                1345                1350

Lys Lys Gly Arg Asp Thr Leu Gln Glu Ala Asn Asp Ile Leu Asn
1355                1360                1365

Asn Leu Lys Asp Phe Asp Arg Arg Val Asn Asp Asn Lys Thr Ala
1370                1375                1380

Ala Glu Glu Ala Leu Arg Lys Ile Pro Ala Ile Asn Gln Thr Ile
1385                1390                1395

Thr Glu Ala Asn Glu Lys Thr Arg Glu Ala Gln Gln Ala Leu Gly
```

```
                1400               1405                1410

Ser Ala Ala Ala Asp Ala Thr Glu Ala Lys Asn Lys Ala His Glu
    1415                1420                1425

Ala Glu Arg Ile Ala Ser Ala Val Gln Lys Asn Ala Thr Ser Thr
        1430                1435                1440

Lys Ala Glu Ala Glu Arg Thr Phe Ala Glu Val Thr Asp Leu Asp
    1445                1450                1455

Asn Glu Val Asn Asn Met Leu Lys Gln Leu Gln Glu Ala Glu Lys
    1460                1465                1470

Glu Leu Lys Arg Lys Gln Asp Asp Ala Asp Gln Asp Met Met Met
    1475                1480                1485

Ala Gly Met Ala Ser Gln Ala Ala Gln Glu Ala Glu Ile Asn Ala
    1490                1495                1500

Arg Lys Ala Lys Asn Ser Val Thr Ser Leu Leu Ser Ile Ile Asn
    1505                1510                1515

Asp Leu Leu Glu Gln Leu Gly Gln Leu Asp Thr Val Asp Leu Asn
    1520                1525                1530

Lys Leu Asn Glu Ile Glu Gly Thr Leu Asn Lys Ala Lys Asp Glu
    1535                1540                1545

Met Lys Val Ser Asp Leu Asp Arg Lys Val Ser Asp Leu Glu Asn
    1550                1555                1560

Glu Ala Lys Lys Gln Glu Ala Ala Ile Met Asp Tyr Asn Arg Asp
    1565                1570                1575

Ile Glu Glu Ile Met Lys Asp Ile Arg Asn Leu Glu Asp Ile Arg
    1580                1585                1590

Lys Thr Leu Pro Ser Gly Cys Phe Asn Thr Pro Ser Ile Glu Lys
    1595                1600                1605

Pro

<210> SEQ ID NO 4
<211> LENGTH: 555
<212> TYPE: PRT
<213> ORGANISM: Homo sapiens

<400> SEQUENCE: 4

Met Asp Trp Val Ile Pro Pro Ile Ser Cys Pro Glu Asn Glu Lys Gly
1               5                   10                  15

Pro Phe Pro Lys Asn Leu Val Gln Ile Lys Ser Asn Lys Asp Lys Glu
            20                  25                  30

Gly Lys Val Phe Tyr Ser Ile Thr Gly Gln Gly Ala Asp Thr Pro Pro
        35                  40                  45

Val Gly Val Phe Ile Ile Glu Arg Glu Thr Gly Trp Leu Lys Val Thr
    50                  55                  60

Glu Pro Leu Asp Arg Glu Arg Ile Ala Thr Tyr Thr Leu Phe Ser His
65                  70                  75                  80

Ala Val Ser Ser Asn Gly Asn Ala Val Glu Asp Pro Met Glu Ile Leu
                85                  90                  95

Ile Thr Val Thr Asp Gln Asn Asp Asn Lys Pro Glu Phe Thr Gln Glu
            100                 105                 110

Val Phe Lys Gly Ser Val Met Glu Gly Ala Leu Pro Gly Thr Ser Val
        115                 120                 125

Met Glu Val Thr Ala Thr Asp Ala Asp Asp Asp Val Asn Thr Tyr Asn
    130                 135                 140

Ala Ala Ile Ala Tyr Thr Ile Leu Ser Gln Asp Pro Glu Leu Pro Asp
```

```
           145                 150                 155                 160
Lys Asn Met Phe Thr Ile Asn Arg Asn Thr Gly Val Ile Ser Val Val
                    165                 170                 175

Thr Thr Gly Leu Asp Arg Glu Ser Phe Pro Thr Tyr Thr Leu Val Val
                    180                 185                 190

Gln Ala Ala Asp Leu Gln Gly Glu Gly Leu Ser Thr Ala Thr Ala
                195                 200                 205

Val Ile Thr Val Thr Asp Thr Asn Asp Asn Pro Pro Ile Phe Asn Pro
210                 215                 220

Thr Thr Tyr Lys Gly Gln Val Pro Glu Asn Glu Ala Asn Val Val Ile
225                 230                 235                 240

Thr Thr Leu Lys Val Thr Asp Ala Asp Ala Pro Asn Thr Pro Ala Trp
                    245                 250                 255

Glu Ala Val Tyr Thr Ile Leu Asn Asp Asp Gly Gly Gln Phe Val Val
                260                 265                 270

Thr Thr Asn Pro Val Asn Asn Asp Gly Ile Leu Lys Thr Ala Lys Gly
                    275                 280                 285

Leu Asp Phe Glu Ala Lys Gln Gln Tyr Ile Leu His Val Ala Val Thr
    290                 295                 300

Asn Val Val Pro Phe Glu Val Ser Leu Thr Thr Ser Thr Ala Thr Val
305                 310                 315                 320

Thr Val Asp Val Leu Asp Val Asn Glu Ala Pro Ile Phe Val Pro Pro
                    325                 330                 335

Glu Lys Arg Val Glu Val Ser Glu Asp Phe Gly Val Gly Gln Glu Ile
                340                 345                 350

Thr Ser Tyr Thr Ala Gln Glu Pro Asp Thr Phe Met Glu Gln Lys Ile
        355                 360                 365

Thr Tyr Arg Ile Trp Arg Asp Thr Ala Asn Trp Leu Glu Ile Asn Pro
            370                 375                 380

Asp Thr Gly Ala Ile Ser Thr Arg Ala Glu Leu Asp Arg Glu Asp Phe
385                 390                 395                 400

Glu His Val Lys Asn Ser Thr Tyr Thr Ala Leu Ile Ile Ala Thr Asp
                405                 410                 415

Asn Gly Ser Pro Val Ala Thr Gly Thr Gly Thr Leu Leu Leu Ile Leu
                420                 425                 430

Ser Asp Val Asn Asp Asn Ala Pro Ile Pro Glu Pro Arg Thr Ile Phe
            435                 440                 445

Phe Cys Glu Arg Asn Pro Lys Pro Gln Val Ile Asn Ile Ile Asp Ala
450                 455                 460

Asp Leu Pro Pro Asn Thr Ser Pro Phe Thr Ala Glu Leu Thr His Gly
465                 470                 475                 480

Ala Ser Ala Asn Trp Thr Ile Gln Tyr Asn Asp Pro Thr Gln Glu Ser
                485                 490                 495

Ile Ile Leu Lys Pro Lys Met Ala Leu Glu Val Gly Asp Tyr Lys Ile
            500                 505                 510

Asn Leu Lys Leu Met Asp Asn Gln Asn Lys Asp Gln Val Thr Thr Leu
            515                 520                 525

Glu Val Ser Val Cys Asp Cys Glu Gly Ala Ala Gly Val Cys Arg Lys
        530                 535                 540

Ala Gln Pro Val Glu Ala Gly Leu Gln Ile Pro
545                 550                 555

<210> SEQ ID NO 5
```

```
<211> LENGTH: 4024
<212> TYPE: DNA
<213> ORGANISM: Homo sapiens

<400> SEQUENCE: 5
caccgctatt gtgcggggga agatgtagca gcttcttctc cgaaccaacc ctttgccttc        60
ggacttctcc ggggccagca gccgcccgac caggggcccg ggccacggg ctcagccgac       120 gaccatgggc tccgtgtcca accagcagtt tgcaggtggc tgcgccaagg cggcagaaga       180
ggcgcccgag gaggcgccgg aggacgcggc ccggcggcg gacgagcctc agctgctgca       240
cggtgcgggc atctgtaagt ggttcaacgt gcgcatgggg ttcggcttcc tgtccatgac       300
cgcccgcgcc ggggtcgcgc tcgaccccca gtggatgtc tttgtgcacc agagtaagct       360
gcacatggaa gggttccgga gcttgaagga gggtgaggca gtggagttca cctttaagaa       420
gtcagccaag ggtctggaat ccatccgtgt caccggacct ggtggagtat tctgtattgg       480
gagtgagagg cggccaaaag gaaagagcat gcagaagcgc agatcaaaag gagacaggtg       540
ctacaactgt ggaggtctag atcatcatgc caaggaatgc aagctgccac cccagcccaa       600
gaagtgccac ttctgccaga gcatcagcca tatggtagcc tcatgtccgc tgaaggccca       660
gcagggccct agtgcacagg gaaagccaac ctactttcga gaggaagaag aagaaatcca       720
cagccctacc ctgctcccgg aggcacagaa ttgagccaca tgggtgggg ctattctttt       780 tgctatcagg aagttttgag gagcaggcag agtggagaaa gtgggaatag ggtgcattgg       840
ggctagttgg cactgccatg tatctcaggc ttgggttcac accatcaccc tttcttccct       900
ctaggtgggg ggaaagggtg agtcaaagga actccaacca tgctctgtcc aaatgcaagt       960
gagggttctg ggggcaacca ggaggggga atcaccctac aacctgcata ctttgagtct      1020
ccatccccag aatttccagc ttttgaaagt ggcctggata gggaagttgt tttcctttta      1080
aagaaggata tataataatt cccatgccag agtgaaatga ttaagtataa gaccagattc      1140
atggagccaa gccactacat tctgtggaag gagatctctc aggagtaagc attgttttt       1200 tttcacatct tgtatcctca tacccacttt tgggataggg tgctggcagc tgtcccaagc      1260
aatgggtaat gatgatggca aaagggtgt ttgggggaac agctgcagac ctgctgctct      1320
atgctcaccc ccgccccatt ctgggccaat gtgattttat ttatttgctc ccttggatac      1380
tgcaccttgg gtcccacttt ctccaggatg ccaactgcac tagctgtgtg cgaatgacgt      1440
atcttgtgca tttaactttt ttttccttaa tataaatatt ctggttttgt attttgtat      1500 attttaatct aaggccctca tttcctgcac tgtgttctca ggtacatgag caatctcagg      1560
gatagccagc agcagctcca ggtctgcgca gcaggaatta cttttgttg tttttgccac      1620 cgtggagagc aactatttgg agtgcacagc ctattgaact acctcatttt tgccaataag      1680
agctggcttt tctgccatag tgtcctcttg aaaccccctc tgccttgaaa atgttttatg      1740
ggagactagg ttttaactgg gtggccccat gacttgattg ccttctactg gaagattggg      1800
aattagtcta aacaggaaat ggtggtacac agaggctagg agaggctggg cccggtgaaa      1860
aggccagaga gcaagccaag attaggtgag ggttgtctaa tcctatggca caggacgtgc      1920
tttacatctc cagatctgtt cttcaccaga ttaggtagg cctaccatgt gccacagggt      1980
gtgtgtgtgt ttgtaaaact agagttgcta aggataagtt taaagaccaa taccctgta      2040 cttaatcctg tgctgtcgag ggatggatat atgaagtaag gtgagatcct taacctttca      2100
aaattttcgg gttccaggga gacacacaag cgagggtttt gtggtgcctg gagcctgtgt      2160
cctgccctgc tacagtagtg attaatagtg tcatggtagc taaaggagaa aaagggggtt      2220
```

```
tcgtttacac gctgtgagat caccgcaaac ctaccttact gtgttgaaac gggacaaatg    2280
caatagaacg cattgggtgg tgtgtgtctg atcctgggtt cttgtctccc ctaaatgctg    2340 cccccccaagt tactgtattt gtctgggctt tgtaggactt cactacgttg attgctaggt   2400
ggcctagttt gtgtaaatat aatgtattgg tcttctccg tgttctttgg gggttttgtt    2460
tacaaacttc tttttgtatt gagagaaaaa tagccaaagc atctttgaca gaaggttctg    2520
caccaggcaa aaagatctga acattagtt tgggggggccc tcttcttaaa gtggggatct    2580
tgaaccatcc tttcttttgt attccccttc ccctattacc tattagacca gatcttctgt    2640
cctaaaaact tgtcttctac cctgccctct tttctgttca ccccccaaaag aaaacttaca   2700 cacccacaca catacacatt tcatgcttgg agtgtctcca caactcttaa atgatgtatg    2760
caaaaatact gaagctagga aaaccctcca tcccttgttc ccaacctcct aagtcaagac    2820
cattaccatt tctttctttc tttttttttt tttttaaaa tggagtctca ctgtgtcacc     2880
caggctggag tgcagtggca tgatcggctc actgcagcct ctgcctcttg ggttcaagtg    2940
attctcctgc ctcagcctcc tgagtagctg ggatttcagg caccccgccac actcagctaa   3000 ttttttgtatt tttagtagag acggggtttc accatgttgt ccaggctggt ctggaactcc   3060
tgacctcagg tgatctgccc accttggctt cccaaagtgc tgggattaca ggcatgagcc    3120
accatgctgg gccaaccatt tcttggtgta ttcatgccaa acacttaaga cactgctgta    3180
gcccaggcgc ggtggctcac acctgtaatc ccagcacttt ggaaggctga ggcgggcgga   3240
tcacaaggtc acgagttcaa aactatcctg gccaacacag tgaaaccccg tctctactaa    3300
aatacaaaaa aattagccgg gtgtggtggt gcatgccttt agtcctagct attcaggagg   3360
ctgaggcagg ggaatcgctt gaacccgaga ggcagaggtt gcagtgagct gagatcgcac    3420
cactgcactc cagcctggtt acagagcaag actctgtctc aaacaaaaca aaacaaaaca   3480
aaaacacact actgtatttt ggatggatca aacctcctta attttaatttt ctaatcctaa   3540 agtaaagaga tgcaattggg ggccttccat gtagaaagtg gggtcaggag gccaagaaag    3600
ggaatatgaa tgtatatcca agtcactcag gaacttttat gcaggtgcta gaaactttat    3660
gtcaaagtgg ccacaagatt gtttaatagg agacgaacga atgtaactcc atgtttactg   3720
ctaaaaacca aagctttgtg taaaatcttg aatttatggg gcgggagggt aggaaagcct    3780
gtacctgtct gttttttttcc tgatcctttt ccctcattcc tgaactgcag gagactgagc    3840 cccctttgggc tttggtgacc ccatcactgg ggtgtgttta tttgatggtt gattttgctg    3900
tactgggtac ttccttttccc attttctaat catttttttaa cacaagctga ctcttcccctt   3960 cccttctcct ttccctggga aaatacaatg aataaataaa gacttattgg tacgcaaact   4020
gtca                                                                 4024

<210> SEQ ID NO 6
<211> LENGTH: 1430
<212> TYPE: DNA
<213> ORGANISM: Homo sapiens

<400> SEQUENCE: 6 agagagggt tgagtagtcc cttcgcaagc cctcatttca ccaggccccc ggcttggggc       60
gccttccttc cccatggcgg gacacctggc ttcggatttc gccttctcgc cccctccagg     120
tggtggaggt gatgggccag gggggccgga gccgggctgg gttgatcctc ggacctggct     180
aagcttccaa ggccctcctg gagggccagg aatcgggccg ggggttgggc caggctctga     240
```

```
ggtgtggggg attccccat gccccgcc gtatgagttc tgtgggggga tggcgtactg      300
tgggccccag gttggagtgg ggctagtgcc ccaaggcggc ttggagacct ctcagcctga    360
gggcgaagca ggagtcgggg tggagagcaa ctccgatggg gcctcccgg agccctgcac    420 cgtcacccct ggtgccgtga agctggagaa ggagaagctg agcaaaaacc cggaggagtc    480
ccaggacatc aaagctctgc agaaagaact cgagcaattt gccaagctcc tgaagcagaa    540
gaggatcacc ctgggatata cacaggccga tgtgggctc accctggggg ttctatttgg     600
gaaggtattc agccaaacga ccatctgccg cttttgaggct ctgcagctta gcttcaagaa    660
catgtgtaag ctgcggccct tgctgcagaa gtgggtggag aagctgaca acaatgaaaa     720 tcttcaggag atatgcaaag cagaaaccct cgtgcaggcc cgaaagagaa agcgaaccag    780
tatcgagaac cgagtgagag gcaacctgga gaatttgttc ctgcagtgcc cgaaacccac     840
actgcagcag atcagccaca tcgcccagca gcttgggctc gagaaggatg tggtccgagt   900
gtggttctgt aaccgcgcc agaagggcaa gcgatcaagc agcgactatg cacaacgaga   960 ggatttgag gctgctgggt ctcctttctc agggggacca gtgtcctttc ctctggcccc   1020
agggccccat tttggtaccc caggctatgg gagccctcac ttcactgcac tgtactcctc   1080 ggtcccttc cctgaggggg aagcctttcc ccctgtctcc gtcaccactc tgggctctcc    1140
catgcattca aactgaggtg cctgcccttc taggaatggg ggacaggggg aggggaggag   1200
ctagggaaag aaaacctgga gtttgtgcca gggttttgg gattaagttc ttcattcact    1260
aaggaaggaa ttgggaacac aaagggtggg ggcaggggag tttggggcaa ctggttggag   1320
ggaaggtgaa gttcaatgat gctcttgatt ttaatcccac atcatgtatc acttttttct    1380
taaataaaga agcctgggac acagtagata gacacactta aaaaaaaaa                1430

<210> SEQ ID NO 7
<211> LENGTH: 2520
<212> TYPE: DNA
<213> ORGANISM: Homo sapiens

<400> SEQUENCE: 7
ggatggttgt ctattaactt gttcaaaaaa gtatcaggag ttgtcaaggc agagaagaga     60
gtgtttgcaa aagggggaaa gtagtttgct gcctctttaa gactaggact gagagaaaga    120
agaggagaga gaaagaaagg gagagaagtt tgagccccag gcttaagcct ttccaaaaaa    180
taataataac aatcatcggc ggcggcagga tcggccagag gaggagggaa gcgcttttt    240 tgatcctgat tccagttttgc ctctctcttt ttttcccccca aattattctt cgcctgattt   300
tcctcgcgga gccctgcgct cccgacaccc ccgcccgcct cccctcctcc tctccccccg    360
cccgcgggcc cccaaagtc ccggccgggc cgagggtcgg cggccgccgg cgggccgggc    420
ccgcgcacag cgcccgcatg tacaacatga tggagacgga gctgaagccg ccgggcccgc    480
agcaaacttc gggggggcggc ggcggcaact ccaccgcggc ggcggccggc ggcaaccaga    540
aaaacagccc ggaccgcgtc aagcggccca tgaatgcctt catggtgtgg tcccgcgggc   600
agcggcgcaa gatggcccag gagaaccca agatgcacaa ctcggagatc agcaagcgcc   660
tgggcgccga gtgaaactt ttgtcggaga cggagaagcg gccgttcatc gacgaggcta    720
agcggctgcg agcgctgcac atgaaggagc acccggatta taatacccgg ccccggcgga    780
aaaccaagac gctcatgaag aaggataagt acacgctgcc cggcgggctg ctggcccccg    840
gcggcaatag catggcgagc gggtcggg tgggcgccgg cctgggcgcg ggcgtgaacc    900
agcgcatgga cagttacgcg cacatgaacg gctggagcaa cggcagctac agcatgatgc    960
```

```
aggaccagct gggctacccg cagcacccgg gcctcaatgc gcacggcgca gcgcagatgc    1020
agcccatgca ccgctacgac gtgagcgccc tgcagtacaa ctccatgacc agctcgcaga    1080
cctacatgaa cggctcgccc acctacagca tgtcctactc gcagcagggc acccctggca    1140
tggctcttgg ctccatgggt tcggtggtca agtccgaggc cagctccagc cccctgtgg     1200 ttacctcttc ctcccactcc agggcgccct gccaggccgg ggacctccgg gacatgatca    1260
gcatgtatct ccccggcgcc gaggtgccgg aacccgccgc ccccagcaga cttcacatgt    1320
cccagcacta ccagagcggc ccggtgcccg gcacggccat taacggcaca ctgcccctct    1380
cacacatgtg agggccggac agcgaactgg agggggggaga attttcaaa gaaaaacgag     1440 ggaaatggga ggggtgcaaa agaggagagt aagaaacagc atggagaaaa cccggtacgc    1500 tcaaaagaa aaggaaaaa aaaaaatccc atcacccaca gcaaatgaca gctgcaaaag      1560
agaacaccaa tcccatccac actcacgcaa aaccgcgat gccgacaaga aaactttat      1620 gagagagatc ctggacttct tttgggga ctatttttgt acagaaaaa cctggggagg       1680 gtggggaggg cggggaatg gaccttgtat agatctggag gaaagaaagc tacgaaaaac    1740 ttttaaaag ttctagtggt acggtaggag ctttgcagga gtttgcaaa agtctttacc      1800 aataatattt agagctagtc tccaagcgac gaaaaaaatg ttttaatatt tgcaagcaac    1860
ttttgtacag tatttatcga gataaacatg gcaatcaaaa tgtccattgt ttataagctg    1920
agaatttgcc aatattttc aaggagaggc ttcttgctga ttttgattc tgcagctgaa      1980 atttaggaca gttgcaaacg tgaaagaag aaaattattc aaatttggac attttaattg    2040
tttaaaaatt gtacaaaagg aaaaaattag aataagtact ggcgaaccat ctctgtggtc    2100
ttgtttaaaa agggcaaaag ttttagactg tactaaattt tataacttac tgttaaaagc    2160
aaaaatggcc atgcaggttg acaccgttgg taatttataa tagcttttgt tcgatcccaa    2220 cttttccattt tgttcagata aaaaaaacca tgaaattact gtgtttgaaa tattttctta    2280
tggtttgtaa tatttctgta aatttattgt gatatttaa ggttttcccc cctttatttt      2340
ccgtagttgt attttaaaag attcggctct gtattatttg aatcagtctg ccagaatcc     2400 atgtatatat ttgaactaat atcatcctta taacaggtac attttcaact taagtttta     2460 ctccattatg cacagtttga gataaataaa tttttgaaat atggacactg aaaaaaaaaa    2520
```

<210> SEQ ID NO 8
<211> LENGTH: 2078
<212> TYPE: DNA
<213> ORGANISM: Homo sapiens

<400> SEQUENCE: 8

```
atgaccctct ccggcggcgg cagcgccagc gacatgtccg ccagacggt gctgacggcc     60 gaggacgtgg acatcgatgt ggtgggcgag ggcgacgacg ggctggaaga gaaggacagc    120
gacgcaggtt gcgatagccc cgcggggccg ccggagctgc cctgacga gcggacgag      180 gtgcccccgg cggcacccca tcacggacag cctcagccgc cccaccagca gcccctgaca    240
ttgcccaagg aggcggccgg agccggggcc ggaccggggg gcgacgtggg cgcgccggag    300
gcggacggct gcaagggcgg tgttggcggc gaggaggggcg gcgcgagcgg cggcgggcct    360
ggcgcgggca gcggttcggc gggaggcctg gccccgagca agcccaagaa cagcctagtg    420
aagccgcctt actcgtacat cgcgctcatc accatggcca tcctgcagag cccgcagaag    480
aagctgaccc tgagcggcat ctgcgagttc atcagcaacc gcttcccctta ctacagggag    540
```

-continued

| | |
|---|---|
| aagttccccg cctggcagaa cagcatccgc cacaacctct cactcaacga ctgcttcgtc | 600 |
| aagatccccc gcgagccggg caacccgggc aagggcaact actggaccct ggacccgcag | 660 |
| tccgaggaca tgttcgacaa cggcagcttc ctgcggcgcc ggaaacgctt caagcgccac | 720 |
| cagcaggagc acctgcgcga gcagacggcg ctcatgatgc agagcttcgg cgcttacagc | 780 |
| ctggcggcgg cggccggcgc cgcgggaccc tacggccgcc cctacggcct gcaccctgcg | 840 |
| gcggcggccg gtgcctattc gcacccggca gcggcggcgg ccgcggctgc tgcggcggcg | 900 |
| ctccagtacc cgtacgcgct gccgccggtg gcaccggtgc tgcctcccgc tgtgccgctg | 960 |
| ctgccctcgg gcgagctggg ccgcaaagcg gccgccttcg gctcacagct cggcccgggc | 1020 |
| ctgcagctgc agctcaatag cctgggcgcc gccgcggccg ctgcgggcac agcgggcgcc | 1080 |
| gcgggcacca ccgcgtcgct catcaagtcc gagccaagcg cgcggccgtc gttcagcatc | 1140 |
| gagaacatca taggtggggg ccccgcggct cctgggggct cggcggtggg cgctggggtc | 1200 |
| gccggcggca ctgggggttc aggggcggc agcacggcgc agtcgtttct gcggccaccc | 1260 |
| gggaccgtgc agtcggcagc gctcatggcc acccaccaac cgctgtcgct gagccggacg | 1320 |
| actgccacca tcgcgcccat tcttagcgtg ccactctccg acagtttcct gcagcccgca | 1380 |
| gcctcggccg ccgccgctgc tgcggccgcc gctcaagcca aatggccggc gcaataggga | 1440 |
| cgcgccaatg gccgggaccc agggtccggc ggcggcctcg agcaacaaat gcacctccag | 1500 |
| gctgcgcgcc ctgtcccaag cccggtcccg gtcccgctgc ccaatcctgg actctgcctc | 1560 |
| tccccaattt cctttcccct gagccccaa cgcctacctt ccgcggcctc catccctcg | 1620 |
| cgcacaccta agctggtcga gcaaactcac cgcgcgcccg ccgggatag ctttccatac | 1680 |
| aggtaaaacc gaaaaccgaa ttttccaaaa atgcacccg acggcgcctg ctcttagtac | 1740 |
| cgtggggatg ggagggaaat tctttgtata tatttgtaaa aaaattattg actttccttt | 1800 |
| tggggttttt atttttttaa gaaaaacaa attccgtaga tttagagctc tgaactttca | 1860 |
| ttttttttga aggttcactc tccgaagttt tatctgagaa agaatgtat agagacgttg | 1920 |
| ggagatttta aatataaaaa attttcaaaa aggcaaaaag tgtcattcta ttataaagt | 1980 |
| ctgtttatat atgaatgaat atatatggta ttctaaatgt tattccatcg tgttgtacac | 2040 |
| aactttgtaa ataaattttt aaaatgccaa aaaaaaaa | 2078 |

<210> SEQ ID NO 9
<211> LENGTH: 2103
<212> TYPE: DNA
<213> ORGANISM: Homo sapiens

<400> SEQUENCE: 9

| | |
|---|---|
| ttcattataa atctagagac tccaggattt taacgttctg ctggactgag ctggttgcct | 60 |
| catgttatta tgcaggcaac tcactttatc ccaatttctt gatactttc cttctggagg | 120 |
| tcctatttct ctaacatctt ccagaaaagt cttaaagctg ccttaacctt ttttccagtc | 180 |
| cacctcttaa atttttcct cctcttcctc tatactaaca tgagtgtgga tccagcttgt | 240 |
| ccccaaagct tgccttgctt tgaagcatcc gactgtaaag aatcttcacc tatgcctgtg | 300 |
| atttgtgggc ctgaagaaaa ctatccatcc ttgcaaatgt cttctgctga gatgcctcac | 360 |
| acggagactg tctctcctct tccttcctcc atggatctgc ttattcagga cagccctgat | 420 |
| tcttccacca gtcccaaagg caaacaaccc acttctgcag agaagagtgt cgcaaaaaag | 480 |
| gaagacaagg tccggtcaa gaaacagaag accagaactg tgttctcttc cacccagctg | 540 |
| tgtgtactca atgatagatt tcagagacag aaatacctca gcctccagca gatgcaagaa | 600 |

```
ctctccaaca tcctgaacct cagctacaaa caggtgaaga cctggttcca gaaccagaga      660
atgaaatcta agaggtggca gaaaaacaac tggccgaaga atagcaatgg tgtgacgcag      720
aaggcctcag cacctaccta ccccagcctt tactcttcct accaccaggg atgcctggtg      780
aacccgactg ggaaccttcc aatgtggagc aaccagacct ggaacaattc aacctggagc      840
aaccagaccc agaacatcca gtcctggagc aaccactcct ggaacactca gacctggtgc      900
acccaatcct ggaacaatca ggcctggaac agtcccttct ataactgtgg agaggaatct      960
ctgcagtcct gcatgcagtt ccagccaaat tctcctgcca gtgacttgga ggctgccttg     1020
gaagctgctg gggaaggcct taatgtaata cagcagacca ctaggtattt tagtactcca     1080
caaaccatgg atttattcct aaactactcc atgaacatgc aacctgaaga cgtgtgaaga     1140
tgagtgaaac tgatattact caatttcagt ctggacactg gctgaatcct tcctctcccc     1200
tcctcccatc cctcatagga ttttcttgt ttggaaacca cgtgttctgg tttccatgat     1260
gcccatccag tcaatctcat ggagggtgga gtatggttgg agcctaatca gcgaggtttc     1320
tttttttttt ttttcctat tggatcttcc tggagaaaat acttttttt tttttttttt     1380 tgaaacggag tcttgctctg tcgcccaggc tggagtgcag tggcgcggtc ttggctcact     1440
gcaagctccg tctcccgggt tcacgccatt ctcctgcctc agcctcccga gcagctggga     1500
ctacaggcgc cgccacctc gcccggctaa tattttgtat ttttagtaga acgggggttt     1560
cactgtgtta gccaggatgg tctcgatctc ctgaccttgt gatccacccg cctcggcctc     1620
cctaacagct gggatttaca ggcgtgagcc accgcgccct gcctagaaaa gacatttaa     1680 taaccttggc tgccgtctct ggctatagat aagtagatct aatactagtt tggatatctt     1740
tagggtttag aatctaacct caagaataag aaatacaagt acaaattggt gatgaagatg     1800
tattcgtatt gtttgggatt gggaggcttt gcttattttt taaaaactat tgaggtaaag     1860
ggttaagctg taacatactt aattgatttc ttaccgtttt tggctctgtt ttgctatatc     1920
ccctaatttg ttggttgtgc taatctttgt agaaagaggt ctcgtatttg ctgcatcgta     1980
atgacatgag tactgcttta gttggtttaa gttcaaatga atgaaacaac tattttcct      2040 ttagttgatt ttaccctgat ttcaccgagt gtttcaatga gtaaatatac agcttaaaca     2100
taa                                                                  2103
```

<210> SEQ ID NO 10
<211> LENGTH: 6007
<212> TYPE: DNA
<213> ORGANISM: Homo sapiens

<400> SEQUENCE: 10

```
agccgcgcag acgccgccca ggacgcagcc gccgccgccg ccgctcctct gccactggct       60
ctgcgcccca gcccggctct gctgcagcgg cagggaggaa gagccgccgc agcgcgactc      120
gggagccccg ggccacagcc tggcctccgg agccacccac aggcctcccc gggcggcgcc      180
cacgctccta ccgcccggac gcgcggatcc tccgccggca ccgcagccac ctgctcccgg      240
cccagaggcg acgacacgat gcgctgcgcg ctggcgctct cggcgctgct gctactgttg      300
tcaacgccgc cgctgctgcc gtcgtcgccg tcgccgtcgc gtcgccctc ccagaatgca      360 acccagacta ctacggactc atctaacaaa acagcaccga ctccagcatc cagtgtcacc      420
atcatggcta cagatacagc ccagcagagc acagtcccca cttccaaggc caacgaaatc      480
ttggcctcgg tcaaggcgac caccccttggt gtatccagtg actcaccggg gactacaacc      540
```

```
ctggctcagc aagtctcagg cccagtcaac actaccgtgg ctagaggagg cggctcaggc     600
aaccctacta ccaccatcga gagccccaag agcacaaaaa gtgcagacac cactacagtt     660
gcaacctcca cagccacagc taaacctaac accacaagca gccagaatgg agcagaagat     720
acaacaaact ctgggggaa aagcagccac agtgtgacca cagacctcac atccactaag      780
gcagaacatc tgacgacccc tcaccctaca agtccactta gccccgaca acccacttcg      840
acgcatcctg tggccacccc aacaagctcg ggacatgacc atcttatgaa aatttcaagc     900
agttcaagca ctgtggctat ccctggctac accttcacaa gcccggggat gaccaccacc     960
ctactagaga cagtgtttca ccatgtcagc caggctggtc ttgaactcct gacctcgggt    1020
gatctgccca ccttggcctc ccaaagtgct gggattacag cgtcatcggt tatctcgcaa    1080
agaactcaac agacctccag tcagatgcca gccagctcta cggccccttc ctcccaggag    1140
acagtgcagc ccacgagccc ggcaacggca ttgagaacac ctaccctgcc agagaccatg    1200
agctccagcc ccacagcagc atcaactacc caccgatacc ccaaaacacc ttctcccact    1260
gtggctcatg agagtaactg ggcaaagtgt gaggatcttg agacacagac acagagtgag    1320
aagcagctcg tcctgaacct cacaggaaac accctctgtg caggggcgc ttcggatgag     1380
aaattgatct cactgatatg ccgagcagtc aaagccacct tcaacccggc caagataag     1440
tgcggcatac ggctggcatc tgttccagga agtcagaccg tggtcgtcaa agaaatcact    1500
attcacacta agctccctgc caaggatgtg tacgagcggc tgaaggacaa atgggatgaa    1560
ctaaaggagg caggggtcag tgacatgaag ctagggacc aggggccacc ggaggaggcc     1620
gaggaccgct tcagcatgcc cctcatcatc accatcgtct gcatggcatc attcctgctc    1680
ctcgtggcgg ccctctatgg ctgctgccac cagcgcctct cccagaggaa ggaccagcag    1740
cggctaacag aggagctgca gacagtggag aatggttacc atgacaaccc aacactggaa    1800
gtgatggaga cctcttctga gatgcaggag aagaaggtgg tcagcctcaa cggggagctg    1860
ggggacagct ggatcgtccc tctggacaac ctgaccaagg acgacctgga tgaggaggaa    1920
gacacacacc tctagtccgg tctgccggtg gcctccagca gcaccacaga gctccagacc    1980
aaccacccca gtgccgttt ggatggggaa gggaaagact ggggagggag agtgaactcc      2040
gagggtgtc ccctcccaat cccccaggg ccttaatttt tccttttca acctgaacaa        2100
atcacattct gtccagattc ctcttgtaaa ataacccact agtgcctgag ctcagtgctg     2160
ctggatgatg agggagatca agaaaaagcc acgtaaggga ctttatagat gaactagtgg    2220
aatcccttca ttctgcagtg agattgccga gacctgaaga gggtaagtga cttgcccaag    2280
gtcagagcca cttggtgaca gagccaggat gagaacaaag attccatttg caccatgcca    2340
cactgctgtg ttcacatgtg ccttccgtcc agagcagtcc cggcagggg tgaaactcca     2400
gcaggtggct gggctggaaa ggagggcagg gctacatcct ggctcggtgg atctgacga    2460
cctgaaagtc cagctcccaa gttttccttc tcctacccca gcctcgtgta cccatcttcc    2520
caccctctat gttcttaccc ctccctacac tcagtgtttg ttcccactta ctctgtcctg    2580
gggcctctgg gattagcaca ggttattcat aaccttgaac cccttgttct ggattcggat    2640
tttctcacat ttgcttcgtg agatgggggc ttaacccaca caggtctccg tgcgtgaacc    2700
aggtctgctt aggggacctg cgtgcaggtg aggagagaag gggacactcg agtccaggct    2760
ggtatctcag ggcagctgat gaggggtcag caggaacact ggcccattgc ccctggcact    2820
ccttgcagag gccacccacg atcttctttg ggcttccatt tccaccaggg actaaaatct    2880
gctgtagcta gtgagagcag cgtgttcctt ttgttgttca ctgctcagct gatgggagtg    2940
```

```
attccctgag acccagtatg aaagagcagt ggctgcagga gaggccttcc cggggccccc    3000
catcagcgat gtgtcttcag agacaatcca ttaaagcagc caggaaggac aggctttccc    3060
ctgtatatca taggaaactc agggacattt caagttgctg agagttttgt tatagttgtt    3120
ttctaaccca gccctccact gccaaaggcc aaaagctcag acagttggca gacgtccagt    3180
tagctcatct cactcactct gattctcctg tgccacagga aaagagggcc tggaaagcgc    3240
agtgcatgct gggtgcatga agggcagcct gggggacaga ctgttgtggg aacgtcccac    3300
tgtcctggcc tggagctagg ccttgctgtt cctcttctct gtgagcctag tggggctgct    3360
gcggttctct tgcagtttct ggtggcatct caggggaaca caaagctatg tctattcccc    3420
aatataggac ttttatgggc tcggcagtta gctgccatgt agaaggctcc taagcagtgg    3480
gcatggtgag gtttcatctg attgagaagg gggaatcctg tgtggaatgt tgaactttcg    3540
ccatggtctc catcgttctg ggcgtaaatt ccctgggatc aagtaggaaa atgggcagaa    3600
ctgcttaggg gaatgaaatt gccatttttc gggtgaaacg ccacacctcc agggtcttaa    3660
gagtcaggct ccggctgtag tagctctgat gaaataggct atccactcgg gatggcttac    3720 ttttaaaag ggtaggggga ggggctgggg aagatctgtc ctgcaccatc tgcctaattc    3780
cttcctcaca gtctgtagcc atctgatatc ctaggggaaa aggaaggcca ggggttcaca    3840
tagggcccca gcgagtttcc caggagttag agggatgcga ggctaacaag ttccaaaaac    3900
atctgccccg atgctctagt gtttggaggt gggcaggatg agaacagtg cctgtttggg    3960 ggaaaacagg aaatcttgtt aggcttgagt gaggtgtttg cttccttctt gcccagcgct    4020
gggttctctc cacccagtag gttttctgtt gtggtcccgt gggagaggcc agactggatt    4080
attcctcctt tgctgatcct gggtcacact tcaccagcca gggcttttga cggagacagc    4140
aaataggcct ctgcaaatca atcaaaggct gcaaccctat ggcctcttgg agacagatga    4200
tgactggcaa ggactagaga gcaggagtgc ctggccaggt cggtcctgac tctcctgact    4260
ctccatcgct ctgtccaagg agaacccgga gaggctctgg gctgattcag aggttactgc    4320
tttatattcg tccaaactgt gttagtctag gcttaggaca gcttcagaat ctgacacctt    4380
gccttgctct tgccaccagg acacctatgt caacaggcca aacagccatg catctataaa    4440
ggtcatcatc ttctgccacc tttactgggt tctaaatgct ctctgataat tcagagagca    4500
ttgggtctgg gaagaggtaa gaggaacact agaagctcag catgacttaa acaggttgta    4560
gcaaagacag tttatcatca gctctttcag tggtaaactg tggtttcccc aagctgcaca    4620
ggaggccaga aaccacaagt atgatgacta ggaagcctac tgtcatgaga gtggggagac    4680
aggcagcaaa gcttatgaag gaggtacaga atattctttg cgttgtaaga cagaatacgg    4740
gtttaatcta gtctaggcac cagattttt tcccgcttga taaggaaagc tagcagaaag    4800
tttatttaaa ccacttcttg agctttatct tttttgacaa tatactggag aaactttgaa    4860
gaacaagttc aaactgatac atatacacat atttttttga taatgtaaat acagtgacca    4920
tgttaaccta ccctgcactg ctttaagtga acatactttg aaaaagcatt atgttagctg    4980
agtgatggcc aagttttttc tctggacagg aatgtaaatg tcttactgga aatgacaagt    5040
ttttgcttga tttttttttt taaacaaaaa atgaaatata acaagacaaa cttatgataa    5100
agtatttgtc ttgtagatca ggtgttttgt tttgttttt taatttaaa atgcaaccct    5160 gcccctccc cagcaaagtc acagctccat ttcagtaaag gttggagtca atatgctctg    5220
gttggcaggc aaccctgtag tcatggagaa aggtatttca agatctagtc caatcttttt    5280
```

| | |
|---|---|
| ctagagaaaa agataatctg aagctcacaa agatgaagtg acttcctcaa aatcacatgg | 5340 |
| ttcaggacag aaacaagatt aaaacctgga tccacagact gtgcgcctca gaaggaataa | 5400 |
| tcggtaaatt aagaattgct actcgaaggt gccagaatga cacaaaggac agaattcctt | 5460 |
| tcccagttgt taccctagca aggctaggga gggcatgaac acaaacataa gaactggtct | 5520 |
| tctacacttt ctctgaatca tttaggttta agatgtaagt gaacaattct ttcttcctgc | 5580 |
| caagaaacaa agttttggat gagcttttat atatggaact tactccaaca ggactgaggg | 5640 |
| accaaggaaa catgatgggg gaggcagaga gggcaagagt aaaactgtag catagctttt | 5700 |
| gtcacggtca ctagctgatc cctcaggtct gctgcaaaca cagcatggag gacacagatg | 5760 |
| actctttggt gttggtcttt ttgtctgcag tgaatgttca acagtttgcc caggaactgg | 5820 |
| gggatcatat atgtcttagt ggacaggggt ctgaagtaca ctggaattta ctgagaaact | 5880 |
| tgtttgtaaa aactatagtt aataattatt gcattttctt acaaaaatat attttggaaa | 5940 |
| attgtatact gtcaattaaa gtgttttgt gtaaactggt tcaaaaaaaa aaaaaaaaa | 6000 |
| aaaaaaa | 6007 |

<210> SEQ ID NO 11
<211> LENGTH: 2660
<212> TYPE: DNA
<213> ORGANISM: Homo sapiens

<400> SEQUENCE: 11

| | |
|---|---|
| agtttctcct ttgttttacg tttgggagga ggtggcattg gaaatagcag agtgcttcgc | 60 |
| ggtaacaggg gttggagtgc aatggtgtga tctcagctca ctgcaacccc tgcctcccag | 120 |
| gctccagcga tcctcccacc tcagcctcct gaatagctga ccaccagcac actaggcaaa | 180 |
| cccacccac tcacggcctc ccttgggaat tcagacctaa ccatcgctga gctgaaacaa | 240 |
| atgtactgag gctggagcct gtgtgaacag aacagaagag gccttcactc tagtagtgct | 300 |
| cacagtccag caggtgtttg ctgaagacag cttactcaga tcactactgc ctggaggtgg | 360 |
| ttgatatatc ctggtgtaaa ccttcaagaa gggcacaggc aggaaaacat gagccagcaa | 420 |
| ctgaagaaac gggcaaagac aagacaccag aaaggcctgg gtggaagagc ccccagtggg | 480 |
| gctaagccca ggcaaggcaa gtcaagccaa gacctgcagg cggaaataga acctgtcagc | 540 |
| gcggtgtggg ccttatgtga tggctatgtg tgctatgagc ctggccctca ggctctcgga | 600 |
| ggggatgatt tctcagactg ttacatagaa tgcgtcataa ggggtgagtt ttctcaaccc | 660 |
| atcctggaag aggactcact ttttgagtcc ttggaatacc taagaaagg atcagaacaa | 720 |
| cagctttctc aaaaggtttt cgaagcaagc tcccttgaat gttctttgga atacatgaaa | 780 |
| aaaggggtaa agaagagct tccacaaaag atagttggag agaattcgct tgagtattct | 840 |
| gagtacatga caggcaagaa gcttccgcct ggaggaatac ctggcattga cctatcagat | 900 |
| cctaaacagc tcgcagaatt tgctagaaag aagccccca taaataaga atatgacagt | 960 |
| ctgagcgcaa tcgcttgtcc tcagagtgga tgcactagga agttgaggaa tagagctgcc | 1020 |
| ctgagaaagc atctcctcat tcatggtccc cgagaccacg tctgtgcgga atgtgggaaa | 1080 |
| gcgttcgttg agagctcaaa actaaagaga catttcctgg ttcatactgg agagaagccg | 1140 |
| tttcggtgca cttttgaagg gtgcggaaag cgcttctctc tggactttaa tttgcgtacg | 1200 |
| cacgtgcgca tccacacggg ggagaaacgt ttcgtgtgtc cctttcaagg ctgcaacagg | 1260 |
| aggtttattc agtcaaataa cctgaaagcc cacatcctaa cgcatgcaaa tacgaacaag | 1320 |
| aatgaacaag agggaaagta gtcctccaac aggatgaagc agattaacag aagagtgatc | 1380 |

-continued

```
agtgacaaac atgcctcatt gattattgtt tctaggaagg aatttctaaa tcaatattgc      1440
aaccccaaaa gcggttataa tttggtgtta ctaagatgct cctacacttt gtgataccgt      1500
tttaaggaca tggtgcattt ttttttcttt tatttgtttt atttagaact tttttttattt    1560 gtttattta gaactttgtg tgttcttaaa gtgtgcttcc aacaggaagg tcagtgataa      1620
attttcaaaa gcataacctt caatatatta tctgttggat tattggatat aagacttatt    1680
ttcatgtact ataaatatga aaataacttt gatttttaat tgtgtagttt ccatttctta    1740
gcttttgcct tttaaattta tacttcagcc aggcatagtg actgatgcct gtaatcccaa    1800
cactttgttg ggaggccaaa gcaggaggat agcttgaggc caggagttcc agaccagcct    1860
gggcaacata gtgagatcct gtctctacaa aaaaatttgt ttttatttgt atttatatat    1920
ttttattttt gttttgttg gtaggcgtct cgctctgtca cccaggctgg agtcagtgt      1980 cgtgatcttg gctcactgca acctccacct cccgggttca agtgattctc tggcctcagc    2040
ctcccaagta gctgggacta caggtgtgtg tcaccacgcc cggctaattt ttgtattttt    2100
agtagagatg gggtttcacc atgttggcca ggctagtctc aaactcctga cctccagtga    2160
tctgcccacc tcggcctccc aaagtgctgg gattacaggt gtgagccact gtgcctggcc    2220
ccccacaaca tgtttaaact tagctaggcc tggttgcata cgcctgtgtt cccagctact    2280
caggaggctg aagcaggagg atagcttgag cccaggagtt tgaggctaca gtgagctgtg    2340
attgcaccac tgtactccag actggataac agcaagagcc catcttttaa aaaaagtaaa    2400
aattaaaaat atacttcatg gttcatgtca tagccctaga gaatgaaaaa tttgcagtag    2460
atagtcaata aatgaatcag tagttaaata ttccttaaag tcaactgtat ttcattgtga    2520
tttttgtttt cttttatca ttgtatcaaa ctatatggaa atcatatggt tagatgtgat    2580
tatttgataa tgttagtcca tttgaatcca ttttagatat ttcacaatta aagaatatga    2640
aacttcagaa aaaaaaaaa                                                  2660
```

<210> SEQ ID NO 12
<211> LENGTH: 6063
<212> TYPE: DNA
<213> ORGANISM: Homo sapiens

<400> SEQUENCE: 12

```
aatccctccc tccggcgggc gtcgctggcg ggtggctagg cccaacggca ggaagccgac      60
gctatcctcc gttccgcggc gccgggtccg ccttccgtct gttctagggc ctgctcctgc    120
gcggcagctg ctttagaagg tctcgagcct cctgtaccct cccagggatg aaccgggcct    180
tccctctgga aggcgagggt tcgggccaca gtgagcgagg gccagggcgg tgggcgcgcg    240
cagagggaaa ccgatcagt tgagagagaa tcaagagtag cggatgaggc gcttgtgggg    300
cgcggcccgg aagccctcgg gcgcgggctg ggagaaggag tgggcggagg cgccgcagga    360
ggctcccggg gcctggtcgg gccggctggg cccggggcgc agtggaagaa agggacgggc    420
ggtgcccggt tgggcgtcct ggccagctca ccttgccctg gcggctcgcc ccgcccggca    480
cttgggagga gcaggcagg gcccgcggcc tttgcattct gggaccgccc ccttccattc    540 ccggggccagc ggcgagcggc agcgacggct ggagccgcag ctacagcatg agagccggtg    600
ccgctcctcc acgcctgcgg acgcgtggcg agcggaggca gcgctgcctg ttcgcgccat    660
gggggcaccg tggggctcgc cgacggcggc ggcgggcggg cggcgcgggt ggcgccgagg    720
ccgggggctg ccatggaccg tctgtgtgct ggcggccgcc ggcttgacgt gtacggcgct    780
```

```
gatcacctac gcttgctggg ggcagctgcc gccgctgccc tgggcgtcgc caaccccgtc    840
gcgaccggtg ggcgtgctgc tgtggtggga gccctctggg gggcgcgata gcgcccgag    900 gccgccccct gactgccggc tgcgcttcaa catcagcggc tgccgcctgc tcaccgaccg    960
cgcgtcctac ggagaggctc aggccgtgct tttccaccac cgcgacctcg tgaaggggcc   1020
ccccgactgg cccccgccct ggggcatcca ggcgcacact gccgaggagg tggatctgcg   1080
cgtgttggac tacgaggagg cagcggcggc ggcagaagcc ctggcgacct ccagccccag   1140
gcccccgggc cagcgctggg tttggatgaa cttcgagtcg ccctcgcact ccccggggct   1200
gcgaagcctg gcaagtaacc tcttcaactg gacgctctcc taccgggcgg actcggacgt   1260
ctttgtgcct tatggctacc tctacccccag aagccacccc ggcgacccgc cctcaggcct   1320
ggccccgcca ctgtccagga aacaggggct ggtggcatgg gtggtgagcc actgggacga   1380
gcgccaggcc cgggtccgct actaccacca actgagccaa catgtgaccg tggacgtgtt   1440
cggccggggc gggccgggc agccggtgcc cgaaattggg ctcctgcaca cagtggcccg   1500
ctacaagttc tacctggctt tcgagaactc gcagcacctg gattatatca ccgagaagct   1560
ctggcgcaac gcgttgctcg ctggggcggt gccggtggtg ctgggccag accgtgccaa   1620 ctacgagcgc tttgtgcccc gcggcgcctt catccacgtg gacgacttcc caagtgcctc   1680
ctccctggcc tcgtacctgc ttttcctcga ccgcaaccccc gcggtctatc gccgctactt   1740
ccactgcgcg cggagctacg ctgtccacat cacctccttc tgggacgagc cttggtgccg   1800
ggtgtgccag gctgtacaga gggctgggga ccggcccaag agcatacgga acttggccag   1860
ctggttcgag cggtgaagcc gcgctcccct ggaagcgacc caggggaggc caagttgtca   1920 gcttttgat cctctactgt gcatctcctt gactgccgca tcatgggagt aagttcttca   1980
aacacccatt tttgctctat gggaaaaaaa cgatttacca attaatatta ctcagcacag   2040
agatgggggc ccggtttcca tattttttgc acagctagca attgggctcc ctttgctgct   2100
gatgggcatc attgtttagg ggtgaaggag ggggttcttc ctcaccttgt aaccagtgca   2160
gaaatgaaat agcttagcgg caagaagccg ttgaggcggt ttcctgaatt tccccatctg   2220
ccacaggcca tatttgtggc ccgtgcagct tccaaatctc atacacaact gttcccgatt   2280 cacgttttc tggaccaagg tgaagcaaat ttgtggttgt agaaggagcc ttgttggtgg   2340
agagtggaag gactgtggct gcaggtggga ctttgttgtt tggattcctc acagccttgg   2400
ctcctgagaa aggtgaggag ggcagtccaa gaggggccgc tgacttcttt cacaagtact   2460
atctgttccc ctgtcctgtg aatggaagca aagtgctgga ttgtccttgg aggaaactta   2520
agatgaatac atgcgtgtac ctcactttac ataagaaatg tattcctgaa aagctgcatt   2580
taaatcaagt cccaaattca ttgacttagg ggagttcagt atttaatgaa acccctatgga   2640 gaatttatcc ctttacaatg tgaatagtca tctcctaatt tgtttcttct gtctttatgt   2700
ttttctataa cctggatttt ttaaatcata ttaaaattac agatgtgaaa ataaagcaga   2760
agcaaccttt ttccctcttc ccagaaaacc agtctgtgtt tacagacaga agagaaggaa   2820
gccatagtgt cacttccaca caattattta tttcatgtct ttactggacc tgaaatttaa   2880
actgcaatgc cagtcctgca ggagtgctgg cattaccctc tgcagaacag tgaaaggtat   2940
tgcactacat tatggaatca tgcaaaagga aaaaagtttt catgatatct gttgttggca   3000 gttttttgttt atctctgaca gttttttagtt aaatgtttag atcctcagaa ctacattagt   3060
gcctactatt aacttactct gtctcttgtt aaaggctaaa tctgcgcttc ccctggtgc   3120 cagcaggttc ccctcacagt caatgcagtg gtatagcata tcctcacatt tctagtgccc   3180
```

```
ttgagactgt gctatggaac caatcttgaa catacatgca ttgacttgac aagttactga    3240
gtaagcagca tattcagcag gtgccactac atgcctactc tgccagacac tgagcttggg    3300
gccctaggga agatagagaa ttatacaagg caaagtcctt ctctttaggg ctcttacaat    3360
ctatcacttc caaaaagtaa atggtgactg ataaaacaat tggcagaacc tgtttgatta    3420
ctgtgacagt cttaatgata ccataaatca atattagaaa gctagttgac ttaaagcctg    3480
aaataatggg agttttctcc tccacttatt agaataagga ccctcagtga ctaattattg    3540
tgggtagggt caagattaac tagttttata cagagttctg ctgtaaatag tcattttgca    3600
tttgattagt gcagttctct gaatcataaa gcaagtttta cctctctgta catgttttttg   3660 cagacatact tgaaaagctc acttaaatct aggtgcttca attcactttc ttgagaggac    3720
aaatgaaaag ctgtggagaa aatgtcctca ttaaagtatt aaagtgtggg cagaattaca    3780
attacaaagt gccagccacc gaataaagat aaaagttcag ttcttaaaat gagttttttat   3840 gagataacag tcagtgatct tggtgttacc gggattccac atggggcagt gggaaagagt    3900
tcaggttttg aaggtaacct agtttagatt tgaattccag ctatgtgaca ttgggtaaat    3960
tagtagtagt cctgagcctc agcgtcctca tctataaaat gactggcgaa aatacttcac    4020
aagctcattt tgagcacttt aggaagtaag tgaaagtacc taaaatagca ggcacccaat    4080
tgatgatttt atatcttcct tctttgcttg cagtgatttc aggatgtcct catatctatt    4140
tataggtcta aaattatatc ttaaggtatg ttgtagaata aattaaaagg ataatctaaa    4200
tcaccattta gattaagctt gacttgcaaa ctaggaagaa gcacctaggc tttcttttgaa   4260 aatatttttt tggttcgttt tggtaaagct ctataaattg gtatctatta ttttaccaat    4320 tttttttttag tattaagtcc atttagaact aaccatatta tttatggaat aattagcatg   4380
aggaaggtat aattgcattt tttttttttt gagacggagt cttgcactgt agccccagct    4440
ggactgcagt ggcgtgatct tggctcactg caacctccgc ctcccaggtt caagcgattc    4500
tcctgcctca gcctcccgag cagctgagac tacaggcgcc tgccaccacg cctggccaat    4560 ttttttgtatt tttagtagag actgcgtttc accatgttgg gcaggctggt cttgaactcc    4620
tgaccttgtg atccacctgc ctcggcctct cagagagctg ggattacagg tgtgagccgc    4680
cgtgcccagc cattgcattt ttattcacat acacattgtt aatgtggaac aatttaacac    4740
taatctcatc agagagcgag atgaatgtgg caattgctca ttttattttg catatattaa    4800
attgagtagg ttcagctcta acataccttta agaaaaatgc atatcggtgc actgtatgta    4860
tttcaaaatg cctttcctat gattgtcatg tcctcctttta aggcttttcc ctcaaattta    4920
ttacaaattt agtattttta gtacttgatg actctaatta catgaatgca cctggaatga    4980
catttgtaac agaagacggt ctgacttgct ttcagtattc acaagttctt tccagttttcc   5040 aagtcttttc ctagcagtaa tttaggggag acagaggagt ttcatgtaaa gagcatgcag    5100
tttggagtca gaacctgggt atgactctgt ggccttgatg aagcaagtta cttaaactct    5160
tgagttttag cttttctcctt tacaatgcat gaatgcctat cccccctacaa acaaagatt    5220 aaatgtgatg atgtatgcca aggtgctttg tatattgtaa agtgctatat aattataaga    5280
tgttctaaat tttcaaggat ctaaaccagg gattggcaaa cgttttttcca gggagtaaat    5340 attttacgct ttgcatatat aatttatgga ggtgttgaga ggatagatta gacacttgaa    5400
gtactcagga tagtgcctgg catgtaggaa gcacctggaa aatattcgct gtgattacca    5460
tcagtccatt ttaccgagga aggagccaag gtccaggccc actgaaggac ttgcataaca    5520
```

```
ttacaatagc agtggcagaa ccagccatgc ttctgcaaat cacaacctct ttgagcctct    5580
gtcacctgaa ctgcaaaatg agtgggttag acaaaatcat ctgttgggac ctcctagttc    5640
cacgtgctat cattctacta actggcaccc taaggttgaa agtgcttatc tgcttttccaa   5700 tgtggcttcc ttacagtctg gaactgacaa tatgcaggag cagtaaactg cagaaaacc    5760 aggaatcaga gaaagaaaat ataatttaac tttaaagatg taaattatat atatagtata    5820
ttatatatat ttttaaagct ttatatgcct caaatatcag ggaaaggagc caagtccttg    5880
gtatttagtt tggtgaatac ttgcattgaa tacatgtcaa gatgtcaagt cattttgaa    5940 tgtgtctcag ggatttctat gctacacatt cttttaacaa atcaagtatt tatgtacaca    6000
tgttcagatt ttttgacaaa atgattaaaa taatgagatg gaaaatgaaa aaaaaaaaa    6060 aaa                                                                 6063

<210> SEQ ID NO 13
<211> LENGTH: 1393
<212> TYPE: DNA
<213> ORGANISM: Homo sapiens

<400> SEQUENCE: 13 agcccttttgt ttatggcctg atctagctaa ggcttctaga cttcaggagc ttaagaatcg     60
tccggagggc tgggcgtggc ggtgcaggcc tgtagtccca cccactccga aggctgcgga    120
gggaggatca acttgagtct gggaactcag ccaggaattc aagaccagcc tgggcaacac    180
agtgaggccc cctacccaca tcctctccgt ccccgcaatc tccttccatc ccagggtgtt    240
gctgaaaatg tcagatgcaa atttggatag cagcaagaag aatttcttgg aggggggaagt   300 agatgatgag gaaagtgtga ttttgacact ggtgccagtt aaagatgacg caaatatgga    360
acaaatggaa ccaagcgttt cttcaacttc tgatgtcaaa ctggagaagc taagaaata    420 caatccaggt catctacttc aaacaaatga gcaatttaca gctccacaaa agctagatg    480 caaaatacca gcccttccct tgccgaccat tttgcctccc attaataagg tgtgtcggga    540
cactttgcgg gactggtgtc aacaactcgg tttgagtact aatggcaaga aaatcgaagt    600
ttatctgagg cttcataggc atgcttaccc tgaacaacgg caagatatgc ctgaaatgtc    660
acaagagacc agattacagc gatgttcgag gaaacgcaag gcagtgacca agagagcaag    720
gcttcagaga agttatgaga tgaatgagag agcagaagag accaatacag ttgaagtgat    780
aacttcagca ccgggagcca tgttggcatc atgggcaaga attgctgcaa gagctgttca    840
gcctaaggct ttgaattcat gttccattcc tgtttctgtt gaggcctttt tgatgcaagc    900
ctctggcgtc aggtggtgtg tggtccatgg cagacttctc tcggcagaca caaagggttg    960
ggtacgcctg cagtttcatg caggtcaggc ctgggtgcct accactcaca ggaggatgat   1020
ttctctcttc ttgttacctg cctgcatttt cccatcccca ggcatagaag ataatatgtt   1080
atgccccgac tgtgctaaga ggaataagaa gatgatgaaa agattaatga cagtagagaa   1140
gtagcagcaa cctgtttgaa tacaatgtac taaaggaggg atgtactttc agatcatgta   1200
acctattacg aaggagtgga agaggagaca atttgaatga atcctcatga tctacaaaac   1260
aaaatcatag tgactaggac tccacagtga agatggttga ctagtgacac agccccatct   1320
aaagaatccc tttctgtatg tctgaaaacc cattaaaata aagtcactgc aattggcctt   1380
gtaaaaaaaa aaa                                                      1393

<210> SEQ ID NO 14
<211> LENGTH: 1079
```

<212> TYPE: DNA
<213> ORGANISM: Homo sapiens

<400> SEQUENCE: 14

```
tggagctccg gttttcagcc tctttccggg ctacctggta gcaatttgag gctctgtcat      60
cagtttctgc tacgtttcaa agatcctgga gaagcctagt gttgtgtcaa gacgccgatg     120
gacccatcac agtttaatcc aacctacatc ccagggtctc cacaaatgct caccgaagaa     180
aattcccggg acgattcagg ggcctctcaa atctcctccg agacgttgat aaagaacctt     240
agtaacttga ctatcaacgc tagtagcgaa tctgtttccc ctctatcgga agctttactc     300
cgtcgagagt ctgtaggagc agcagtcctc agggaaatcg aagatgagtg gctttacagc     360
aggagaggag taagaacatt gctgtctgtg cagagagaaa agatggcaag attgagatac     420
atgttactcg gcggagttcg tacgcatgaa agaagaccaa caaacaagga gcctaaggga     480
gttaagaagg aatcaagacc attcaaatgt ccctgcagtt tctgcgtgtc taatggatgg     540
gatccttctg agaatgctag aatagggaat caagacacca agccacttca gccataaatc     600
ttattcttgc accttttttt cttggtagta attttatata gcaggttgag aaagctactc     660
tatgctagta tagactatac accaataatt ttgataatga gttctaggat gtatttttct     720
tgtatctttt tcttcctact atgatactag taattcataa gggatctgtg taatctgaat     780
gtatttgaat aactttagct ctactgtttg atttgaccca aagaagccaa gatgatataa     840
gtattcccat gtgtcttaga agcccaaagt cagtgagatg aaacccaaca tcaagaaatt     900
gaagcaaagt tacttatgga taaagaaagc attaggtagt tgggctatag cataattaga     960
ttttctggct ttcaaaaatt tggattgcaa tcacagcaaa ctttgttatt tttacagttt    1020
tcagtacaaa agtgtttata tagaaacaat aaagttgaca tttgagtacc ttttaaaaa    1079
```

<210> SEQ ID NO 15
<211> LENGTH: 24
<212> TYPE: DNA
<213> ORGANISM: Homo sapiens

<400> SEQUENCE: 15

```
cgcatggggt tcggcttcct gtcc                                             24
```

<210> SEQ ID NO 16
<211> LENGTH: 17
<212> TYPE: DNA
<213> ORGANISM: Homo sapiens

<400> SEQUENCE: 16

```
cacggtgcgg gcatctg                                                     17
```

<210> SEQ ID NO 17
<211> LENGTH: 21
<212> TYPE: DNA
<213> ORGANISM: Homo sapiens

<400> SEQUENCE: 17

```
ccttccatgt gcagcttact c                                                21
```

PLURIPOTENT STEM CELL ASSAY

CROSS-REFERENCE TO RELATED APPLICATIONS

This application is the U.S. national phase application, pursuant to 35 U.S.C. § 371, of PCT International Application Ser. No.: PCT/AU2017/051254, filed Nov. 15, 2017, designating the United States and published in English, which claims the benefit of Australian Patent Application No. 2016904679, filed Nov. 16, 2016. The entire contents of the aforementioned patent applications are incorporated herein by this reference.

SEQUENCE LISTING

The instant application contains a Sequence Listing which has been submitted electronically in ASCII format and is hereby incorporated by reference in its entirety. Said ASCII copy, created on Sep. 6, 2019, is named 182356_010200_SL.txt and is 107,280 bytes in size.

FIELD

The invention relates to a method for detecting residual, undifferentiated pluripotent stem cells (PSCs) in a culture of cells differentiated from PSCs.

BACKGROUND

Pluripotent stem cells (PSCs), in particular human PSCs, which include Embryonic Stem Cells (ESCs) and induced Pluripotent Stem Cells (iPSCs), provide the opportunity to develop novel cell-based therapeutic products.

Differentiated derivatives of iPSCs have therapeutic efficacy in a variety of disease applications (e.g. cirrhosis, Parkinson's disease, age-related macular degeneration, cardiac ischemia, diabetes, graft-versus host disease).

However, use in clinical trials of therapeutic compositions comprising PSC-derived cells poses several challenges, in particular the presence of residual undifferentiated PSCs in the final product that have a known potential for tumour formation. Such a challenge is especially pertinent to therapies that require high doses of differentiated, PSC-derived cells.

Accordingly, there is a need for a method, or an improved method, for detecting residual, undifferentiated PSCs in a culture of cells derived from PSCs, to be used in quality control when producing therapeutic compositions comprising PSC-derived cells.

Any publications mentioned in this specification are herein incorporated by reference. However, if any publication is referred to herein, such reference does not constitute an admission that the publication forms a part of the common general knowledge in the art in Australia or any other country.

SUMMARY

The inventors have addressed this need for quality control in manufacture of therapeutic compositions comprising PSC-derived cells by developing a method for detecting residual, undifferentiated PSCs in a culture of PSC-derived cells. The method relies on a cell culture protocol for expansion of singularised, undifferentiated PSCs to increase sensitivity (true positive) and specificity (true negative) for residual undifferentiated PSCs.

Accordingly, a first aspect provides a method for detecting residual, undifferentiated pluripotent stem cells (PSCs) in a culture of cells differentiated from PSCs, the method comprising:

culturing the cells on a substrate coated with laminin-521 and E-cadherin in a medium comprising a Rho-associated, coiled-coil containing protein kinase (ROCK) inhibitor;

quantitating in the cultured cells expression of a marker of residual, undifferentiated PSCs; and comparing the marker expression in the cultured cells with the marker expression in a reference culture of cells comprising a known proportion of PSCs, wherein lower marker expression in the culture of cells than marker expression in the reference culture of cells indicates absence of residual, undifferentiated PSCs in the cultured cells or presence of residual, undifferentiated PSCs in the cultured cells at a proportion lower than the known proportion of PSCs in the reference culture of cells.

The inventors propose that this method provides an improved means for quality control and is an important contribution to the safety, and therefore advancement, of therapies relying on PSC-derived cells.

Accordingly, in one embodiment, the method further comprises formulating the culture of cells in which residual, undifferentiated PSCs are absent or lower than a known proportion into a therapeutic composition. The method may further comprise treating or preventing a condition in a subject by administering the therapeutic composition to the subject.

A second aspect provides a method for manufacturing a therapeutic composition, the method comprising formulating into a composition for therapeutic administration to a subject a culture of cells in which residual, undifferentiated PSCs are absent or lower than a known proportion when detected by the method of the first aspect.

A third aspect provides a method for treating or preventing a condition in a subject, the method comprising administering to the subject:

a culture of cells in which residual, undifferentiated PSCs are absent or lower than a known proportion when detected by the method of the first aspect; or a therapeutic composition when manufactured by the method of the second aspect.

An alternative form of the third aspect provides use of a culture of cells in which residual, undifferentiated PSCs are absent or lower than a known proportion in the manufacture of a medicament, such as a therapeutic composition, for treating or preventing a condition in a subject, wherein residual, undifferentiated PSCs in the culture of cells differentiated from PSCs are detected by the method of the first aspect.

Another alternative form of the third aspect provides:

a culture of cells in which residual, undifferentiated PSCs are absent or lower than a known proportion when detected by the method of the first aspect; or a therapeutic composition when manufactured by the method of the second aspect, for use in treating or preventing a condition in a subject.

The condition to be prevented or treated may be bone cysts, bone neoplasms, fractures, cartilage defects, osteoarthritis, ligament injury, osteogenesis imperfecta, osteonecrosis, osteoporosis, aplastic anaemia, graft versus host disease (GvHD), myelodysplastic syndrome, Type 1 diabetes, Type 2 diabetes, autoimmune hepatitis, liver cirrhosis, liver failure, dilated cardiomyopathy, heart failure, myocardial infarction, myocardial ischemia, Crohn's disease, ulcerative colitis, burns, epidermolysis bullosa, lupus erythematosus, rheumatoid arthritis, Sjogren's disease, systemic sclerosis, bronchopulmonary dysplasia, chronic obstructive airways disease, emphysema, pulmonary fibrosis, amyotrophic lateral sclerosis (ALS), Alzheimer's disease, brain injury, ataxia, degenerative disc disease, multiple system atrophy, multiple sclerosis, Parkinson's disease, retinitis pigmentosa, Romberg's disease, spinal cord injury, stroke, muscular dystrophy, limb ischaemia, kidney injury, lupus nephritis, endometriosis and complications of bone marrow or solid organ transplantation.

A fourth aspect provides a kit for detecting residual, undifferentiated PSCs in a culture of cells differentiated from PSCs, the kit comprising:
 laminin-521; and
 E-cadherin; and
 a ROCK inhibitor.

In one embodiment, the kit is used according to the method of the first aspect.

BRIEF DESCRIPTION OF THE FIGURES

FIG. 1 is an example amino acid sequence of human laminin-521 α chain (SEQ ID NO: 1).

FIG. 2 is an example amino acid sequence of human laminin-521 β chain (SEQ ID NO: 2).

FIG. 3 is an example amino acid sequence of human laminin-521 γ chain (SEQ ID NO: 3).

FIG. 4 is an example amino acid sequence of human E-cadherin (SEQ ID NO: 4).

FIG. 5 is an example coding nucleotide sequence of human LIN28 (LIN28A) (SEQ ID NO: 5).

FIG. 6 is an example coding nucleotide sequence of human OCT4 (POU5F1) (SEQ ID NO: 6).

FIG. 7 is an example coding nucleotide sequence of human SOX2 (SEQ ID NO: 7).

FIG. 8 is an example coding nucleotide sequence of human FOXD3 (SEQ ID NO: 8).

FIG. 9 is an example coding nucleotide sequence of human NANOG (SEQ ID NO: 9).

FIG. 10 is an example coding nucleotide sequence of human PODXL (SEQ ID NO: 10).

FIG. 11 is an example coding nucleotide sequence of human REX1 (ZFP42) (SEQ ID NO: 11).

FIG. 12 is an example coding nucleotide sequence of human SSEA1 (FUT4) (SEQ ID NO: 12).

FIG. 13 is an example coding nucleotide sequence of human DPPA2 (SEQ ID NO: 13).

FIG. 14 is an example coding nucleotide sequence of human DPPA3 (SEQ ID NO: 14).

DETAILED DESCRIPTION

Disclosed herein is a method for detecting residual, undifferentiated PSCs in a culture of cells derived from PSCs, where the PSC-derived cells are destined for therapeutic administration to a subject. Accordingly, the invention provides an improved method of quality control and risk minimisation, for example, risk of tumour formation from such residual, undifferentiated PSCs.

The method relies on specific culture conditions to expand the undifferentiated PSCs under conditions that support PSC clonal growth, then quantitation of expression of a gene that is highly expressed in PSCs, but is not expressed, or only minimally expressed, in PSC-derived cells that have undergone differentiation. The culture conditions may selectively support expansion of PSCs at the single cell level. In one embodiment, the PSCs may be cultured under conditions that support PSC growth from a single cell suspension. Such culture conditions are known in the art and include laminin-521 and E-cadherin as described herein, as well as commercially available systems that include the Cellartis iPSC Single-Cell Cloning DEF-CS Culture Media Kit, Gibco™ StemFlex™ Medium, and PluriQ™ G9™ Cloning Medium in conjunction with single cell growth on vitronectin.

Marker expression in a test culture at or below marker expression in a reference culture with a known proportion of undifferentiated PSCs indicates that the test culture comprises a lower proportion of undifferentiated PSCs than the reference culture.

Importantly, the method can detect residual, undifferentiated PSCs in a culture of PSC-derived cells at low proportions of the total cell number, for example 0.001% or 10 ppm.

Unless defined otherwise in this specification, technical and scientific terms used herein have the same meaning as commonly understood by the person skilled in the art to which this invention belongs and by reference to published texts.

It is to be noted that the term "a" or "an" refers to one or more, for example, "a molecule," is understood to represent one or more molecules. As such, the terms "a" or "an", "one or more," and "at least one" may be used interchangeably herein.

In the claims which follow and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The term "about" as used herein contemplates a range of values for a given number of ±25% the magnitude of that number. In other embodiments, the term "about" contemplates a range of values for a given number of ±20%, ±15%, ±10%, or ±5% the magnitude of that number. For example, in one embodiment, "about 3 grams" indicates a value of 2.7 to 3.3 grams (i.e. 3 grams ±10%), and the like.

Similarly, in other embodiments, periods of time may vary by ±25%, ±20%, ±15%, ±10%, or ±5% of that period of time. For example, "one day" may include a period of about 18 to about 30 hours. Periods of time indicated that are multiple day periods may be multiples of "one day," such as, for example, two days may span a period of about 36 to about 60 hours, and the like. In other embodiments, time variation may be lessened, for example, where: day 1 is 24±3 hours from day 0; day 2 is 48±3 hours from day 0; day 3 is 72±3 hours from day 0; day 4 is 96±3 hours from day 0; day 5 is 120 hours±3 hours from day 0, and so on. In some embodiments, about 3 days is 3 days ±1 day, and about 5 days is 5 days ±1 day.

As used herein, "pluripotent stem cell" or "PSC" refers to a cell that has the ability to reproduce itself indefinitely, and to differentiate into any other cell type. There are two main types of pluripotent stem cell: embryonic stem cells (ESCs) and induced pluripotent stem cells (iPSCs).

As used herein, "embryonic stem cell" or "ESC" refers to a cell isolated from a five to seven day-old embryo donated with consent by patients who have completed in vitro fertilisation therapy, and have surplus embryos. The use of ESCs has been hindered to some extent by ethical concerns about the extraction of cells from human embryos.

Human PSCs suitable for manufacturing a therapeutic composition include H1 and H9 human ESCs.

As used herein, "induced pluripotent stem cell" or "iPSC" refers to an ESC-like cell derived from adult cells. iPSCs have very similar characteristics to ESCs, but avoid the ethical concerns associated with ESCs, since iPSCs are not derived from embryos. Instead, iPSCs are typically derived from fully differentiated adult cells that have been "reprogrammed" back into a pluripotent state.

Human iPSCs suitable for manufacturing a therapeutic composition include, but are not limited to, iPSC 19-9-7T, MIRJT6i-mND1-4 and MIRJT7i-mND2-0 derived from fibroblasts and iPSC BM119-9 derived from bone marrow mononuclear cells. Other suitable iPSCs may be obtained from Cellular Dynamics International (CDI; Nasdaq: ICEL) of Madison, Wis., USA.

As used herein, "differentiating" refers to a process of a cell changing from one cell type to another, in particular a less specialised type of cell becoming a more specialised type of cell.

As used herein, the term "derived from" may encompass "differentiating" a PSC into another cell type.

Accordingly, an "undifferentiated PSC" is a PSC that has not differentiated into another cell type. With respect to the present disclosure, the undifferentiated PSC is present within a population of otherwise differentiated PSCs.

As used herein, "medium" or its plural "media" refers to a liquid or gel designed to support the growth, including expansion and differentiation, of cells. Such growth, including expansion and differentiation, of cells in vitro is referred to as "culturing" cells, or cell "culture".

However, cells cannot be held in culture indefinitely owing to the increasing concentration of toxic metabolites, decreasing concentration of nutrients, and, for dividing cells, an increasing number of cells. As used herein, "passaging" refers to the process of producing a new cell culture with refreshed concentrations of nutrients, no toxic metabolites, and optionally a lower density of cells than the originating culture.

The number of passages for a cell culture, e.g. a PSC-derived cell culture to be tested by the present method, may be 1, 2, 3, 4, 5, 6, 7, 8, 9, 10, 11, 12, 13, 14, 15, 16, 17, 18, 19, 20, 21, 22, 23, 24, or 25. Preferably, the number of passages is 10 or fewer. More preferably, the number of passages is 5 or 6. In one embodiment, the PSC-derived cells have undergone 5 passages before being subjected to the present method.

In one embodiment, the PSC-derived cell is a mesenchymal stem (or stromal) cell (MSC).

In one embodiment, the ESC-derived cell is a MSC.

In a preferred embodiment, the iPSC-derived cell is a MSC, which may also be referred to as an iPSC-MSC.

As used herein, "mesenchymal stem cell" or "MSC" refers to a particular type of stem cell that may be isolated from a wide range of tissues, including bone marrow, adipose tissue (fat), placenta and umbilical cord blood. MSCs may differentiate into bone cells (osteocytes), cartilage cells (chondrocytes), fat cells (adipocytes), and other kinds of connective tissue cells such as those in tendons According to the present disclosure, MSCs may be formed from PSCs via $^{EMH}$lin$^-$KDR$^+$APLNR$^+$PDGFRalpha$^+$ primitive mesoderm cells with mesenchymoangioblast (MCA) potential. "$^{EMH}$lin$^-$KDR$^+$APLNR$^+$PDGFRalpha$^+$ primitive mesoderm cell with mesenchymoangioblast (MCA) potential" refers to a cell expressing typical primitive streak and lateral plate/extra-embryonic mesoderm genes. These cells have potential to form mesenchymoangioblast (MCA) and hemangioblast colonies in serum-free medium in response to FGF2. The term $^{EMH}$lin$^-$ denotes lack of expression of CD31, VE-cadherin endothelial markers, CD73 and Cd105 mesenchymal/endothelial markers, and CD43 and CD45 hematopoietic lineage markers.

As used herein, "mesenchyme" or "mesenchymal" refers to embryonic connective tissue that is derived from the mesoderm and that differentiates into hematopoietic tissue (lymphatic and circulatory systems) and connective tissue, such as bone and cartilage. However, MSCs do not differentiate into hematopoietic cells.

MSCs secrete bioactive molecules such as cytokines, chemokines and growth factors and have the ability to modulate the immune system. MSCs have been shown to facilitate regeneration and effects on the immune system without relying upon engraftment. In other words, the MSCs themselves may not necessarily become incorporated into the host—rather, they may exert their effects and are then eliminated within a short period of time. However, MSCs may be engrafted into damaged tissues following administration and migration.

MSCs are currently in clinical trials for treating numerous conditions, diseases and disorders, including graft-versus host disease.

The ability of MSCs to exert immunomodulatory/immunosuppressive effects, in particular by suppressing T cells, is believed to be central to the therapeutic effects of MSCs in a wide range of conditions, diseases and disorders, including graft-versus host disease, immune disorders including autoimmune disorders, cardiovascular disorders, orthopaedic disorders and rejection of transplanted solid organs. Some specific examples include bone cysts, bone neoplasms, fractures, cartilage defects, osteoarthritis, ligament injury, osteogenesis imperfecta, osteonecrosis, osteoporosis, aplastic anaemia, myelodysplastic syndrome, Type 1 diabetes, Type 2 diabetes, autoimmune hepatitis, liver cirrhosis, liver failure, dilated cardiomyopathy, heart failure, myocardial infarction, myocardial ischemia, Crohn's disease, ulcerative colitis, burns, epidermolysis bullosa, lupus erythematosus, rheumatoid arthritis, Sjogren's disease, systemic sclerosis, bronchopulmonary dysplasia, chronic obstructive airways disease, emphysema, pulmonary fibrosis, ALS, Alzheimer's disease, brain injury, ataxia, degenerative disc disease, multiple system atrophy, multiple sclerosis, Parkinson's disease, retinitis pigmentosa, Romberg's disease, spinal cord injury, stroke, muscular dystrophy, limb ischaemia, kidney injury, lupus nephritis, endometriosis and complications of bone marrow or solid organ transplantation, MSCs are thought to perform a critical role in injury healing, and have been shown to be effective in treating tissue injury and degenerative diseases, including in the digestive system, for example in liver cirrhosis and liver failure, in the musculoskeletal system, in periodontal tissue, in diabetic critical limb ischemia, in osteonecrosis, in burn-related disorders, in myocardial infarction, in cornea damage, in the brain, in the spinal cord, in the lungs, and in treating radiation exposure.

MSCs have shown therapeutic outcomes in immune disorders, including graft-versus-host disease, systemic lupus erythematosus (SLE), Crohn's disease, multiple system atrophy, multiple sclerosis, amyotrophic lateral sclerosis, and stroke.

MSCs have been shown to exert immunosuppressive activities against T cells, B cells, dendritic cells, macrophages, and natural killer cells. While not wishing to be bound by theory, the underlying mechanisms may comprise immunosuppressive mediators, for example nitric oxide, indoleamine 2,3, dioxygenase, prostaglandin E2, tumour necrosis factor-inducible gene 6 protein, CCL-2, and programmed death ligand 1. These mediators are expressed at a low level until stimulated, for example by an inflammatory cytokines, such as IFNγ, TNFα, and IL-17.

iPSC-derived MSCs (iPSC-MSCs) have a unique advantage over directly sourced MSCs, i.e. derived from tissues such as bone marrow, umbilical cord blood, adipose tissue, because in vitro expansion of iPSCs can provide a virtually unlimited supply of MSCs.

iPSC-MSCs can be produced according to example 1.

PSCs are able to differentiate into any cell type of any of endoderm, ectoderm, and mesoderm. PSCs undergo differentiation into multipotent progenitor cells that differentiate further into functional cells. Therefore, the description above of MSCs is exemplary and not to be construed as limiting, and other examples of PSC-derived cells may include: hematopoietic stem cells that give rise to all the types of blood cells including red blood cells, B lymphocytes, T lymphocytes, natural killer cells, neutrophils, basophils, eosinophils, monocytes, macrophages, and platelets; neural stem cells in the brain that give rise to its three major cell types being nerve cells (neurons) and two categories of non-neuronal cells, astrocytes and oligodendrocytes; epithelial stem cells in the lining of the digestive tract that give rise to absorptive cells, goblet cells, Paneth cells, and enteroendocrine cells; and skin stem cells that occur in the basal layer of the epidermis give rise to keratinocytes and that occur at the base of hair follicles and give rise to both the hair follicle and to the epidermis.

As used herein, a "substrate" is any material suitable for culturing PSCs and/or cells derived from PSCs. Examples include plastic culture ware such as dishes, multi-well plates, and flasks.

All proteins described herein are known to the person skilled in the art and are available commercially.

Laminin-521 is a heterotrimeric protein secreted by human PSCs. Laminin-521 comprises five α chains, two β chains and one γ chain (i.e. α5β2γ1). In one embodiment, the α chain, the β chain and the γ chain have the amino acid sequences represented by SEQ ID NOs: 1, 2 and 3 (FIGS. 1, 2 and 3), respectively.

E-cadherin is a calcium-dependent cell adhesion protein associated with epithelial cell function. In one embodiment, human E-cadherin has the amino acid sequence represented by SEQ ID NO: 4 (FIG. 4).

In performing the present method, the substrate may be coated with laminin-521 using about 0.1 μg/mL, 0.2 μg/mL, 0.3 μg/mL, 0.4 μg/mL, 0.5 μg/mL, 0.6 μg/mL, 0.7 μg/mL, 0.8 μg/mL, 0.9 μg/mL, 1 μg/mL, 2 μg/mL, 3 μg/mL, 4 μg/mL, 5 μg/mL, 6 μg/mL, 7 μg/mL, 8 μg/mL, 9 μg/mL, or 10 μg/mL and/or about 0.1 μg/cm$^2$, 0.2 μg/cm$^2$, 0.3 μg/cm$^2$, 0.4 μg/cm$^2$, 0.5 μg/cm$^2$, 0.6 μg/cm$^2$, 0.7 μg/cm$^2$, 0.8 μg/cm$^2$, 0.9 μg/cm$^2$, 1 μg/cm$^2$, 2 μg/cm$^2$, 3 μg/cm$^2$, 4 μg/cm$^2$, 5 μg/cm$^2$, 6 μg/cm$^2$, 7 μg/cm$^2$, 8 μg/cm$^2$, 9 μg/cm$^2$, or 10 μg/cm$^2$.

The substrate may be coated with E-cadherin using about 0.1 μg/mL, 0.2 μg/mL, 0.3 μg/mL, 0.4 μg/mL, 0.5 μg/mL, 0.6 μg/mL, 0.7 μg/mL, 0.8 μg/mL, 0.9 μg/mL, 1 μg/mL, 2 μg/mL, 3 μg/mL, 4 μg/mL, 5 μg/mL, 6 μg/mL, 7 μg/mL, 8 μg/mL, 9 μg/mL, or 10 μg/mL and/or about 0.01 μg/cm$^2$, 0.05 μg/cm$^2$, 0.1 μg/cm$^2$, 0.2 μg/cm$^2$, 0.25 μg/cm$^2$, 0.3 μg/cm$^2$, 0.4 μg/cm$^2$, 0.5 μg/cm$^2$, 0.6 μg/cm$^2$, 0.7 μg/cm$^2$, 0.8 μg/cm$^2$, 0.9 μg/cm$^2$, 1 μg/cm$^2$, 2 μg/cm$^2$, 3 μg/cm$^2$, 4 μg/cm$^2$, 5 μg/cm$^2$, 6 μg/cm$^2$, 7 μg/cm$^2$, 8 μg/cm$^2$, 9 μg/cm$^2$, or 10 μg/cm$^2$.

In a preferred embodiment, the substrate is coated with laminin-521 using 10 μg/mL and 2 μg/cm$^2$ and with E-cadherin using 1.1 μg/mL and 0.22 μg/cm$^2$.

Rho-associated, coiled-coil containing protein kinase (ROCK) is involved mainly in regulating the shape and movement of cells by acting on the cytoskeleton. Thus, a "ROCK inhibitor" inhibits this function, and for present purposes a "ROCK inhibitor" enhances survival of iPSCs.

In one embodiment the ROCK inhibitor is Y27632 (CAS No: 129830-38-2). Other examples of ROCK inhibitors that may be used in the present method are AS 1892802 (CAS No: 928320-12-1), Fasudil hydrochloride (CAS No: 105628-07-7), GSK 269962 (CAS No: 850664-21-0), GSK 429286 (CAS No: 864082-47-3), H 1152 dihydrochloride (CAS No: 871543-07-6), Glycyl-H 1152 dihydrochloride (CAS No: 913844-45-8), HA 1100 hydrochloride (CAS No: 155558-32-0), OXA 06 dihydrochloride, RKI 1447 dihydrochloride, SB 772077B dihydrochloride (CAS No: 607373-46-6), SR 3677 dihydrochloride (CAS No: 1072959-67-1), and TC-S 7001 (CAS No: 867017-68-3).

The concentration of the ROCK inhibitor in which the cells are cultured may be about 0.1 μM, 0.5 μM, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 40 μM, 50 μM, 60 μM, 70 μM, 80 μM, 90 μM, or 100 μM, for example.

Preferably, the ROCK inhibitor is Y27632 and the concentration of Y27632 in which the cells are cultured is about 10 μM.

According to the present method, for culturing the cells on a substrate coated with laminin-521 and E-cadherin in a medium comprising a Rho-associated, coiled-coil containing protein kinase (ROCK) inhibitor, the cells must be seeded on the substrate. The seeding density of the cells on the substrate may be about $1\times10^2$ cells/cm$^2$, $2\times10^2$ cells/cm$^2$, $3\times10^2$ cells/cm$^2$, $4\times10^2$ cells/cm$^2$, $5\times10^2$ cells/cm$^2$, $6\times10^2$ cells/cm$^2$, $7\times10^2$ cells/cm$^2$, $8\times10^2$ cells/cm$^2$, $9\times10^2$ cells/cm$^2$, $1\times10^3$ cells/cm$^2$, $2\times10^3$ cells/cm$^2$, $3\times10^3$ cells/cm$^2$, $4\times10^3$ cells/cm$^2$, $5\times10^3$ cells/cm$^2$, $6\times10^3$ cells/cm$^2$, $7\times10^3$ cells/cm$^2$, $8\times10^3$ cells/cm$^2$, $9\times10^3$ cells/cm$^2$, $1\times10^4$ cells/cm$^2$, $2\times10^4$ cells/cm$^2$, $3\times10^4$ cells/cm$^2$, $4\times10^4$ cells/cm$^2$, $5\times10^4$ cells/cm$^2$, $6\times10^4$ cells/cm$^2$, $7\times10^4$ cells/cm$^2$, $8\times10^4$ cells/cm$^2$, $9\times10^4$ cells/cm$^2$, $1\times10^5$ cells/cm$^2$, $2\times10^5$ cells/cm$^2$, $3\times10^5$ cells/cm$^2$, $4\times10^5$ cells/cm$^2$, $5\times10^5$ cells/cm$^2$, $6\times10^5$ cells/cm$^2$, $7\times10^5$ cells/cm$^2$, $8\times10^5$ cells/cm$^2$, $9\times10^5$ cells/cm$^2$, $1\times10^6$ cells/cm$^2$, $2\times10^6$ cells/cm$^2$, $3\times10^6$ cells/cm$^2$, $4\times10^6$ cells/cm$^2$, $5\times10^6$ cells/cm$^2$, $6\times10^6$ cells/cm$^2$, $7\times10^6$ cells/cm$^2$, $8\times10^6$ cells/cm$^2$, $9\times10^6$ cells/cm$^2$. In some embodiments, the seeding density may be about $1.1\times10^4$ cells/cm$^2$, $1.2\times10^4$ cells/cm$^2$, $1.3\times10^4$ cells/cm$^2$, $1.4\times10^4$ cells/cm$^2$, $1.5\times10^4$ cells/cm$^2$, $1.6\times10^4$ cells/cm$^2$, $1.7\times10^4$ cells/cm$^2$, $1.8\times10^4$ cells/cm$^2$, or $1.9\times10^4$ cells/cm$^2$. In a preferred embodiment, the seeding density is about $1.3\times10^4$ cells/cm$^2$.

As part of the present method, the cells may be cultured for about 1 day, 2 days, 3 days, 4 days, 5 days, 6 days, 7 days, 8 days, 9 days, 10 days or more before quantitating marker expression in the cultured cells. Preferably, the cells are cultured for about 5 days before quantitating marker expression in the cultured cells.

As part of the present method, the cells may be cultured in the presence of the ROCK inhibitor for about 1 day, 2 days, 3 days, 4 days, 5 days, 6 days, 7 days, 8 days, 9 days, 10 days or more before quantitating marker expression in the cultured cells.

After the cells have been cultured in the presence of the ROCK inhibitor, the cells may be cultured further in the absence of the ROCK inhibitor before quantitating marker expression in the cultured cells. In one embodiment, the cells are cultured further in the absence of the ROCK inhibitor for about 1 day, 2 days, 3 days, 4 days, 5 days, 6 days, 7 days, 8 days, 9 days, 10 days or more before quantitating marker expression in the cultured cells.

In a preferred embodiment, the cells are cultured in the presence of the ROCK inhibitor for about 3 days, then cultured further in the absence of the ROCK inhibitor for about 2 days before quantitating marker expression in the cultured cells.

In summary, expanding PSC-derived cells, such as MSCs, on a substrate, such as plastic culture ware, coated with laminin-521 and E-cadherin has been demonstrated to support the expansion of singularised, undifferentiated PSCs that reside within the population of PSC-derived cells, while simultaneously, a ROCK inhibitor enhances survival of the PSCs.

As used herein, "marker expression" refers to a gene that is expressed in residual, undifferentiated PSCs, but is not expressed, or only expressed at lower levels, in PSC-derived cells. Such a gene may be coding or non-coding, for example a mRNA, microRNA, or non-coding RNA.

Markers whose expression may be quantitated according to the present method include LIN28 (LIN28A), OCT4 (POU5F1), SOX2, FOXD3, NANOG, PODXL (protein isoforms of which are detected by antibodies TRA-1-60 and TRA-1-81), REX1 (ZFP42), SSEA1 (FUT4), SSEA4, DPPA2 and DPPA3. Preferably, marker expression is LIN28 expression. The LIN28 gene encodes the LIN28 protein that is an RNA-binding protein that promotes pluripotency and is highly expressed in PSCs, but is down-regulated in response to differentiation.

"Marker expression" may be quantitated as protein or mRNA expression. Preferably, marker expression is quantitated as mRNA expression.

Marker protein may be quantitated by processes involving gel electrophoresis (e.g. Western blot or two-dimensional gel electrophoresis), densitometry, fluorescence, luminescence, radioactivity, arrays, and/or mass spectrometry.

Marker mRNA may be quantitated by processes involving gel electrophoresis (e.g. Northern blot), densitometry, fluorescence, luminescence, radioactivity, arrays, and/or polymerase chain reaction (PCR). PCR generally relies on reverse transcription to generate marker cDNA from marker mRNA.

Preferably, marker expression is quantitated using PCR. Preferably, marker expression is quantitated using quantitative reverse transcription PCR (qRT-PCR). Preferably, qRT-PCR is real-time qRT-PCR in which a mRNA is reverse transcribed to a cDNA template and the cDNA template is amplified exponentially and quantitated by fluorescence in real-time.

Quantitating marker expression may be relative or absolute.

In one embodiment, quantitating marker expression is relative and relies on measuring the quantification cycle (Cq), which is the cycle where the fluorescent signal crosses the threshold for qRT-PCR assays. The Cq is inversely proportional to mRNA expression.

Relative quantitation of marker expression relies on comparison of marker expression in a test cell culture to marker expression in one or more reference cultures (i.e. controls).

A "reference culture" may be a positive control or a negative control. When the reference culture is a positive control, the reference culture of cells comprises PSCs. Preferably, such a reference culture comprises a known proportion of PSCs. That is, the reference culture is "spiked" with a known proportion of undifferentiated PSCs, thereby enabling comparison between the test culture and the reference culture. In this embodiment, quantitation may be both relative (e.g. use of Cq as a unit of quantitation) and absolute (e.g. application of Cq to a known quantity). This may also be referred to as semi-quantitative. Thus, lower marker expression in the culture of cells being tested than marker expression in the reference culture of cells indicates absence of residual, undifferentiated PSCs in the cultured cells. Alternatively, lower marker expression in the culture of cells being tested than marker expression in the reference culture of cells indicates presence of residual, undifferentiated PSCs in the cultured cells, but presence at a proportion lower than the known proportion of PSCs in the reference culture of cells.

The known proportion of PSCs in the reference culture may be 0.000001%, 0.000005%, 0.00001%, 0.00005%, 0.0001%, 0.0005%, 0.0006%, 0.0007%, 0.0008%, 0.0009%, 0.001%, 0.002%, 0.003%, 0.004%, 0.005%, 0.006%, 0.007%, 0.008%, 0.009%, or 0.01% of the total number of cells. In a preferred embodiment, the known proportion of PSCs in the reference culture is 0.001% of the total number of cells.

In some embodiments, marker expression is "normalised", which compensates for intra- and inter-kinetic variations (sample-to-sample and run-to-run variations). Normalised data are particularly useful when quantitating gene expression using qRT-PCR. Different methods of normalisation will be known to the person skilled in the art, including normalisation to one or more unregulated or constitutive "housekeeping" genes, e.g. GAPDH, ACTB, LDHA, NONO, PGK1, or PPIH, and normalisation to total RNA. In one embodiment, marker expression is normalised to GAPDH expression.

PCR requires nucleotide primers. The person skilled in the art will understand how to design primers for PCR and qRT-PCR, and primer/probe combinations for qRT-PCR. Primers for some genes are available commercially. Primer/probe combinations for some genes also are available commercially. For example, the following TaqMan® Gene Expression assays are available commercially, all with Catalog No. 4331182: human LIN28 (LIN28A) assay Hs00702808_s1; human OCT4 (POU5F1) assay Hs04260367_gH; human SOX2 Hs01053049_s1; human FOXD3 assay Hs00255287_s1; human NANOG assay Hs04399610_g1; human PODXL (protein isoforms of which are detected by antibodies TRA-1-60 and TRA-1-81) assay Hs01574644; human REX1 (ZFP42) assay Hs01938187_s1; human SSEA1 (FUT4) assay Hs01106466_s1; human DPPA2 assay Hs00414515_m1 and human DPPA3 assay Hs01931905_g1.

Primers or primer/probe combinations may be designed readily by the person skilled in the art using an online tool, for example, primer/probe combinations may be custom designed using a tool such as the Custom TaqMan® Assay Design Tool or the GenScript Real-time PCR (TaqMan®) Primer Design tool. Primers may be designed using tools such as Primer3Plus or PrimerQuest Tool. These tools are examples only, and many more are readily available to the person skilled in the art.

Alternatively or additionally, primers or primer/probe combinations may be designed readily from first principles, which include the following considerations.

PCR involves a cycle of: denaturing double stranded target DNA; annealing primers to the complementary regions of the single stranded DNA; extending the DNA by the action of DNA polymerase; and repeating, often for around 50 cycles. These steps are temperature sensitive and are commonly performed at 94° C., 60° C. and 70° C.

respectively. Good primer design is essential for successful reactions. Important design considerations include:
1. primer length, often 18-22 bp;
2. primer melting temperature (Tm), often in the range of 52-58° C.;
3. primer annealing temperature (Ta);
4. GC content, often 40-60%;
5. GC clamp, i.e. G or C bases located within the last five bases from the 3' end of primers;
6. primer and template secondary structures, i.e. intermolecular or intramolecular interactions, e.g. hairpins, self dimers, or cross dimers;
7. di-nucleotide repeats;
8. long runs of a single base;
9. 3' end stability;
10. cross homology/specificity;
11. amplicon length, often around 100 bp for qRT-PCR and around 500 bp for standard PCR;
12. Tm of product;
13. primer pair Tm, often <5° C.

Primer Tm may be calculated as follows:

$$Tm(K)=\{\Delta H/\Delta S+R \ln(C)\}, \text{ or } Tm(° C.)=\{\Delta H/\Delta S+R \ln(C)\}-273.15, \text{ where}$$

ΔH (kcal/mole): H is enthalpy and ΔH is the change in enthalpy
ΔS (kcal/mole): S is entropy and ΔS is the change in entropy.
ΔS (salt correction)=ΔS (1M NaCl)+0.368×N×ln([Na$^+$]), where
N is the number of nucleotide pairs in the primer (primer length −1)
[Na$^+$] is salt equivalent in mM
[Na$^+$] calculation:

$$[Na^+]=\text{Monovalent ion concentration}+4\times\text{free } Mg^{2+}.$$

Primer Ta may be calculated as follows:

$$Ta=0.3\times Tm(\text{primer})+0.7Tm(\text{product})-14.9$$

Example coding nucleotide sequences for human LIN28 (LIN28A), human OCT4 (POU5F1), human SOX2, human FOXD3, human NANOG, human PODXL, human REX1 (ZFP42), human SSEA1 (FUT4), human DPPA2 and human DPPA3 are provided in FIGS. 5 to 14 and SEQ ID NOs: 5 to 14, respectively. These sequences may be used by the person skilled in the art to design primers and primer/probe combinations.

qRT-PCR relies on fluorescence to quantitate gene expression, e.g. marker expression. Such fluorescence may comprise (1) a non-specific fluorescent dye that intercalates with any double-stranded DNA, i.e. the amplified PCR product, or (2) a sequence-specific oligonucleotide probe labelled with a fluorescent reporter that fluoresces only after hybridisation of the probe with its complementary sequence. One example of the first type of fluorescence is SYBR® Green (CAS No. 163795-75-3). Commonly, the second type comprises a quencher covalently attached to the 3'-end of the probe that quenches the fluorescent reporter until the quencher is released from the probe during amplification.

In one embodiment, the method for detecting residual, undifferentiated PSCs in a culture of cells differentiated from PSCs disclosed herein may further comprise generating a report reporting the proportion of residual, undifferentiated PSCs detected in the culture of PSC-derived cells.

In one embodiment, the method for detecting residual, undifferentiated PSCs in a culture of cells differentiated from PSCs disclosed herein may further comprise formulating the culture of PSC-derived cells in which residual, undifferentiated PSCs are absent or lower than a known proportion into a therapeutic composition for administering to a subject. The method may further comprise treating or preventing a condition in a subject by administering the culture of PSC-derived cells in which residual, undifferentiated PSCs are absent or lower than a known proportion, or a therapeutic composition comprising such PSC-derived cells, to the subject. The condition may be bone cysts, bone neoplasms, fractures, cartilage defects, osteoarthritis, ligament injury, osteogenesis imperfecta, osteonecrosis, osteoporosis, aplastic anaemia, graft versus host disease (GvHD), myelodysplastic syndrome, Type 1 diabetes, Type 2 diabetes, autoimmune hepatitis, liver cirrhosis, liver failure, dilated cardiomyopathy, heart failure, myocardial infarction, myocardial ischemia, Crohn's disease, ulcerative colitis, burns, epidermolysis bullosa, lupus erythematosus, rheumatoid arthritis, Sjogren's disease, systemic sclerosis, bronchopulmonary dysplasia, chronic obstructive airways disease, emphysema, pulmonary fibrosis, amyotrophic lateral sclerosis (ALS), Alzheimer's disease, brain injury, ataxia, degenerative disc disease, multiple system atrophy, multiple sclerosis, Parkinson's disease, retinitis pigmentosa, Romberg's disease, spinal cord injury, stroke, muscular dystrophy, limb ischaemia, kidney injury, lupus nephritis, endometriosis and complications of bone marrow or solid organ transplantation.

As used herein, the term "condition" includes a condition, disease or disorder, and symptoms thereof.

As used herein, the term "therapeutic composition" refers to PSC-derived cells as described herein that have been formulated for administration to a subject. Preferably, the therapeutic composition is sterile. This is readily accomplished by filtration through sterile filtration membranes. Preferably, the therapeutic composition is pyrogen-free.

As used herein, "formulating" refers to mixing a culture of cells in which residual, undifferentiated PSCs are absent or lower than a known proportion with optional pharmaceutically acceptable carriers, excipients or stabilisers, and maintaining cell viability. Acceptable carriers, excipients, or stabilisers are nontoxic to recipient subjects at the dosages and concentrations employed, and may include: buffers such as phosphate, citrate, and other organic acids; antioxidants including ascorbic acid and methionine; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulated pharmaceutical composition may also comprise other active compounds as necessary for the particular indication being treated, preferably those with complementary activities that do not adversely affect each other. The composition may comprise a cytotoxic agent, cytokine, and/or growth inhibitory agent. Such molecules are suitably present in combination in amounts that are effective for the purpose intended.

PSC-derived cells in which residual, undifferentiated PSCs are absent or lower than a known proportion, or a therapeutic composition comprising such PSC-derived cells, may be administered before, during or after a condition presents. In one embodiment, PSC-derived cells or a therapeutic composition are administered during inflammation. PSC-derived cells may be administered (a) as a preventative measure, (b) as soon as the condition has been diagnosed, (c) when other treatments fail, and/or (d) when a condition advances to a pre-defined degree of severity.

In one embodiment, PSC-derived cells in which residual, undifferentiated PSCs are absent or lower than a known proportion are, or a therapeutic composition comprising such PSC-derived cells is, pre-treated prior to administration. Pre-treatment may be with a growth factor or by gene editing, for example, where a growth factor may prime the PSC-derived cells and gene editing may confer a new therapeutic property on the PSC-derived cells.

It will be appreciated by the person skilled in the art that the exact manner of administering to a subject a therapeutically effective amount of PSC-derived cells in which residual, undifferentiated PSCs are absent or lower than a known proportion, or a therapeutic composition comprising such PSC-derived cells, will be at the discretion of the medical practitioner with reference to the condition to be treated or prevented. The mode of administration, including dosage, combination with other agents, timing and frequency of administration, and the like, may be affected by the diagnosis of a subject's likely responsiveness to treatment with the PSC-derived cells or therapeutic composition, as well as the subject's condition and history.

The PSC-derived cells in which residual, undifferentiated PSCs are absent or lower than a known proportion will be formulated, dosed, and administered in a fashion consistent with good medical practice. Factors for consideration in this context include the particular condition being treated or prevented, the particular subject being treated, the clinical status of the subject, the site of administration, the method of administration, the scheduling of administration, possible side-effects and other factors known to medical practitioners. The therapeutically effective amount of the PSC-derived cells in which residual, undifferentiated PSCs are absent or lower than a known proportion, or therapeutic composition comprising such PSC-derived cells, to be administered will be governed by such considerations.

PSC-derived cells in which residual, undifferentiated PSCs are absent or lower than a known proportion, or a therapeutic composition comprising such PSC-derived cells, may be administered systemically or peripherally, for example by routes including intravenous (IV), intra-arterial, intramuscular, intraperitoneal, intracerobrospinal, subcutaneous (SC), intra-articular, intrasynovial, intrathecal, intra-coronary, transendocardial, surgical implantation, topical and inhalation (e.g. intrapulmonary). Most preferably, the PSC-derived cells are, or therapeutic composition is, administered IV. PSC-derived cells or a therapeutic composition may be administered in combination with a scaffold of biocompatible material.

The term "therapeutically effective amount" refers to an amount of PSC-derived cells in which residual, undifferentiated PSCs are absent or lower than a known proportion, or a therapeutic composition comprising such PSC-derived cells, effective to treat a condition in a subject.

The terms "treat", "treating" or "treatment" refer to both therapeutic treatment and prophylactic or preventative measures, wherein the aim is to prevent or ameliorate a condition, disease or disorder in a subject or slow down (lessen) progression of a condition, disease or disorder in a subject. Subjects in need of treatment include those already with the condition, disease or disorder as well as those in which the condition, disease or disorder is to be prevented.

The terms "preventing", "prevention", "preventative" or "prophylactic" refers to keeping from occurring, or to hinder, defend from, or protect from the occurrence of a condition, disease or disorder, including an abnormality or symptom. A subject in need of prevention may be prone to develop the condition, disease or disorder.

The term "ameliorate" or "amelioration" refers to a decrease, reduction or elimination of a condition, disease or disorder, including an abnormality or symptom. A subject in need of treatment may already have the condition, disease or disorder, or may be prone to have the condition, disease or disorder, or may be in whom the condition, disease or disorder is to be prevented.

As used herein, the term "subject" refers to a mammal. The mammal may be a primate, particularly a human, or may be a domestic, zoo, or companion animal. Although it is particularly contemplated that the method and its resulting MSC or population of MSCs disclosed herein are suitable for medical treatment of humans, they are also applicable to veterinary treatment, including treatment of domestic animals such as horses, cattle and sheep, companion animals such as dogs and cats, or zoo animals such as felids, canids, bovids and ungulates.

Also disclosed herein is a culture of cells in which residual, undifferentiated PSCs are absent or lower than a known proportion when detected by the method of the first aspect.

Also disclosed herein is therapeutic composition when manufactured by the method of the second aspect.

Also disclosed herein is a kit for detecting residual, undifferentiated pluripotent stem cells (PSCs) in a culture of cells differentiated from PSCs, the kit comprising:
  laminin-521; and
  E-cadherin; and
  a ROCK inhibitor.

In one embodiment, the ROCK inhibitor is a ROCK inhibitor disclosed herein.

In one embodiment, the kit further comprises PCR primers and optionally a PCR probe for quantitating in the cultured cells expression of a marker of residual, undifferentiated PSCs. The PCR primers and probe are specific for the marker residual, undifferentiated PSCs. In one embodiment, the PCR primers and/or probe are PCR primers and/or probe disclosed herein.

In one embodiment, the kit comprises a ready-to-use composition for PCR, optionally qRT-PCR, referred to as a "master mix" comprising the components for PCR except for DNA template and primers, and optionally a probe. The components may include buffer, deoxynucleotide triphosphates (dNTPs), $Mg^{2+}$, and a polymerase. Master mixes are available commercially, for example 2× TaqMan® GE Master Mix.

In another embodiment, the kit further comprises a medium. In one embodiment, the medium is a medium disclosed herein. In one embodiment, the medium comprises the ROCK inhibitor.

In another embodiment, the kit further comprises a substrate. Such a substrate is suitable for culturing cells differentiated from PSCs in which residual, undifferentiated PSCs are to be detected. Preferably, the substrate is plastic culture ware such as a dish, multi-well plate, or flask. In one embodiment, the substrate is coated with the laminin-521 and E-cadherin.

In one embodiment, the kit comprises instructions for using the kit in a method comprising:
  culturing the cells on a substrate coated with laminin-521 and E-cadherin in a medium comprising a ROCK inhibitor;

quantitating marker expression in the cultured cells; and
comparing marker expression in the cultured cells with marker expression in a reference culture of cells comprising a known proportion of PSCs,
wherein lower marker expression in the culture of cells than marker expression in the reference culture of cells indicates absence of residual, undifferentiated PSCs in the cultured cells or presence of residual, undifferentiated PSCs in the cultured cells at a proportion lower than the known proportion of PSCs in the reference culture of cells.

In one embodiment, the kit comprises instructions for using the kit according to the method of the first aspect.

In another embodiment, the kit is used according to the method of the first aspect. This may be indicated by the term "when used".

In a preferred embodiment, iPSC-MSCs are cultured for 3 days in E8 Medium comprising 10 µM Y27632, a ROCK inhibitor, then cultured for 2 days in the absence of a ROCK inhibitor, and LIN28 expression is quantitated by qRT-PCR and normalised to GAPDH expression, allowing detection of 0.001% residual, undifferentiated iPSCs.

Other definitions that may be of assistance in understanding the present disclosure, particularly the examples, include the following.

a) TaqMan® Gene Expression (GE) Assay (20×): A type of real-time qRT-PCR assay available from Life Technologies that is designed using proprietary Applied Biosystems® software and reagents. These assays are used to quantitate specific mRNAs in a sample, and are available as pre-designed or custom assays. The TaqMan® GE Assays are provided as a 20× mix of gene specific primers and probe.

i) FAM™/MGB-NFQ Probe: A fluorescent reporter molecule (FAM: 6-carboxyfluorescein), covalently attached to the 5'-end of a TaqMan® probe. MGB-NFQ is a Minor Groove Binder-Non-Fluorescent Quencher molecule, covalently attached to the 3'-end of the TaqMan® probe. During amplification, the probe is cleaved, releasing the reporter from the quencher. The resulting fluorescent signal is proportional to the mRNA concentration in the sample. Other fluorescent dyes are available in place of FAM™. VIC® is commonly used for Endogenous Control Genes used for normalisation, such as GAPDH.

b) 2× TaqMan® GE Master Mix: contains AmpliTaq Gold® DNA Polymerase, UP (Ultra Pure) for hot start activation, a blend of dNTPs with dTTP/dUTP and Uracil-DNA Glycosylase (UDG) to minimise carry-over PCR contamination, and a passive internal reference based on proprietary ROX™ dye.

c) cDNA: Complementary DNA, which is reverse transcribed from mRNA using Reverse Transcriptase (RT).

d) mRNA: messenger RNA.

e) gDNA: genomic DNA.

f) Template: a nucleic acid target (e.g., cDNA) intended to be amplified by PCR.

g) Total RNA: a complex mixture of RNA species, including mRNA (~1-5%), ribosomal RNA (rRNA) (~80%), transfer RNA (tRNA) and micro RNAs (miRNAs). The exact composition varies, depending on the cell type.

h) RNase: Ribonuclease, a class of enzymes that degrade RNA and are very difficult to inactivate.

i) Endogenous Control Gene: a positive control gene that is expressed in all sample types. GAPDH: Glyceraldehyde-3-phosphate dehydrogenase is a common endogenous control gene used for normalisation.

j) Target Gene: a gene of interest that is differentially expressed in stem cells versus differentiated cells (e.g., iPSC vs. iPSC-MSC), such as LIN28.

k) +RT and −RT Master Mixes: contain the reagents needed for reverse transcription of Total RNA samples. −RT is a negative control containing Total RNA, but lacking Reverse Transcriptase. The −RT samples test for gDNA contamination of Total RNA samples.

l) +/−RT Reaction Mixes: A combination of +/−RT Master Mix with each Total RNA sample or control for reverse transcription.

m) cDNA Amplification Mix: a combination of 2× TaqMan® GE Master Mix with each +/−RT Reaction Mix.

n) GE Assay Mix (e.g., LIN28 or GAPDH Assay Mix): A combination of a 20× TaqMan® GE Assay with each cDNA Amplification Mix for real-time qRT-PCR.

o) No Template Control (NTC): A type of Negative Control (NEG) in which Total RNA is replaced by water in the +/−RT cDNA reaction. Used to detect contamination of reagents by nucleic acid templates.

p) SNP: Single Nucleotide Polymorphism.

q) Cq: Quantification cycle (e.g., Cq(X)) is the cycle where the fluorescent signal crosses the threshold for real-time qPCR and qRT-PCR assays. The Cq is inversely related to the mRNA concentration. As the Cq increases, the mRNA concentration decreases, and vice versa. "Cq(50)" indicates that 50 cycles were run. "No Cq(50)" indicates that no Cq value was generated in 50 cycles.

EXAMPLES

Example 1—Production of iPSC-MSCs

Materials

TABLE 1

Reagents

| Description | Vendor/Cat # or Ref # |
|---|---|
| DMEM/F12 Base Medium | Invitrogen/A1516901 |
| E8 supplement | Invitrogen/A1517101 |
| vitronectin | Life Technologies/A14700 |
| collagen IV | Sigma/C5533 |
| H-1152 ROCK Inhibitor | EMD Millipore/555550 |
| Y27632 dihydrochloride ROCK Inhibitor | Tocris/1254 |
| FGF2 | Waisman Biomanufacturing/WC-FGF2-FP |
| human endothelial-SFM | Life Technologies/11111-044 |
| stemline II hematopoietic stem cell expansion medium | Sigma/S0192 |
| GLUTAMAX | Invitrogen/35050-061 |
| insulin | Sigma/I9278 |
| lithium chloride (LiCl) | Sigma/L4408 |
| collagen I solution | Sigma/C2249 |
| fibronectin | Life Technologies/33016-015 |
| DMEM/F12 | Invitrogen/11330032 |
| recombinant human BMP4 | Peprotech/120-05ET |
| activin A | Peprotech/120-14E |
| Iscove's modified Dulbecco's medium (IMDM) | Invitrogen/12200036 |
| Ham's F12 nutrient mix | Invitrogen/21700075 |
| sodium bicarbonate | Sigma/S5761 |
| L-ascorbic acid 2-phosphate $Mg^{2+}$ | Sigma/A8960 |
| 1-thioglycerol | Sigma/M6145 |
| sodium selenite | Sigma/S5261 |
| non essential amino acids | HyClone/SH30853.01 |
| chemically defined lipid concentrate | Invitrogen/11905031 |
| embryo transfer grade water | Sigma/W1503 |
| polyvinyl alcohol (PVA) | MP Bio/151-941-83 |
| holo-transferrin | Sigma/T0665 |
| ES-CULT M3120 | Stem Cell Technologies/03120 |
| STEMSPAN serum-free expansion medium (SFEM) | Stem Cell Technologies/09650 |

TABLE 1-continued

Reagents

| Description | Vendor/Cat # or Ref # |
|---|---|
| L-ascorbic acid | Sigma/A4544 |
| PDGF-BB | Peprotech/110-14B |

The reagents listed in Table 1 are known to the person skilled in the art and have accepted compositions, for example IMDM and Ham's F12. GLUTAMAX comprises L-alanyl-L-glutamine dipeptide, usually supplied at 200 mM in 0.85% NaCl. GLUTAMAX releases L-glutamine upon cleavage of the dipeptide bond by the cells being cultured. Chemically defined lipid concentrate comprises arachidonic acid 2 mg/L, cholesterol 220 mg/L, DL-alpha-tocopherol acetate 70 mg/L, linoleic acid 10 mg/L, linolenic acid 10 mg/L, myristic acid 10 mg/L, oleic acid 10 mg/L, palmitic acid 10 mg/L, palmitoleic acid 10 mg/L, pluronic F-68 90 g/L, stearic acid 10 mg/L, TWEEN 80® 2.2 g/L, and ethyl alcohol. H-1152 and Y27632 are highly potent, cell-permeable, selective ROCK (Rho-associated coiled coil forming protein serine/threonine kinase) inhibitors.

TABLE 2

IF6S medium (10X concentration)

| 10X IF6S | Quantity | Final Concentration |
|---|---|---|
| IMDM | 1 package, powder for 1 L | 5X |
| Ham's F12 nutrient mix | 1 package, powder for 1 L | 5X |
| sodium bicarbonate | 4.2 g | 21 mg/mL |
| L-ascorbic acid 2-phosphate $Mg^{2+}$ | 128 mg | 640 µg/mL |
| 1-thioglycerol | 80 µL | 4.6 mM |
| sodium selenite (0.7 mg/mL) | 24 µL | 84 ng/mL |
| GLUTAMAX | 20 mL | 10X |
| non essential amino acids | 20 mL | 10X |
| chemically defined lipid concentrate | 4 mL | 10X |
| embryo transfer grade water | To 200 mL | NA |

TABLE 3

IF9S medium (1X concentration; based on IF6S)

| IF9S | Quantity | Final Concentration |
|---|---|---|
| IF6S | 5 mL | 1X |
| polyvinyl alcohol (PVA; 20 mg/mL) | 25 mL | 10 mg/mL |
| holo-transferrin (10.6 mg/mL) | 50 µL | 10.6 µg/mL |
| insulin | 100 µL | 20 µg/mL |
| embryo transfer grade water | To 50 mL | NA |

TABLE 4

Differentiation medium (1X concentration; based on IF9S)

| Differentiation Medium | Quantity | Final Concentration |
|---|---|---|
| IF9S | 36 mL | 1X |
| FGF2 | 1.8 µg | 50 ng/mL |
| LiCl (2M) | 36 µL | 2 mM |
| BMP4 (100 µg/mL) | 18 µL | 50 ng/mL |
| Activin A (10 mg/mL) | 5.4 µL | 1.5 ng/mL |

TABLE 5

Mesenchymal colony forming medium (1X concentration)

| M-CFM | Quantity | Final Concentration |
|---|---|---|
| ES-CULT M3120 | 40 mL | 40% |
| STEMSPAN SFEM | 30 mL | 30% |
| human endothelial-SFM | 30 mL | 30% |
| GLUTAMAX | 1 mL | 1X |
| L-ascorbic acid (250 mM) | 100 µL | 250 µM |
| LiCl (2M) | 50 µL | 1 mM |
| 1-thioglycerol (100 mM) | 100 µL | 100 µM |
| FGF2 | 600 ng | 20 ng/mL |

TABLE 6

Mesenchymal serum-free expansion medium (1X concentration)

| M-SFEM | Quantity | Final Concentration |
|---|---|---|
| human endothelial-SFM | 5 L | 50% |
| STEMLINE II HSFM | 5 L | 50% |
| GLUTAMAX | 100 mL | 1X |
| 1-thioglycerol | 87 µL | 100 µM |
| FGF2 | 100 µg | 10 ng/mL |

Method

1. Thawed iPSCs in E8 Complete Medium (DMEM/F12 Base Medium+E8 Supplement)+1 µM H1152 on Vitronectin coated (0.5 µg/cm$^2$) plastic ware. Incubated plated iPSCs at 37° C., 5% $CO_2$, 20% $O_2$ (normoxic).
2. Expanded iPSCs three passages in E8 Complete Medium (without ROCK inhibitor) on Vitronectin coated (0.5 µg/cm$^2$) plastic ware and incubated at 37° C., 5% $CO_2$, 20% $O_2$ (normoxic) prior to initiating differentiation process.
3. Harvested and seeded iPSCs as single cells/small colonies at 5×10$^3$ cells/cm$^2$ on Collagen IV coated (0.5 µg/cm$^2$) plastic ware in E8 Complete Medium+10 µM Y27632 and incubated at 37° C., 5% $CO_2$, 20% $O_2$ (normoxic) for 24 h.
4. Replaced E8 Complete Medium+10 µM Y27632 with Differentiation Medium and incubated at 37° C., 5% $CO_2$, 5% $O_2$ (hypoxic) for 48 h.
5. Harvested colony forming cells from Differentiation Medium adherent culture as a single cell suspension, transferred to M-CFM suspension culture and incubated at 37° C., 5% $CO_2$, 20% $O_2$ (normoxic) for 12 days.
6. Harvested and seeded colonies (Passage 0) on Fibronectin/Collagen I coated (0.67 µg/cm$^2$ Fibronectin, 1.2 µg/cm$^2$ Collagen I) plastic ware in M-SFEM and incubated at 37° C., 5% $CO_2$, 20% $O_2$ (normoxic) for 3 days.
7. Harvested colonies and seeded as single cells (Passage 1) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
8. Harvested and seeded as single cells (Passage 2) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
9. Harvested and seeded as single cells (Passage 3) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
10. Harvested and seeded as single cells (Passage 4) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.

11. Harvested and seeded as single cells (Passage 5) at $1.3 \times 10^4$ cells/cm² on Fibronectin/Collagen 1 coated plastic ware in M-SFEM and incubated at 37° C., 5% $CO_2$, 20% $O_2$ (normoxic) for 3 days.

12. Harvested passage 5 (P5) iPSC-MSCs as single cells and froze final product.

Example 2—Quantitation of Residual Undifferentiated Stem Cells by qRT-PCR

1) Purpose

This example protocol describes quantitation of residual, undifferentiated iPSCs by TaqMan® Gene Expression Assays (qRT-PCR). Although detection of undifferentiated iPSCs amongst iPSC-MSCs using LIN28 expression is exemplified, the protocol is applicable generally to PSC-derived cell culture using any PSC marker differentially expressed in PSCs, but not expressed in PSC-derived cells. The protocol is intended for Quality Control of PSC-derived cells destined for formulation into a therapeutic composition.

2) Materials a) Materials for iPSC-MSC Laminin-521/E-Cadherin Expansion Culture Protocol:

i) LN521™ Human rLaminin-521, Biolamina, Catalog No. LN521-03 ii) E-Cadherin, Human Recombinant, Advanced BioMatrix, Catalog No. 5085-0.1MG iii) Dulbecco's Phosphate-Buffered Saline (1×) with $Mg^{2+}$ and $Ca^{2+}$ (DPBS++) (6×500 mL), Corning/Mediatech, Catalog No. 21-030-CV or equivalent iv) HyClone™ Dulbecco's Phosphate Buffered Saline without $Mg^{2+}$ and $Ca^{2+}$, solution, (DPBS--), GE Healthcare Life Sciences, Catalog No. SH30028 or equivalent v) ROCK Inhibitor Y27632, Sigma-Aldrich, Catalog No. Y0503-1MG or Y0503-5MG vi) Essential 8™ Medium (Kit), Thermo Fisher Scientific, Catalog No. A1517001

(1) Essential 8™ Basal Medium (500 mL)
    (2) Essential 8™ Supplement (Vitronectin) (10 mL)

vii) TrypLE™ Select Enzyme (1×), no phenol red (100 mL), Thermo Fisher Scientific, Catalog No. 12563011 viii) Dimethyl sulfoxide (DMSO), Sigma-Aldrich, Catalog No. D2650 ix) Falcon® 75 cm² Rectangular Canted Neck Cell Culture Flask with Vented Cap, Corning Life Sciences, Catalog No. 353136 or equivalent x) Falcon® Cell Scraper with 25 cm Handle and 1.8 cm Blade, Sterile, Corning Life Sciences, Catalog No. 353086 or equivalent xi) HyClone™ 0.4% Trypan Blue, Thermo Fisher Scientific, Catalog No. SV30084 or equivalent xii) Hemocytometer with cover slip, Reichert Right Line or equivalent b) RNeasy® Protect Cell Mini Kit (50): QIAGEN® Catalog No. 74624. Consists of two QIAGEN® products:

i) RNAprotect® Cell Reagent (Box 1 of 2): Designed for cultured or sorted cells. Can be added directly to cells in culture medium. Arrests gene expression patterns, providing immediate stabilization of Total RNA. Samples can be stored at 4° C., −20° C. or archived at −80° C.

ii) RNeasy® Plus Mini Kit (Box 2 of 2): Designed to isolate total RNA from a variety of sample types. "Plus" indicates that the kit contains genomic DNA (gDNA) Eliminator Columns and related reagents.

c) QIAshredder (50): QIAGEN® Catalog No. 79654. Required to homogenise cell lysates for RNA isolation.

d) RNase-Free DNase Set (50 preps), QIAGEN®, Catalog No. 79254. For on-membrane DNase treatment using QIAGEN® RNA purification kits.

e) Ethanol (96-100%): Fisher BioReagents, Molecular Biology Grade, Absolute (200 Proof), 100 mL, Fisher Scientific Catalog No. BP2818100 or equivalent. Required for the QIAGEN® RNeasy® Plus Mini Kit.

f) UltraPure™ DNase/RNase-Free Distilled Water, Life Technologies, Catalog No. 10977-015 or equivalent.

g) β-Mercaptoethanol (β-ME), 14.3 M, Thermo Fisher Scientific, Catalog No. BP176-100 or equivalent. Required for the QIAGEN® RNeasy® Plus Mini Kit to inactivate RNases.

h) Safetec Green-Z™ Biohazard Fluid Control Powder, Thermo Fisher Scientific, Catalog No. 19-023-901. For disposal of the RNAprotect® Cell Reagent, which is an environmental hazard.

i) RNase AWAY™ Decontamination Reagent (250 mL), Life Technologies, Catalog No. 10328-011 or equivalent. Apply the ready-to-use solution to surfaces, such as lab benches, pipets, glassware or plastic ware. Rinse with Milli-Q water to eliminate RNase and DNA contamination.

j) High-Capacity RNA-to-cDNA™ Kit (50): Thermo Fisher Scientific, Catalog No. 4387406 k) SUPERase·In™ RNase Inhibitor: Thermo Fisher Scientific, Catalog No. AM2694 l) TaqMan® Gene Expression Master Mix (2×): Thermo Fisher Scientific, Catalog No. 4369016 (1-Pack, 5 mL: 200×50 μL Rxs)

m) Ambion® RT-PCR Grade Water: Thermo Fisher Scientific Catalog No. AM9935 (10×1.5 ml) (preferred) or equivalent. Note: AM9935 is autoclaved, membrane-filtered and is not DEPC-treated. AM9935 is tested for prokaryotic (16S rRNA) and eukaryotic (18S rRNA) genomic DNA contamination by real-time PCR. It is certified RNase-free, DNase-free and genomic DNA-free.

n) TaqMan® Gene Expression Assay(s), which contain a 20×, ready-to-use mix of primers and FAM/MGB-NFQ probe in TE. FAM is the most common fluorescent reporter. (1×=250 nM TaqMan Probe+900 nM of each PCR primer (forward & reverse)). The catalog numbers below refer to custom assay sizes. Light sensitive. Preferably store in one-time use aliquots at −20° C. in 1.5 ml Ambion® Non-Stick Tubes.

i) Custom TaqMan® Gene Expression Assays (20×, Single Tube), Thermo Fisher Scientific, made to order. (Note that custom assays can only be ordered with FAM-MGB probes.)

(1) Catalog No. 4331348 (Small=360 rxn @ 20 μL qRT-PCR)
      (2) Catalog No. 4332078 (Medium=750 rxns @ 20 μL qRT-PCR)

ii) LIN28 Custom TaqMan® Gene Expression Assay, Thermo Fisher Scientific; Catalog No: 4331348; Assay ID: AIVI48S; Assay Name: LIN28.QRT-PCR; Scale: S: 360 rxns; Made to Order. This is a custom designed assay with known primer and probe sequences as disclosed in Kuroda, et al. (PLoS ONE 7, 1-9 (2012) *Highly Sensitive In Vitro Methods for Detection of Residual Undifferentiated Cells in Retinal Pigment Epithelial Cells Derived from Human iPS Cells*). LIN28 Probe sequence (5'→3') CGCATGGGGTTCGGCTTCCTGTCC (SEQ ID NO: 15); LIN28 forward primer sequence (5'→3')

CACGGTGCGGGCATCTG (SEQ ID NO: 16); LIN28 reverse primer sequence (5'→3') CCTTCCATGTGCAGCTTACTC (SEQ ID NO: 17).

iii) TaqMan® Endogenous Control Assays: These assays have been predesigned and may be inventoried. Endogenous Controls are available with FAM-MGB or VIC-MGB probes. Preferably select the VIC-MGB probe to distinguish the control assay from the distinguishing assay.

(1) GAPDH TaqMan® Gene Expression Assay (Gene Symbol: GAPDH, hCG2005673), Life Technologies; Catalog No: 4448489; Assay ID: Hs02758991_g1 (VIC-MGB Probe); Made to order. The "Best Coverage" assay was chosen from multiple predesigned GAPDH assays. This assay spans an intron and should therefore not detect genomic DNA.

o) Ambion® Non-Stick RNase-free Microfuge Tubes (1.5 ml): Life Technologies Catalog No. AM12450. Note: AM12450 1.5 ml tubes have a low binding surface and are certified RNase-free and DNase-free. Preferably used to store aliquots of the Custom TaqMan® GE Assay (20×) and prepare cDNA.

p) 1.5 mL Screw Cap Microtube (Sarstedt 72.692.005): Fisher Scientific Catalog No. 50809238 or equivalent; Conical Bottom, Sterile With Assembled O-Ring Cap. Preferably used to prepare cDNA Amplification Mixes. The exterior-threaded screw cap prevents the generation of aerosols, which could otherwise cause PCR contamination.

q) White Hard-Shell Low-Profile 96-Well Skirted PCR Plates: Bio-Rad Catalog No. HSP-9655. A white plate will reduce background noise and increase the fluorescent signal over clear 96-well plates and tubes. Strip tubes should not be used for this procedure.

r) Microseal 'B' Adhesive Seals (100): Bio-Rad Catalog No. MSB-1001. This is the recommended, optically clear, plate sealer for the Hard-Shell 96-well plates.

s) Sealing Roller: Bio-Rad Catalog No. MSR-0001. Used to seal a Hard-Shell 96-well plate with a Microseal 'B' Adhesive Seal.

t) Bio-Rad CFX96 Real-Time PCR Detection System with Bio-Rad CFX Software (ID 0394) or equivalent.

u) Eppendorf MiniSpin Plus Microcentrifuge (ID 0569) or equivalent.

v) Nanodrop 2000 UV-Visible Spectrophotometer (ID 0504) or equivalent.

3) Procedure a) Preparation of P5 iPSC-MSCs Final Product (1 Vial) for qRT-PCR Analysis Using Selective Expansion of Residual Undifferentiated iPSCs.

i) This procedure selectively expands undifferentiated iPSCs in a background of iPSC-MSCs, in order to increase the sensitivity of qRT-PCR for residual undifferentiated iPSCs.

ii) Preparation of Cell Culture Media:

(1) Preparation of E8 Complete Medium (E8CM):

(a) Thaw E8 Supplement overnight at 2-8° C.

(b) Remove 10 ml of E8 Basal Medium from 500 ml bottle.

(c) Add 10 ml of E8 supplement to 490 ml of E8 Basal Medium. Mix well and store at 2-8° C. Expires 2 weeks after preparation.

(2) Preparation of E8CM+10 μM Y27632 Medium:

(a) Prepare 10 mM Y27632 by adding 312 μl DPBS-- (without $Ca^{2+}$ & $Mg^{2+}$) to 1 mg of Y27632. Aliquot and freeze at −20° C.

(b) Add 1 μl of 10 mM Y27632 to each ml of E8CM for a final concentration of 10 μM Y27632 (e.g. 75 μl of 10 mM Y27632 to 75 ml E8CM). Store at 4° C. Expires 2 weeks after preparation.

iii) Preparation of Freeze Medium (E8CM+20% DMSO):

(1) Prepare 10 ml of Freeze Medium as follows: Combine 8 ml E8CM with 2 ml DMSO. Transfer to 4° C. to chill prior to use.

(2) Add 1 μl of 10 mM Y27632 to each ml of E8CM for a final concentration of 10 μM Y27632 (e.g. 75 μl of 10 mM Y27632 to 75 ml E8CM). Store at 4° C. Expires 2 weeks after preparation.

iv) Preparation of Laminin-521/E-Cadherin Coating (in DPBS++):

(1) Thaw Laminin-521 and E-Cadherin overnight at 2-8° C.

(2) Prepare the coating material (30 ml required for 2×T75 flasks):

| Materia | Conc. | Volume | T75 - |
|---|---|---|---|
| DPBS++ | 1X | 180 μl | 13.5 ml |
| Laminin | 100 | 20 μl | 1.5 ml |
| E- | 500 | 0.444 | 33.3 μl |

(3) Coat culture ware (2×T75 flasks) and store at 2-8° C. for at least overnight prior to use (1 month expiration). Make sure that the coating solution covers the entire culture area.

v) Preparation of Expansion Culture (1) Minimum 1 hour before seed, remove coating material from flasks and add 15 ml E8CM+10 μM Y27632/T75. Let equilibrate at 37° C.

(2) Thaw P5 iPSC-MSC in a 37° C. water bath.

(3) Transfer the contents of the vial into a 15 ml tube containing 9 ml of E8CM+10 μM Y27632.

(4) Centrifuge at 200×g for 5 minutes.

(5) Aspirate the supernatant and resuspend the pellet in 5 ml E8CM+10 μM Y27632.

(6) Count the cells using a hemocytometer. Estimated concentration $5×10^6$ cells/5 ml=$1×10^6$ cells/ml. Suggested dilution in trypan blue is 1:2. Calculate the percent viability.

(7) Calculate the number of cells required to seed each T75 flask at $1.3×10^4$ cells/$cm^2$ or $1×10^6$ cells/T75).

(8) Seed the Laminin-521/E-Cadherin coated flasks with the calculated number of cells.

(9) Feed the cells on the following schedule:

(a) Day 1—No feed.

(b) Day 2—Feed each T75 flask with 15 ml E8CM+10 μM Y27632.

(c) Day 3—No feed.

(d) Day 4 & 5—Feed each T75 flask with 15 ml E8CM (without Y27632).

(10) Check the cultures daily for signs of microbial contamination (e.g., turbidity). Discard any contaminated cultures and start over at Step 3)a).

vi) Harvest (Day 6 Post-Seed)

(1) Notes: Cell are difficult to detach from Laminin-521/E-cadherin coated culture ware. Use of cell scrapers is recommended to get all the cells to detach. The average harvest density is $4×10^4$ cells/$cm^2$ or $3×10^6$ cells/T75 flask. If an insufficient number of cells is harvested from a single T75 flask (<$2×10e^6$ cells) harvest of the second T75 may be required.

(2) Aspirate the growth medium and rinse the flask with 10 ml DPBS--.

(3) Add 8 ml TrypLE to the T75 flask. Incubate at 37° C. for 15 minutes.

(4) Rap flask firmly to dislodge the cells and transfer to a 50 ml conical tube (approximately 8 ml).

(5) Add 8 ml E8CM+10 µM Y27632 to the flask, pipet up and down and combine with cell suspension in the 50 ml tube (16 ml total).

(6) Add 8 ml E8CM+10 µM Y27632 to the flask and use a sterile disposable cell scraper to gently scrape off the cells. Collect the cells by rinsing the scraped surface with medium and combine with the cell suspension (24 ml total).

(7) Repeat scraping after adding an additional 8 ml E8CM+10 µM Y27632 to the flask. Collect cell suspension as above (32 ml total).

(8) Centrifuge cells at 200×g for 10 minutes. Aspirate the supernatant.

(9) Resuspend the cell pellet in E8CM+10 µM Y27632 and count cells. Suggested resuspension volume is 2 ml with estimated concentration $3\times10^6$ cells/2 ml=$1.5\times10^6$ cells/ml. Suggested dilution in trypan blue is 1:2. In order to accurately count, cells may require dissociation into single cells using a 1 ml pipet tip.

(a) Count the cells using a hemocytometer.

(b) The required percent viability is ≥70%. The required yield is ≥$2\times10^6$ cells.

(10) Spin cells at 200×g for 10 minutes. Aspirate supernatant.

(11) Resuspend cell pellet in E8CM at $2\times10^6$ cells/ml.

vii) Freeze the Cells Prior to Analysis.

(1) Add an equal volume of COLD Freeze Medium (E8CM with 20% DMSO) for a final concentration of 1×106 cells/ml.

(2) Add 1 ml of cell suspension to each cryovial.

(3) Immediately transfer cryovials to −80° C. freezer.

(4) Transfer to liquid Nitrogen tank the next day.

b) Preparation of Reagents for the RNeasy® Plus Mini Kit:

i) Preparation of QIAGEN® Buffer RPE wash solution:

(1) Add 100% ethanol, as indicated on the bottle, to Buffer RPE concentrate (i.e., 44 mL for a 50 prep RNeasy® Protect Cell Mini Kit).

ii) Preparation of 70% Ethanol:

(1) Combine 7 mL of 100% Ethanol with 3 mL of Nuclease-Free Water. Expiration is one month after preparation.

iii) Preparation of Lysis Buffer for Total RNA isolation:

(1) Add 10 µL β-mercaptoethanol (β-ME) per 1 mL of Buffer RLT Plus before use, using a chemical fume hood.

iv) Preparation of RNase-free DNase for the QIAGEN® RNase-Free DNase Set:

(1) Add the indicated amount of RNase-Free Water (i.e., 550 µL) to the lyophilised DNase, using a sterile needle and syringe. Gently resuspend the DNase by inversion. Do not vortex. Store the reconstituted DNase at −20° C. in 20 µL aliquots, preferably in Ambion® Non-Stick RNase-free Microfuge Tubes. The reconstituted RNase expires nine months after preparation. Store the remaining kit components at 2-8° C.

c) Preparation of Cultured Cells for Total RNA Isolation, Using RNAprotect® Cell Reagent.

i) RNAprotect® Cell Reagent immediately stabilises Total RNA in treated cells, preserving the gene expression profile. The reagent is added directly to cells, with or without medium present.

Frozen cells in DMSO can also be prepared, using a modified protocol.

(1) The recommended cell number is 1-$2\times10^6$ cells per Total RNA miniprep. This can be increased to a maximum of $5\times10^6$ cells per miniprep, without changing the reagent volumes. For larger cell numbers, process multiple minipreps or use an RNA midiprep procedure, following the manufacturer's protocol.

(2) Use a ratio of 1 mL of sample to 5 mL of RNAprotect® Cell Reagent.

ii) Prepare an appropriate number of 15 mL tubes containing 5 mL of RNAprotect® Cell Reagent.

iii) Frozen Cells: Place vials of frozen cells on dry ice to prevent thawing. Do not thaw the cells prior to reagent addition. Process one vial at a time to maximise protection of the RNA.

(1) Transfer ~750 µL of RNAprotect® Cell Reagent from one 15 mL tube to a cryovial of frozen cells containing ~1 mL of freezing medium. Adjust the volumes as necessary for other scenarios. Do not overfill.

(a) Use high quality, low-retention pipet tips to prevent pipetting losses.

(2) Immediately vortex the mixture for ~10 seconds. Quickly transfer the partially thawed mixture back to the same 15 mL tube containing RNAprotect® Cell Reagent.

(3) Repeat steps 3)c)iii)(1) and 3)c)iii)(2) until the mixture is completely thawed. This will take 3-4 iterations.

(4) Mix well by vortexing, until the sample is homogenous.

iv) Proceed immediately with Total RNA isolation or store the prepared samples in RNAprotect® Cell Reagent. Store samples at 2-8° C. for up to 4 weeks or archive at −20° C. or −80° C.

d) Preparation of Cell Lysates for Total RNA Isolation.

i) If frozen, thaw the RNAprotect® cell mixture at room temperature without mixing.

ii) Centrifuge the RNAprotect® cell mixture for 5 minutes at 4000 rpm (Sorvall ID 0018 or equivalent) to collect the cells and any precipitate that may have formed. A visible white pellet should form.

iii) Remove as much supernatant as possible to a waste container. Flick the tube or vortex to loosen the pellet. This is very important for complete solubilization in the next step.

(1) Add 350 µL of freshly prepared Buffer RLT Plus+β-ME to the pellet. Vortex vigorously for 1-2 minutes, until the pellet is completely dissolved. If needed, the lysate can be stored at −80° C. Thaw at room temperature and vortex before use.

e) Isolation of Total RNA Using the QIAGEN® RNeasy® Plus Mini Kit.

All steps are performed at room temperature. Isolate Total RNA from the following cryopreserved samples. Elute in 30 µL Nuclease-Free Water.

1: iPSC-MSC (non-expanded) (Reference culture)
2: iPSC-MSC (expanded) (Reference culture)
3: iPSC-MSC plus 0.001% iPSC Spike (non-expanded) (Reference culture)
4: iPSC-MSC plus 0.001% iPSC Spike (expanded) (Reference culture)
5: iPSC-MSC P5 Final Product (non-expanded)
6: iPSC-MSC P5 Final Product (expanded)

i) Transfer the lysate to a QIAshredder. Centrifuge at full speed for 2 minutes to shear and homogenise the lysate. A thin round pellet may form in the bottom of the collection tube.

ii) Transfer the homogenised lysate to an assembled gDNA Eliminator spin column, avoiding any pelleted material. Centrifuge at full speed for 30 seconds. If necessary, repeat until all of the lysate has passed through the spin column.

iii) Add 350 µL of 70% ethanol to the flow-through and mix well by pipetting. Do not centrifuge. Immediately transfer the mixture to an assembled RNeasy® spin column, with any precipitate that may have formed.

iv) Gently close the cap and centrifuge at full speed for 15 seconds. Discard the flow-through from the collection tube. The RNA is now bound to the RNeasy® spin column.

v) On-Membrane DNase Treatment:

(1) For maximum removal of genomic DNA, the bound RNA is treated with RNase-Free DNase.

(a) Add 350 µL Buffer RW1 to the spin column. Gently close the cap and centrifuge at full speed for 15 seconds. Discard the flow-through from the collection tube.

(b) For each sample, combine 20 µL of reconstituted DNase, 140 µL Buffer RDD and 2 µL SUPERase. In™. Mix gently by pipetting and combine all into one tube. Do not vortex.

(c) Pipet 80 µL of the DNase mix directly onto the center of the RNeasy® membrane. Incubate at room temperature for 20 minutes.

(d) Add 350 µL Buffer RW1 to the spin column. Gently close the cap and centrifuge at full speed for 15 seconds. Discard the flow-through from the collection tube.

vi) Add 500 µL Buffer RPE to the spin column. Gently close the cap and centrifuge at full speed for 15 seconds. Discard the flow-through from the collection tube.

vii) Repeat the wash by adding 500 µL Buffer RPE to the spin column. Gently close the cap and centrifuge at full speed for 2 minutes.

viii) Transfer the spin column to a fresh 2 mL collection tube. Centrifuge at full speed for 1 minute to remove any residual wash solution.

ix) Transfer the spin column to a 1.5 mL collection tube. Add 30 µL RNase-free water directly to the membrane. Gently close the cap and centrifuge at full speed for 1 minute to elute the RNA.

x) Discard the spin column and cap the tube. Label the tube with the date and sample ID.

xi) Normalise the volume of each Total RNA sample to 30 µL.

(1) Set a 10-100 µL pipet to 30 µL and measure the eluate volume.

(2) If the volume is less than 30 µL, add Nuclease-Free Water from the RNeasy® kit to a final volume of 30 µL.

(3) The sample is now normalised to the starting number of cells.

xii) Determine the Total RNA concentration for each sample using a Nanodrop 2000.

(1) Clean the sample pedestal with Milli-Q water before launching the software, to remove any potential contamination from previous use.

(2) Once the software initialises, uncheck the 340 nm Baseline Correction box.

(3) Blank the instrument with Milli-Q water.

(4) Test a Milli-Q water sample to ensure that the background is zero. If necessary, re-clean the sample pedestal with Milli-Q water.

(5) Determine the Total RNA concentration of each sample using a single determination.

(6) Calculate the Total RNA Yield and Yield per Cell.

(7) Calculate the volume of 1.0-2.0 µg Total RNA for each sample. (A maximum of 2.0 µg Total RNA can be Reverse Transcribed per cDNA reaction).

(8) The Total RNA concentration must be ≥100 ng/µL to meet the requirement of 1 µg Total RNA per 10 µL (maximum volume) for Reverse Transcription. Re-isolate Total RNA from a fresh vial of cells if necessary.

The expected Total RNA yield per $1 \times 10^6$ cryopreserved iPSC-MSCs is ~5-10 µg. This is equivalent to ~5-10 µg Total RNA per cell.

xiii) Proceed to cDNA synthesis or store the Total RNA at −20° C. for up to 1 year.

f) Preparation of cDNA Using the High Capacity RNA-to-cDNA™ Kit.

i) For each Total RNA sample, prepare cDNA +/−RT using 1 µg Total RNA/22 µL RT. Include $H_2O$ (NTC)+/−RT Controls (N=14)

ii) Thaw the kit components on ice.

iii) Prepare one +RT and one −RT Master Mix on ice, depending on the number of Total RNA samples to be analyzed. The −RT samples serve as negative controls, lacking reverse transcriptase. Include $H_2O$ (NTC)+/−RT Controls by replacing Total RNA with RT-PCR Grade Water.

iv) Prepare individual +/−RT Reaction Mixes on ice for each Total RNA sample.

(1) The maximum volume of Total RNA is 10 µL per 22 µL+/−RT. The volume of Total RNA will vary, depending on the Total RNA concentration.

(2) Calculate the volume of RT-PCR Grade Water for each tube by subtracting the Total RNA volume from 10 µL.

(3) Pipet the appropriate volume of RT-PCR Grade Water into each tube. Use 10 µL for the +/−RT $H_2O$ Controls.

(4) Add the appropriate volume of Total RNA to each tube.

(5) Add 12 µL of +RT or −RT Master Mix to each tube and mix gently by pipetting.

v) Incubate at 37° C. for 60 minutes.

vi) Heat inactivate at 95° C. for 5 minutes.

vii) Briefly centrifuge the tubes to collect the cDNA.

viii) Measure the cDNA volume using a calibrated 10-100 µL pipet.

(1) Set the pipet to the cDNA reaction volume (20-22 µL) and measure the cDNA volume.

(2) Adjust the cDNA volume to 100 µL with Nuclease-Free Water. This will dilute inhibitors and provide enough cDNA for multiple qRT-PCR assays.

ix) Mix by vortexing and briefly spin down the samples.

x) Proceed to qRT-PCR or store at −20° C.

g) qRT-PCR (TaqMan® Gene Expression Assays)

i) For each cDNA (N=14), amplify 50 ng cDNA (Total RNA equivalents) per 20 µL qRT-PCR for LIN28 and GAPDH (N=3 each). Perform qRT-PCR using 50 cycles. (Protocol File: TaqMan qRT-PCR Assays Cq(50).prcl).

ii) Prepare a cDNA Amplification Mix for each +RT and −RT cDNA, depending on the number of replicates and number of TaqMan® GE Assays to be performed.

(1) The recommended maximum amount of cDNA per reaction is 100 ng (Total RNA equivalents).

iii) Prepare a GE Assay Mix for each cDNA, depending on the number of TaqMan® GE Assays and replicates. One GE Assay Mix will be prepared for each cDNA and each TaqMan® GE Assay to be performed.

iv) Transfer 20 µL of each GE Assay Mix into a white CFX96 plate and seal with an optical plate sealer.

v) Centrifuge the plate at 400 rpm for 1 minute in a centrifuge with a plate adapter (ID #0018) to collect the contents to the bottom of the wells.

vi) Carefully place the plate in the thermal cycler, being careful not to disturb the contents of the wells.

vii) Program the Bio-Rad CFX96 Real-Time PCR Detection System using the Bio-Rad CFX Manager™ software on the attached computer. with the following Thermal Cycling Parameters:

(1) 2 minutes @ 50.0° C. (UNG incubation; required for optimal uracil-N-glycosylase activity; degrades previously amplified, dUTP-incorporated PCR products to reduce PCR contamination).

(2) 10 minutes @ 95° C. (Hot Start: AmpliTaq Gold®, UP Polymerase activation).

(3) [15 seconds @ 95° C. (denaturation)+1 minute @ 60° C. (annealing/extension)+Plate Read]–repeat 49 times for 50 cycles (amplification and real-time detection).

viii) Set the Sample Volume to 20 μL.

ix) The Estimated Run Time should be 01:59:00 h.

x) Read all wells and all channels during the run to make sure that all data is collected during the run.

(1) The Preview settings, located above the plate layout, should be:

(a) Fluorophores: FAM, HEX, Texas Red, Cy5, Quasar 705 (VIC can be added later)

(b) Plate Type: BR White (c) Scan Mode: All Channels xi) All wells should be labeled "Unk," indicating that the software considers all wells to be Unknown during the run. The actual plate layout will be set up after the run is complete.

xii) Click on Next to move to the Start Run Tab. Enter identifying information about the run in the Notes section.

xiii) Click on the Start Run Button to begin qRT-PCR.

h) Data Analysis i) The Data Analysis window will open at the end of the run.

(1) qRT-PCR data is reported as Cq values (i.e. Cq(50)).

ii) Click on the Plate Setup button on the top, right side of the window.

(1) Select View/Edit Plate. Follow the Plate Loading Guide to set up the plate with sample information.

(a) Clear any empty wells.

(b) Do not check, "Exclude Wells in Analysis." All data must be analyzed.

(2) Click on OK and save the file.

iii) Click on the Quantification tab near the top of the window.

iv) Check the following Settings:

(1) Cq Determination Mode: Single Threshold (2) Baseline Setting: Baseline Subtracted Curve Fit (3) Analysis Mode: Fluorophore v) Generate a report from the Tools menu with the following sections and associated subsections: Header, Run Setup, Quantification and QC Parameters.

(1) Deselect Gene Expression options, Allelic Discrimination and End Point, as these sections are not relevant.

vi) Export data for analysis by selecting Export >"Export All Data Sheets to Excel." This will provide the data in spreadsheet format.

vii) Analyze the data using a spreadsheet.

(1) Report "N/A" as "No Cq(50)."

(2) Calculate the Av. Cq(50) and % relative standard deviation (RSD, or coefficient of variation (CV)) for each LIN28 and GAPDH +/−RT data set.

(3) Normalise the Av. Cq(50) values by subtracting Av. GAPDH Cq(50) (N=3) from Av. LIN28 Cq(50) (N=3).

(4) Calculate the Av. GAPDH Cq(50) and % RSD for all samples.

(5) Compare the Normalised Av. Cq(50) values of Samples #2 (iPSC-MSC (expanded)) and #4 (iPSC-MSC plus 0.001% iPSC Spike (expanded)). Compare the Normalised Av. Cq(50) values of Samples #4 (iPSC-MSC plus 0.001% iPSC Spike (expanded)) and #6 (iPSC-MSC P5 Final Product (expanded)).

4) Acceptance Criteria a) The Normalised Av. Cq(50) value of Sample #2 (iPSC-MSC (expanded)) must be greater than the Normalised Av. Cq(50) value of Sample #4 (iPSC-MSC plus 0.001% iPSC Spike (expanded)). This demonstrates that the 0.001% iPSC Spike (expanded) can be detected above background.

TABLE 7

Expected Av. Norm. Cq(50) values for reference cultures for iPSC-MSC P5 final product.

| Sample # | Spike | Expansion | Expected Av. Norm. Cq(50)* |
|---|---|---|---|
| 1 | No | No | 15.16 ± 0.29 |
| 2 | No | Yes | 19.85 ± 0.17 |
| 3 | 0.001% iPSC | No | 14.93 ± 0.06 |
| 4 | 0.001% iPSC | Yes | 13.86 ± 0.07 |

*Norm. LIN28 Cq(50) = (LIN28 Cq(50) − GAPDH Cq(50)) +/− Std. Dev. (N = 3 × 3)

b) The GAPDH Cq(50) % RSD for all samples must be ≤5%. The % RSD for all Average Cq(50) values and Normalised Cq(50) values must be ≤5%.

c) The $H_2O$ (NTC) Controls (+/−RT) must not produce a detectable amplification signal within 50 amplification cycles for all replicates.

i) If any of the $H_2O$ (NTC) Controls (+/−RT) are assigned a Cq(50) value, repeat the TaqMan® qRT-PCR assays from Step 3)g). This indicates contamination of the reagents by template DNA.

Example 3—Results of Protocol Performed According to Example 2

TABLE 8

Av. Norm. Cq(50) values of protocol performed according to example 2 for reference cultures and iPSC-MSC P5 final product.

| | | Av. Norm. Cq(50): iPSC-MSC-P5 | | |
|---|---|---|---|---|
| Sample # | Description | Culture 1 | Culture 2 | Culture 3 |
| 1 | iPSC-MSC (non-expanded) (Reference culture) | 15.23 | 15.33 | 14.73 |
| 2 | iPSC-MSC (expanded) (Reference culture) | 19.97 | 21.51 | 20.53 |
| 3 | iPSC-MSC plus 0.001% iPSC Spike (non-expanded) (Reference culture) | 14.90 | 15.02 | 14.69 |
| 4 | iPSC-MSC plus 0.001% iPSC Spike (expanded) (Reference culture) | 14.30 | 14.20 | 13.99 |
| 5 | iPSC-MSC P5 Final Product (non-expanded) | 15.97 | 15.42 | 14.09 |
| 6 | iPSC-MSC P5 Final Product (expanded) | 20.46 | 21.06 | 20.72 |

Example 4—Quantitation of Residual Undifferentiated Stem Cells by qRT-PCR

This example describes quantitation of residual, undifferentiated iPSCs essentially by the protocol of example 2, but LIN28 is replaced by OCT4 (POU5F1). The anticipated results are in line with example 2, table 7 and example 3, table 8.

Example 5—Quantitation of Residual Undifferentiated Stem Cells by qRT-PCR

This example describes quantitation of residual, undifferentiated iPSCs essentially by the protocol of example 2, but LIN28 is replaced by SOX2. The anticipated results are in line with example 2, table 7 and example 3, table 8.

Example 6—Quantitation of Residual Undifferentiated Stem Cells by qRT-PCR

This example describes quantitation of residual, undifferentiated iPSCs essentially by the protocol of example 2, but LIN28 is replaced by FOXD3. The anticipated results are in line with example 2, table 7 and example 3, table 8.

Example 7—Quantitation of Residual Undifferentiated Stem Cells by qRT-PCR

This example describes quantitation of residual, undifferentiated iPSCs essentially by the protocol of example 2, but LIN28 is replaced by NANOG. The anticipated results are in line with example 2, table 7 and example 3, table 8.

Example 8—Quantitation of Residual Undifferentiated Stem Cells by qRT-PCR

This example describes quantitation of residual, undifferentiated iPSCs essentially by the protocol of example 2, but LIN28 is replaced by PODXL. The anticipated results are in line with example 2, table 7 and example 3, table 8.

Example 9—Quantitation of Residual Undifferentiated Stem Cells by qRT-PCR

This example describes quantitation of residual, undifferentiated iPSCs essentially by the protocol of example 2, but LIN28 is replaced by REX1 (ZFP42). The anticipated results are in line with example 2, table 7 and example 3, table 8.

Example 10—Quantitation of Residual Undifferentiated Stem Cells by qRT-PCR

This example describes quantitation of residual, undifferentiated iPSCs essentially by the protocol of example 2, but LIN28 is replaced by SSEA1 (FUT4). The anticipated results are in line with example 2, table 7 and example 3, table 8.

Example 11—Quantitation of Residual Undifferentiated Stem Cells by qRT-PCR

This example describes quantitation of residual, undifferentiated iPSCs essentially by the protocol of example 2, but LIN28 is replaced by SSEA4. The anticipated results are in line with example 2, table 7 and example 3, table 8.

Example 12—Quantitation of Residual Undifferentiated Stem Cells by qRT-PCR

This example describes quantitation of residual, undifferentiated iPSCs essentially by the protocol of example 2, but LIN28 is replaced by DPPA2. The anticipated results are in line with example 2, table 7 and example 3, table 8.

Example 13—Quantitation of Residual Undifferentiated Stem Cells by qRT-PCR

This example describes quantitation of residual, undifferentiated iPSCs essentially by the protocol of example 2, but LIN28 is replaced by DPPA3. The anticipated results are in line with example 2, table 7 and example 3, table 8.

---

The invention claimed is:

1. A method for detecting residual, undifferentiated pluripotent stem cells (PSCs) in a culture of cells differentiated from PSCs, the method comprising:
culturing the cells on a substrate coated with laminin-521 and E-cadherin, in a medium consisting essentially of a Rho-associated, coiled-coil containing protein kinase (ROCK) inhibitor for about three days, followed by culturing the cells in a medium not comprising a ROCK inhibitor or other inhibitor for about two days; wherein the culturing selectively expands the residual, undifferentiated PSCs in the culture of cells differentiated from PSCs, and wherein the residual, undifferentiated PSCs are not differentiated during the selective expansion;

quantifying in the culture of cells expression of a marker of residual, undifferentiated PSCs; and comparing the marker expression in the culture of cells with the marker expression in a reference culture of cells comprising a known proportion of PSCs, wherein lower marker expression in the culture of cells than marker expression in the reference culture of cells indicates absence of residual, undifferentiated PSCs in the culture of cells or presence of residual, undifferentiated PSCs in the culture of cells at a proportion lower than the known proportion of PSCs in the reference culture of cells, thereby detecting residual, undifferentiated PSCs in the culture of cells differentiated from PSCs.

2. The method of claim 1, wherein the marker expression is LIN28, OCT4, SOX2, FOXD3, NANOG, PODXL, REX1, SSEA1, SSEA4, DPPA2 or DPPA3 expression.

3. The method of claim 1, wherein the ROCK inhibitor is Y27632.

4. The method of claim 3, wherein the cells are cultured in about 10 μM Y27632.

5. The method of claim 1, wherein the marker expression is quantified by polymerase chain reaction (PCR).

6. The method of claim 5, wherein the PCR is quantitative real time PCR (qRT-PCR).

7. The method of claim 6, wherein the qRT-PCR comprises a probe consisting of 5'→3' sequence CGCATGGGGTTCGGCTTCCTGTCC (SEQ ID NO: 15), a primer consisting of 5'→3' sequence CACGGTGCGGGCATCTG (SEQ ID NO: 16), and a primer consisting of 5'→3' sequence CCTTCCATGTGCAGCTTACTC (SEQ ID NO: 17).

8. The method of claim 1, wherein the marker expression is normalised.

9. The method of claim 8, wherein the marker expression is normalised to GAPDH expression.

10. The method of claim 1, wherein the known proportion is 0.001%.

11. The method of claim 1, wherein the PSCs are iPSCs.

12. The method of claim 1, wherein the cells are MSCs.

13. The method of claim 12, wherein the MSCs are cultured in E8 Complete Medium.

14. A method for manufacturing a therapeutic composition, the method comprising formulating into a composition for therapeutic administration to a subject a culture of cells in which residual, undifferentiated PSCs are absent or lower than a known proportion when detected by the method of claim 1.

* * * * *